(12) United States Patent
Dong et al.

(10) Patent No.: US 9,315,472 B2
(45) Date of Patent: Apr. 19, 2016

(54) 1,3,5-TRIAZINANE-2,4,6-TRIONE DERIVATIVES AND USES THEREOF

(71) Applicant: Massachusetts Institute of Technology, Cambridge, MA (US)

(72) Inventors: Yizhou Dong, Natick, MA (US); Akinleye C. Alabi, Cambridge, MA (US); Hao Yin, Cambridge, MA (US); Joseph R. Dorkin, Somerville, MA (US); Delai Chen, Cambridge, MA (US); Robert S. Langer, Newton, MA (US); Daniel Griffith Anderson, Sudbury, MA (US); Ahmed A. Eltoukhy, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/267,530

(22) Filed: May 1, 2014

(65) Prior Publication Data

US 2014/0329884 A1 Nov. 6, 2014

Related U.S. Application Data

(60) Provisional application No. 61/818,295, filed on May 1, 2013.

(51) Int. Cl.
| | |
|---|---|
| *C07D 251/30* | (2006.01) |
| *A61K 31/53* | (2006.01) |
| *A61K 31/713* | (2006.01) |

(52) U.S. Cl.
CPC .............. *C07D 251/30* (2013.01); *A61K 31/53* (2013.01); *A61K 31/713* (2013.01)

(58) Field of Classification Search
CPC .................................................... C07D 251/30
USPC ......................................... 544/222; 514/241
See application file for complete search history.

(56) References Cited

U.S. PATENT DOCUMENTS

| | | | |
|---|---|---|---|
| 2,647,121 | A | 7/1953 | Jacoby |
| 2,717,909 | A | 9/1955 | Kosmin |
| 2,819,718 | A | 1/1958 | Goldman |
| 2,844,629 | A | 7/1958 | William et al. |
| 3,096,560 | A | 7/1963 | Liebig |
| 3,350,325 | A | 10/1967 | Ashby et al. |
| 3,535,289 | A | 10/1970 | Yoshihara et al. |

(Continued)

FOREIGN PATENT DOCUMENTS

| | | |
|---|---|---|
| CA | 2518132 A1 | 3/2006 |
| CA | 2 769 408 A1 | 2/2011 |

(Continued)

OTHER PUBLICATIONS

Manabe et al. JP2014172827, Mar. 6, 2013; CA 161: 1570959, 2014. CAPLUS Abstract provided.*

(Continued)

*Primary Examiner* — Venkataraman Balasubramanian

(74) *Attorney, Agent, or Firm* — Wolf, Greenfield & Sacks, P.C.

(57) ABSTRACT

The present invention provides novel 1,3,5-triazinane-2,4,6-trione derivatives, such as compounds of any one of Formulae (I) and (II), and salts thereof, and methods of preparing the compounds. Also provided are compositions including a compound of the invention and an agent (e.g., an siRNA, mRNA, or plasmid DNA). The present invention also provides methods and kits using the compositions for delivering an agent to a subject (e.g., to the liver, spleen, or lung of the subject) or cell and for treating and/or preventing a range of diseases, such as genetic diseases, proliferative diseases, hematological diseases, neurological diseases, liver diseases, and lung diseases.

25 Claims, 6 Drawing Sheets

(56) References Cited

U.S. PATENT DOCUMENTS

| | | |
|---|---|---|
| 3,614,954 A | 10/1971 | Mirowski et al. |
| 3,614,955 A | 10/1971 | Mirowski |
| 3,656,185 A | 4/1972 | Carpentier |
| 3,805,301 A | 4/1974 | Liebig |
| 3,945,052 A | 3/1976 | Liebig |
| 3,995,623 A | 12/1976 | Blake et al. |
| 4,013,507 A | 3/1977 | Rembaum |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,197,977 A | 3/1993 | Hoffman, Jr. et al. |
| 5,200,395 A | 4/1993 | Eto et al. |
| 5,201,998 A * | 4/1993 | Topfl et al. .................. 162/158 |
| 5,261,419 A | 11/1993 | Osypka |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,352,461 A | 10/1994 | Feldstein et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,607,385 A | 3/1997 | Francischelli et al. |
| 5,609,624 A | 3/1997 | Kalis |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,736,573 A | 4/1998 | Galat |
| 5,772,694 A | 6/1998 | Bokros et al. |
| 5,776,165 A | 7/1998 | Ripart |
| 5,776,747 A | 7/1998 | Schinstine et al. |
| 5,817,873 A * | 10/1998 | Meyer et al. .................. 564/158 |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,976,569 A | 11/1999 | Milstein |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,152,955 A | 11/2000 | KenKnight et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,271,209 B1 | 8/2001 | Smith et al. |
| 6,299,604 B1 | 10/2001 | Ragheb et al. |
| 6,331,318 B1 | 12/2001 | Milstein |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,696,424 B1 | 2/2004 | Wheeler |
| 6,756,055 B2 | 6/2004 | McDonald et al. |
| 6,821,530 B2 | 11/2004 | Koob et al. |
| 6,887,665 B2 | 5/2005 | Trulson et al. |
| 6,998,115 B2 | 2/2006 | Langer et al. |
| 7,022,214 B2 | 4/2006 | Olech |
| 7,084,303 B2 | 8/2006 | Watanabe et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,972,435 B2 | 7/2011 | Bury et al. |
| 7,977,452 B2 | 7/2011 | Tomalia et al. |
| 8,071,082 B2 | 12/2011 | Zugates et al. |
| RE43,612 E | 8/2012 | Anderson et al. |
| 8,287,849 B2 | 10/2012 | Langer et al. |
| 8,361,555 B2 | 1/2013 | Paquet, Jr. |
| 8,450,298 B2 | 5/2013 | Mahon et al. |
| 8,557,231 B2 | 10/2013 | Langer et al. |
| 8,562,966 B2 | 10/2013 | Zugates et al. |
| 8,808,681 B2 | 8/2014 | Anderson et al. |
| 8,969,353 B2 | 3/2015 | Mahon et al. |
| 9,006,487 B2 | 4/2015 | Anderson et al. |
| 2002/0022721 A1 | 2/2002 | Trulson et al. |
| 2002/0094528 A1 | 7/2002 | Salafsky |
| 2002/0192721 A1 | 12/2002 | Rizzuto et al. |
| 2002/0193622 A1 | 12/2002 | Watanabe et al. |
| 2003/0215395 A1 | 11/2003 | Yu et al. |
| 2004/0235982 A1 | 11/2004 | Rabasco et al. |
| 2005/0059005 A1 | 3/2005 | Tuschl et al. |
| 2005/0069590 A1 | 3/2005 | Buehler et al. |
| 2005/0143332 A1 | 6/2005 | Monahan et al. |
| 2005/0148786 A1 | 7/2005 | Ikeda et al. |
| 2005/0244961 A1 | 11/2005 | Short et al. |
| 2006/0223939 A1 | 10/2006 | Lange et al. |
| 2006/0228404 A1 | 10/2006 | Anderson et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2010/0036084 A1 | 2/2010 | Langer et al. |
| 2010/0178699 A1 | 7/2010 | Gao et al. |

(56) References Cited

U.S. PATENT DOCUMENTS

| | | |
|---|---|---|
| 2010/0331234 A1 | 12/2010 | Mahon et al. |
| 2011/0009641 A1 | 1/2011 | Anderson et al. |
| 2011/0158935 A1 | 6/2011 | Kraft |
| 2011/0293703 A1 | 12/2011 | Mahon et al. |
| 2012/0009222 A1 | 1/2012 | Nguyen et al. |
| 2012/0065358 A1 | 3/2012 | Langer et al. |
| 2012/0128760 A1 | 5/2012 | Manoharan et al. |
| 2012/0196923 A1 | 8/2012 | Rege et al. |
| 2012/0251560 A1 | 10/2012 | Dahlman et al. |
| 2013/0158021 A1 | 6/2013 | Dong et al. |
| 2013/0302401 A1 | 11/2013 | Ma et al. |
| 2014/0094399 A1 | 4/2014 | Langer et al. |
| 2014/0161830 A1 | 6/2014 | Anderson et al. |
| 2015/0203439 A1 | 7/2015 | Mahon et al. |

FOREIGN PATENT DOCUMENTS

| | | |
|---|---|---|
| CN | 101506196 A | 8/2009 |
| CN | 100 569 877 C | 12/2009 |
| CN | 101 863 544 B | 9/2011 |
| DE | 2430998 A1 | 1/1975 |
| DE | 2520814 A1 | 11/1976 |
| EP | 0 673 637 A1 | 9/1995 |
| EP | 0 959 092 A1 | 11/1999 |
| EP | 1 912 679 A2 | 4/2008 |
| EP | 2 045 251 A1 | 4/2009 |
| EP | 2 476 756 A1 | 7/2012 |
| EP | 2 532 649 | 12/2012 |
| FR | 1 378 382 | 11/1964 |
| FR | 2235112 A1 | 1/1975 |
| GB | 1072118 A | 6/1967 |
| GB | 1 602 085 A | 11/1981 |
| JP | S48-022365 A | 3/1973 |
| JP | S49-127908 A | 12/1974 |
| JP | 50-24216 A | 3/1975 |
| JP | S51-023537 A | 2/1976 |
| JP | 51-125144 | 11/1976 |
| JP | S52-010847 A | 1/1977 |
| JP | 63-125144 A | 5/1988 |
| JP | 63-154788 A | 6/1988 |
| JP | 4-108173 A | 4/1992 |
| JP | H07-053535 A | 2/1995 |
| JP | H09-505593 A | 6/1997 |
| JP | H10-197978 A | 7/1998 |
| JP | 11-005786 A | 1/1999 |
| JP | 11-080142 A | 3/1999 |
| JP | 2001-523215 A | 11/2001 |
| JP | 2002-167368 A | 6/2002 |
| JP | 2003-519199 A | 6/2003 |
| JP | 2008-247749 A | 10/2008 |
| WO | WO 93/18229 A1 | 9/1993 |
| WO | WO 93/18754 A1 | 9/1993 |
| WO | WO 95/11004 A1 | 4/1995 |
| WO | WO 95/14651 A1 | 6/1995 |
| WO | WO 96/26179 A1 | 8/1996 |
| WO | WO 96/36314 A2 | 11/1996 |
| WO | WO 97/23457 A1 | 7/1997 |
| WO | WO 98/16202 A1 | 4/1998 |
| WO | WO 00/03044 A1 | 1/2000 |
| WO | WO 01/15726 A2 | 3/2001 |
| WO | WO 02/22709 A1 | 3/2002 |
| WO | WO 02/31025 A2 | 4/2002 |
| WO | WO 02/097068 A2 | 12/2002 |
| WO | WO 03/040288 A2 | 5/2003 |
| WO | WO 03/070735 A2 | 8/2003 |
| WO | WO 2004/043588 A2 | 5/2004 |
| WO | WO 2004/048345 A2 | 6/2004 |
| WO | WO 2004/106411 | 12/2004 |
| WO | WO 2005/028619 A2 | 3/2005 |
| WO | WO 2005/121348 A1 | 12/2005 |
| WO | WO 2006/065266 A2 | 6/2006 |
| WO | WO 2006/082088 A1 | 8/2006 |
| WO | WO 2006/105043 A2 | 10/2006 |
| WO | WO 2006/138380 | 12/2006 |
| WO | WO 2007/143659 | 12/2007 |
| WO | WO 2008/011561 | 1/2008 |
| WO | WO 2008/036168 A2 | 3/2008 |
| WO | WO 2008/113364 A2 | 9/2008 |
| WO | WO 2008/119741 A2 | 10/2008 |
| WO | WO 2009/046220 A2 | 4/2009 |
| WO | WO 2010/042877 A1 | 4/2010 |
| WO | WO 2010/045512 A2 | 4/2010 |
| WO | WO 2010/053572 | 5/2010 |
| WO | WO 2010/099387 A1 | 9/2010 |
| WO | WO 2010/114789 A1 | 10/2010 |
| WO | WO 2010/129709 A1 | 11/2010 |
| WO | WO 2011/012746 A2 | 2/2011 |
| WO | WO 2011/068810 A1 | 6/2011 |
| WO | WO 2012/027675 A2 | 3/2012 |
| WO | WO 2012/133737 A1 | 10/2012 |
| WO | WO 2012/135025 A2 | 10/2012 |
| WO | WO 2012133737 A1 * | 10/2012 |
| WO | WO 2012/170889 A1 | 12/2012 |
| WO | WO 2012/170930 A1 | 12/2012 |
| WO | WO 2013/063468 A1 | 5/2013 |
| WO | WO 2014/028487 A1 | 2/2014 |
| WO | WO 2014/179562 A1 | 11/2014 |
| WO | WO 2014/210356 A1 | 12/2014 |

OTHER PUBLICATIONS

Yamamoto et al. JP 10197978; CA 129: 493854, 1998. CAPLUS Abstract provided.*
Invitation to Pay Additional Fees for PCT/US2012/062222, mailed Dec. 14, 2012.
International Search Report and Written Opinion for PCT/US2012/062222, mailed Mar. 27, 2013.
International Preliminary Report on Patentability for PCT/US2012/062222, mailed May 8, 2014.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Akinc et al., Development of lipidoid-siRNA formulations for systemic delivery to the liver. Mol Ther. May 2009;17(5):872-9. doi: 10.1038/mt.2009.36. Epub Mar. 3, 2009.
Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.
Burnett et al., Current progress of siRNA/shRNA therapeutics in clinical trials. Biotechnol J. Sep. 2011;6(9):1130-46. doi: 10.1002/biot.201100054. Epub Jul. 11, 2011.
Byk et al., Synthesis, activity, and structure--activity relationship studies of novel cationic lipids for DNA transfer. J Med Chem. Jan. 15, 1998;41(2):224-35.
Castanotto et al.,. The promises and pitfalls of RNA-interference-based therapeutics. Nature. Jan. 22, 2009;457(7228):426-33. doi: 10.1038/nature07758.
Chakraborty, Potentiality of small interfering RNAs (siRNA) as recent therapeutic targets for gene-silencing. Curr Drug Targets. Mar. 2007;8(3):469-82.
Chen et al., Tumor-targeted delivery of siRNA by non-viral vector: safe and effective cancer therapy. Expert Opin Drug Deliv. Dec. 2008;5(12):1301-11. doi: 10.1517/17425240802568505.
Cotten et al., Receptor-mediated transport of DNA into eukaryotic cells. Methods Enzymol. 1993;217:618-44.
Damen et al., Delivery of DNA and siRNA by novel gemini-like amphiphilic peptides. J Control Release. Jul. 1, 2010;145(1):33-9. doi: 10.1016/j.jconrel.2010.03.028. Epub Apr. 8, 2010.
Davis, The first targeted delivery of siRNA in humans via a self-assembling, cyclodextrin polymer-based nanoparticle: from concept to clinic. Mol Pharm. May-Jun. 2009;6(3):659-68. doi: 10.1021/mp900015y.
Davis et al., Evidence of RNAi in humans from systemically administered siRNA via targeted nanoparticles. Nature. Apr. 15, 2010;464(7291):1067-70. doi:10.1038/nature08956. Epub Mar. 21, 2010.
Elbashir et al., RNA interference is mediated by 21- and 22-nucleotide RNAs. Genes Dev. Jan. 15, 2001;15(2):188-200.

(56) References Cited

OTHER PUBLICATIONS

Fenske et al., Liposomal nanomedicines. Expert Opin Drug Deliv. Jan. 2008;5(1):25-44.

Fire et al., Potent and specific genetic interference by double-stranded RNA in Caenorhabditis elegans. Nature. Feb. 19, 1998;391(6669):806-11.

Hammond et al., An RNA-directed nuclease mediates post-transcriptional gene silencing in *Drosophila* cells. Nature. Mar. 16, 2000;404(6775):293-6.

Hofland et al., Formation of stable cationic lipid/DNA complexes for gene transfer. Proc Natl Acad Sci U S A. Jul. 9, 1996;93(14):7305-9.

Incani et al., Lipid and hydrophobic modification of cationic carriers on route to superior gene vectors. Soft Matter. 2010; 6(10):2124-38.

Jia et al., Demonstration of two novel methods for predicting functional siRNA efficiency. BMC Bioinformatics. May 29, 2006;7:271.

Juliano et al., Biological barriers to therapy with antisense and siRNA oligonucleotides. Mol Pharm. May-Jun. 2009;6(3):686-95. doi:10.1021/mp900093r.

Kaur et al., A delineation of diketopiperazine self-assembly processes: understanding the molecular events involved in Nepsilon-(fumaroyl)diketopiperazine of L-Lys (FDKP) interactions. Mol Pharm. Mar.-Apr. 2008;5(2):294-315.

Leuschner et al., Therapeutic siRNA silencing in inflammatory monocytes in mice. Nat Biotechnol. Oct. 9, 2011;29(11):1005-10. doi: 10.1038/nbt.1989.

Li et al., Defining the optimal parameters for hairpin-based knockdown constructs. RNA. Oct. 2007;13(10):1765-74. Epub Aug. 13, 2007.

Love et al., Lipid-like materials for low-dose, in vivo gene silencing. Proc Natl Acad Sci U S A. Feb. 2, 2010;107(5):1864-9. doi: 10.1073/pnas.0910603106. Epub Jan. 11, 2010.

Lukyanov et al., Micelles from lipid derivatives of water-soluble polymers as delivery systems for poorly soluble drugs. Adv Drug Deliv Rev. May 7, 2004;56(9):1273-89.

Mathiowitz et al., Polyanhydride microspheres as drug carriers. I. Hot melt microencapsulation. J Control Release. 1987;5:13-22.

Mathiowitz et al., Novel microcapsules for delivery systems. Reactive Polymers. Oct. 1987;6(2-3):275-83.

Mathiowitz et al., Polyanhydride microspheres as drug carriers. II. Microencapsulation by solvent removal. J Appl Polymer Sci. Feb. 20, 1988;35(3):755-74.

Mintzer et al., Nonviral vectors for gene delivery. Chem Rev. Feb. 2009;109(2):259-302.

Morris et al., Lentiviral-mediated delivery of siRNAs for antiviral therapy. Gene Ther. Mar. 2006;13(6):553-8.

Naito et al., siVirus: web-based antiviral siRNA design software for highly divergent viral sequences. Nucleic Acids Res. Jul. 1, 2006;34(Web Server issue):W448-50.

Narang et al., Cationic lipids with increased DNA binding affinity for nonviral gene transfer in dividing and nondividing cells. Bioconjug Chem. Jan.-Feb. 2005;16(1):156-68.

Novina et al.,The RNAi revolution. Nature. Jul. 8, 2004;430(6996):161-4.

Parrish et al., Five- and six-membered ring opening of pyroglutamic diketopiperazine. J Org Chem. Mar. 22, 2002;67(6):1820-6.

Peer et al., Nanocarriers as an emerging platform for cancer therapy. Nat Nanotechnol. Dec. 2007;2(12):751-60. doi: 10.1038/nnano.2007.387.

Semple et al., Rational design of cationic lipids for siRNA delivery. Nat Biotechnol. Feb. 2010;28(2):172-6. doi:10.1038/nbt.1602. Epub Jan. 17, 2010.

Sen, Surfactin: biosynthesis, genetics and potential applications. Adv Exp Med Biol. 2010;672:316-23.

Siegwart et al., Combinatorial synthesis of chemically diverse core-shell nanoparticles for intracellular delivery. Proc Natl Acad Sci U S A. Aug. 9, 2011;108(32):12996-3001. doi: 10.1073/pnas.1106379108. Epub Jul. 22, 2011.

Szoka et al., Comparative properties and methods of preparation of lipid vesicles (liposomes). Annu Rev Biophys Bioeng. 1980;9:467-508.

Tan et al., Engineering Nanocarriers for siRNA Delivery. Small. Apr. 4, 2011;7(7):841-56. doi: 10.1002/smll.201001389. Epub Feb. 25, 2011.

Thiel et al., Therapeutic applications of DNA and RNA aptamers. Oligonucleotides. Sep. 2009;19(3):209-22. doi: 10.1089/oli.2009.0199.

Tranchant et al., Physicochemical optimisation of plasmid delivery by cationic lipids. J Gene. Med. Feb. 2004;6 Suppl 1:S24-35.

Van Balen et al., Liposome/water lipophilicity: methods, information content, and pharmaceutical applications. Med Res Rev. May 2004;24(3):299-324.

Walde, Preparation of vesicles (liposomes). Encyclopedia of Nanoscience and Nanotechnology, Nalwa, Ed. American Scientific Publishers: Los Angeles. 2004;9:43-79.

Weinstein et al., RNAi nanomedicines: challenges and opportunities within the immune system Nanotechnology. Jun. 11, 2010;21(23):232001. doi: 10.1088/0957-4484/21/23/232001. Epub May 13, 2010.

Whitehead et al., Knocking down barriers: advances in siRNA delivery. Nat Rev Drug Discov. Feb. 2009;8(2):129-38. doi: 10.1038/nrd2742.

Wu et al., Cationic lipid polymerization as a novel approach for constructing new DNA delivery agents. Bioconjug Chem. Mar.-Apr. 2001;12(2):251-7.

Yiu et al., Filtering of ineffective siRNAs and improved siRNA design tool. Bioinformatics. Jan. 15, 2005;21(2):144-51. Epub Aug. 27, 2004.

Zamora et al., RNA interference therapy in lung transplant patients infected with respiratory syncytial virus. Am J Respir Crit Care Med. Feb. 15, 2011;183(4):531-8. doi: 10.1164/rccm.201003-0422OC. Epub Sep. 17, 2010.

Zamore et al.,RNAi: double-stranded RNA directs the ATP-dependent cleavage of mRNA at 21 to 23 nucleotide intervals. Cell. Mar. 31, 2000;101(1):25-33.

Zaugg et al., 3-Carboxy-2,5-piperazinedione and Derivatives. J Amer Chem Soc. Jun. 5, 1956;78(11):2626-2631.

Zhao et al., A developmental view of microRNA function. Trends Biochem Sci. Apr. 2007;32(4):189-97. Epub Mar. 9, 2007. Review.

Adami et al., An amino acid-based amphoteric liposomal delivery system for systemic administration of siRNA. Mol Ther. Jun. 2011;19(6):1141-51.

Akinc et al., Exploring polyethylenimine-mediated DNA transfection and the proton sponge hypothesis. J Gene Med. May 2005;7(5):657-63.

Akinc et al., Parallel synthesis and biophysical characterization of a degradable polymer library for gene delivery. J Am Chem Soc. May 7, 2003;125(18):5316-23.

Alshamsan et al., The induction of tumor apoptosis in B16 melanoma following STAT3 siRNA delivery with a lipid-substituted polyethylenimine. Biomaterials. Feb. 2010;31(6):1420-8. Epub Nov. 13, 2009.

Anderson et al., Structure/property studies of polymeric gene delivery using a library of poly(beta-amino esters). Mol Ther. Mar. 2005;11(3):426-34.

Anderson, Biological Responses to Materials. Annu Rev Mater Res. 2001;31:81-110.

Anderson, Chapter 4. Mechanisms of Inflammation and Infection With Implanted Devices. Cardiovasc Pathol. 1993;2:33S-41S.

Anderson, Human gene therapy. Nature. Apr. 30, 1998;392(6679 Suppl):25-30. Review.

Asokan et al., Cytosolic delivery of macromolecules. 3. Synthesis and characterization of acid-sensitive bis-detergents. Bioconjug Chem. Nov.-Dec. 2004;15(6):1166-73.

Bajaj et al., Synthesis and gene transfection efficacies of PEI-cholesterol-based lipopolymers. Bioconjug Chem. Aug. 2008;19(8):1640-51. Epub Jul. 11, 2008.

Behr et al., Efficient gene transfer into mammalian primary endocrine cells with lipopolyamine coated DNA. Proc Natl Acad Sci U S A. Sep. 1989;86(18):6982-6.

Behr, Synthetic gene-transfer vectors. Acc Chem Res. 1993;26:274-278.

(56) References Cited

OTHER PUBLICATIONS

Berge et al., Pharmaceutical salts. J Pharm Sci. Jan. 1977;66(1):1-19.
Boudou et al., Multiple functionalities of polyelectrolyte multilayer films: new biomedical applications. Adv Mater. Jan. 26, 2010;22(4):441-67.
Bourque et al., Hydroformylation Reactions Using Recyclable Rhodium-Complexed Dendrimers on Silica. J Am Chem Soc. 2000;122(5):956-957.
Boussif et al., A versatile vector for gene and oligonucleotide transfer into cells in culture and in vivo: polyethylenimine. Proc Natl Acad Sci U S A. Aug. 1, 1995;92(16):7297-301.
Braun et al., Structure/function relationships of polyamidoamine/DNA dendrimers as gene delivery vehicles. J Pharm Sci. Feb. 2005;94(2):423-36.
Breunig et al., Breaking up the correlation between efficacy and toxicity for nonviral gene delivery. Proc Natl Acad Sci U S A. Sep. 4, 2007;104(36):14454-9. Epub Aug. 28, 2007.
Breunig et al., Mechanistic investigation of poly(ethylene imine)-based siRNA delivery: disulfide bonds boost intracellular release of the cargo. J Control Release. Aug. 25, 2008;130(1):57-63. Epub May 24, 2008.
Brey et al., Controlling poly(beta-amino ester) network properties through macromer branching. Acta Biomater. Mar. 2008;4(2):207-17. Epub Oct. 22, 2007.
Brey et al., Influence of macromer molecular weight and chemistry on poly(beta-amino ester) network properties and initial cell interactions. J Biomed Mater Res A. Jun. 1, 2008;85(3):731-41.
Brodbeck et al., Biomaterial surface chemistry dictates adherent monocyte/macrophage cytokine expression in vitro. Cytokine. Jun. 21, 2002;18(6):311-9.
Chang, Therapeutic applications of polymeric artificial cells. Nat Rev Drug Discov. Mar. 2005;4(3):221-35.
Chen et al., Polymeric growth factor delivery strategies for tissue engineering. Pharm Res. Aug. 2003;20(8):1103-12.
Chen et al., Rapid discovery of potent siRNA-containing lipid nanoparticles enabled by controlled microfluidic formulation. J Am Chem Soc. Apr. 25, 2012;134(16):6948-51. doi: 10.1021/ja301621z. Epub Apr. 10, 2012.
Conte et al., Regioselective ring opening of [(perfluoroalkyl)methyl] oxiranes with N-nucleophiles. J Fluorine Chem. 2005;126(9-10):1274-80.
Creusat et al., Proton sponge trick for pH-sensitive disassembly of polyethylenimine-based siRNA delivery systems. Bioconjug Chem. May 19, 2010;21(5):994-1002.
Crystal, Transfer of genes to humans: early lessons and obstacles to success. Science. Oct. 20, 1995;270(5235):404-10. Review.
Decher, Fuzzy Nanoassemblies: Toward Layered Polymeric Multicomposites. Science. 1997;277;1232-37.
Deshmukh et al., Liposome and polylysine mediated gene therapy. New J Chem. 1997;21:113-124.
Discher et al., Polymer vesicles. Science. Aug. 9, 2002;297(5583):967-73. Review.
Discher et al., Polymersomes: tough vesicles made from diblock copolymers. Science. May 14, 1999;284(5417):1143-6.
Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014.
Ewert et al., Cationic lipid-DNA complexes for gene therapy: understanding the relationship between complex structure and gene delivery pathways at the molecular level. Curr Med Chem. Jan. 2004;11(2):133-49.
Felgner et al., Lipofection: a highly efficient, lipid-mediated DNA-transfection procedure. Proc Natl Acad Sci U S A. Nov. 1987;84(21):7413-7.
Ferruti et al., A novel modification of poly(1-lysine) leading to a soluble cationic polymer with reduced toxicity and with potential as a transfection agent. Macromol Chem Phys 1998;199:2565-75.
Ferruti et al., Linear amino polymers: Synthesis, protonation and complex formation. Advances in Polymer Science. 1984;58:55-92.
Fisher et al., Photoinitiated Polymerization of Biomaterials. Annu Rev Mater Res. 2001;31:171-81.
Friedmann, Human gene therapy—an immature genie, but certainly out of the bottle. Nat Med. Feb. 1996;2(2):144-7.
Furgeson et al., Modified linear polyethylenimine-cholesterol conjugates for DNA complexation. Bioconjug Chem. Jul.-Aug. 2003;14(4):840-7.
Furgeson et al., Novel water insoluble lipoparticulates for gene delivery. Pharm Res. Apr. 2002;19(4): 382-90.
Geng et al., Hydrolytic degradation of poly(ethylene oxide)-block-polycaprolactone worm micelles. J Am Chem Soc. Sep. 21, 2005;127(37):12780-1.
Ghosh et al., Toll-like receptor (TLR) 2-9 agonists-induced cytokines and chemokines: I. Comparison with T cell receptor-induced responses. Cell Immunol. Sep. 2006;243(1):48-57. Epub Jan. 23, 2007.
Godbey et al., Size matters: molecular weight affects the efficiency of poly(ethylenimine) as a gene delivery vehicle. J Biomed Mater Res. Jun. 5, 1999;45(3):268-75.
Gonzalez et al., New class of polymers for the delivery of macromolecular therapeutics. Bioconjug Chem. Nov.-Dec. 1999;10(6):1068-74.
Grayson et al., Biophysical and structural characterization of polyethylenimine-mediated siRNA delivery in vitro. Pharm Res. Aug. 2006;23(8):1868-76.
Grunlan et al., Synthesis of 1,9-bis[glycidyloxypropyl]penta(1'H, 1'H, 2'H, 2'H-perfluoroalkylmethylsiloxane)s and copolymerization with piperazine. Polymer. 2004;45:2517-23.
Gunatillake et al., Recent developments in biodegradable synthetic polymers. Biotechnol Annu Rev. 2006;12:301-47.
Haensler et al., Polyamidoamine cascade polymers mediate efficient transfection of cells in culture. Bioconjug Chem. Sep.-Oct. 1993;4(5):372-9.
Harder et al., Molecular Conformation in Oligo(ethylene glycol)-Terminated Self-Assembled Monolayers on Gold and Silver Surfaces Determines Their Ability to Resist Protein Adsorpotion. J Phys Chem B. 1998;102:426-36.
Heyes et al., Cationic lipid saturation influences intracellular delivery of encapsulated nucleic acids. J Control Release. Oct. 3, 2005;107(2):276-87.
Hill et al., Enantioselective Epoxidation of Allylic Alcohols: (2S,3S)-3-Propyloxiranemethanol. Org Syn. 1990;7:461.
Hill et al., In vitro cytotoxicity of poly(amidoamine)s: relevance to DNA delivery. Biochim Biophys Acta. Apr. 19, 1999;1427(2):161-74.
Holmlin et al., Zwitterionic SAMs that Resist Nonspecific Adsorption of Protein from Aqueous Buffer. Langmuir. 2001;17:2841-50.
Hope et al., Cationic Lipids, Phosphatidylethanolamine and the Intracellular Delivery of Polymeric, Nucleic Acid-Based Drugs. Molecular Membrane Technology. 1998;15:1-14.
Howard, Delivery of RNA interference therapeutics using polycation-based nanoparticles. Adv Drug Deliv Rev. Jul. 25, 2009;61(9):710-20. Epub Apr. 5, 2009.
Hunt et al., Effect of biomaterial surface charge on the inflammatory response: evaluation of cellular infiltration and TNF alpha production. J Biomed Mater Res. May 1996;31(1):139-44.
Ichimaru et al., Synthesis and characterization of new piperazine-type inhibitors for mitochondrial NADH-ubiquinone oxidoreductase (complex I). Biochemistry. Oct. 7, 2008;47(40):10816-26. Epub Sep. 10, 2008.
Ingber et al., Mechanochemical switching between growth and differentiation during fibroblast growth factor-stimulated angiogenesis in vitro: role of extracellular matrix. J Cell Biol. Jul. 1989;109(1):317-30.
Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263. Epub Jul. 10, 2012.
Jiang et al., Electrochemically controlled release of lipid/DNA complexes: a new tool for synthetic gene delivery system. Electrochem Commun. 2004;6:576-82.

(56) References Cited

OTHER PUBLICATIONS

Jiang et al., Hyaluronic acid-polyethyleneimine conjugate for target specific intracellular delivery of siRNA. Biopolymers. Jul. 2008;89(7):635-42.

Jiang et al., Ultralow-fouling, functionalizable, and hydrolyzable zwitterionic materials and their derivatives for biological applications. Adv Mater. Mar. 5, 2010;22(9):920-32.

Jolck et al., Solid-phase synthesis of PEGylated lipopeptides using click chemistry. Bioconjug Chem. May 19, 2010;21(5):807-10.

Jon et al., Degradable poly(amino alcohol esters) as potential DNA vectors with low cytotoxicity. Biomacromolecules. Nov.-Dec. 2003;4(6):1759-62.

Kabanov et al., DNA complexes with polycations for the delivery of genetic material into cells. Bioconjug Chem. Jan.-Feb. 1995;6(1):7-20.

Kamath et al., Surface chemistry influences implant-mediated host tissue responses. J Biomed Mater Res A. Sep. 2008;86(3):617-26.

Katsuki et al., Chapter 1. Asymmetric Epoxidation of Allylic Alcohols: The Katsuki-Sharpless Epoxidation Reaction. Org React 1996;48:1-299.

Katsuki et al., The First Practical Method for Asymmetric Epoxidation. J Am Chem Soc. 1980:102;5974-76.

Kim et al., Comparative evaluation of target-specific GFP gene silencing efficiencies for antisense ODN, synthetic siRNA, and siRNA plasmid complexed with PEI-PEG-FOL conjugate. Bioconjug Chem. Jan.-Feb. 2006;17(1):241-4.

Kim et al., Efficient siRNA delivery using water soluble lipopolymer for anti-angiogenic gene therapy. J Control Release. Apr. 23, 2007;118(3):357-63. Epub Jan. 9, 2007.

Kim et al., Local and systemic delivery of VEGF siRNA using polyelectrolyte complex micelles for effective treatment of cancer. J Control Release. Jul. 14, 2008;129(2):107-16. Epub Mar. 14, 2008.

Kim et al., Synthesis of biodegradable cross-linked poly(beta-amino ester) for gene delivery and its modification, inducing enhanced transfection efficiency and stepwise degradation. Bioconjug Chem. Sep.-Oct. 2005;16(5):1140-8.

Kukowska-Latallo et al., Efficient transfer of genetic material into mammalian cells using Starburst polyamidoamine dendrimers. Proc Natl Acad Sci USA. May 14, 1996;93(10):4897-902.

Langer, Perspectives and challenges in tissue engineering and regenerative medicine. Adv Mater. Sep. 4, 2009;21(32-33):3235-6.

Lee et al., Rapid pharmacokinetic and biodistribution studies using chlorotoxin-conjugated iron oxide nanoparticles: a novel non-radioactive method. PLoS One. Mar. 4, 2010;5(3):e9536. doi: 10.1371/journal.pone.0009536.

Lee et al., Stability and cellular uptake of polymerized siRNA (poly-siRNA)/polyethylenimine (PEI) complexes for efficient gene silencing. J Control Release. Feb. 15, 2010;141(3):339-46. Epub Oct. 14, 2009.

Lim, et al., A self-destroying polycationic polymer: biodegradable poly(4-hydroxy-l-proline ester. J. Am. Chem. Soc. 1999;121:5633-5639.

Luo et al., Synthetic DNA delivery systems. Nat Biotechnol. Jan. 2000;18(1):33-7. Review.

Lynn et al., Accelerated discovery of synthetic transfection vectors: parallel synthesis and screening of a degradable polymer library. J Am Chem Soc. Aug. 22, 2001;123(33):8155-6.

Lynn et al., Degradable Poly(β-amino esters): Synthesis, Characterization, and Self-Assembly with Plasmid DNA. J. Am. Chem. Soc. 2000;122 (44): 10761-8.

Lynn et al., pH-Responsive Polymer Microspheres: Rapid Release of Encapsulated Material within the Range of Intracellular pH. Angew Chem Int Ed Engl. May 4, 2001;40(9):1707-10.

Ma et al., Development of Cationic Polymer Coatings to Regulate Foreign Body Responses. Adv Mater. 2011;23:H189-94.

Margus et al., Cell-penetrating peptides as versatile vehicles for oligonucleotide delivery. Mol Ther. Mar. 2012;20(3):525-33. doi: 10.1038/mt.2011.284. Epub Jan. 10, 2012.

Martell et al., The Preparation and the Properties of Some N,N'-Disubstituted-ethylenediaminedipropionic Acids. J Am Chem Soc. 1950;72:5357-61.

Mendelsohn et al., Rational design of cytophilic and cytophobic polyelectrolyte multilayer thin films. Biomacromolecules. Jan.-Feb. 2003;4(1):96-106.

Miller, Cationic Liposomes for Gene Therapy. Angew. Chem. Int. Ed. 1998;37:1769-1785.

Mulligan, The basic science of gene therapy. Science. May 14, 1993;260(5110):926-32. Review.

Navarro et al., Phospholipid-polyethylenimine conjugate-based micelle-like nanoparticles for siRNA delivery. Drug Deliv and Trans Res. 2011; 25-33.

Neamnark et al., Aliphatic lipid substitution on 2 kDa polyethylenimine improves plasmid delivery and transgene expression. Mol Pharm. Nov.-Dec. 2009;6(6):1798-815.

Nguyen et al., A novel high-throughput cell-based method for integrated quantification of type I interferons and in vitro screening of immunostimulatory RNA drug delivery. Biotechnol Bioeng. Jul. 1, 2009;103(4):664-75.

Nguyen et al., Drug delivery-mediated control of RNA immunostimulation. Mol Ther. Sep. 2009;17(9):1555-62. Epub Jul. 7, 2009.

Novak et al., Biomimetic strategies based on viruses and bacteria for the development of immune evasive biomaterials. Biomaterials. Apr. 2009;30(11):1989-2005. Epub Jan. 29, 2009.

Novobrantseva et al., Systemic RNAi-mediated Gene Silencing in Nonhuman Primate and Rodent Myeloid Cells. Mol Ther Nucleic Acids. Jan. 24, 2012;1:e4. doi: 10.1038/mtna.2011.3.

Onuki et al., A review of the biocompatibility of implantable devices: current challenges to overcome foreign body response. J Diabetes Sci Technol. Nov. 2008;2(6):1003-15.

Orive et al., Cell encapsulation: promise and progress. Nat Med. Jan. 2003;9(1):104-7.

Ostuni et al., A Survey of Structure-Property Relationships of Surfaces that Resist the Adsorption of Protein . Langmuir. 2001;17:5605-20.

Paul et al., Topographical control of human macrophages by a regularly microstructured polyvinylidene fluoride surface. Biomaterials. Oct. 2008;29(30):4056-64. Epub Jul. 29, 2008.

Peppas et al., Hydrogels in Biology and Medicine: From Molecular Principles to Bionanotechnology. Mater. 2006;18:1345-60.

Philipp et al., Hydrophobically modified oligoethylenimines as highly efficient transfection agents for siRNA delivery. Bioconjug Chem. Nov. 2009;20(11):2055-61.

Phillips et al., Enhanced antibody response to liposome-associated protein antigens: preferential stimulation of IgG2a/b production. Vaccine. 1992;10(3):151-8.

Pollard et al., Ether amino alcohols. II. J Org Chem. 1952;17:1-3.

Prata et al., Lipophilic peptides for gene delivery. Bioconjug Chem. Feb. 2008;19(2):418-20.

Putnam et al., Poly(4-hydroxy-l-proline ester): Low-Temperature Polycondensation and Plasmid DNA Complexation. Macromolecules 1999;32:3658-62.

Putnam, Polymers for gene delivery across length scales. Nat Mater. Jun. 2006;5(6):439-51.

Ratner et al., Biomaterials: where we have been and where we are going. Annu Rev Biomed Eng. 2004;6:41-75.

Ryng et al., Synthesis and Structure Elucidation of 5-Aminomethinimino-3-methyl-4-isoxazolecarboxylic Acid Phenylamides and Their Immunological Activity. Archiv der Pharmazie. Jan. 1, 1997;330(11):319-26.

Sahay et al., Endocytosis of nanomedicines. J Control Release. Aug. 3, 2010;145(3):182-95. Epub Mar. 10, 2010.

Sakiyama-Elbert et al., Functional Biomaterials: Design of Novel Biomaterials. Ann Rev Mater Res. 2001;31:183-201.

Saltzman, Chapter 19. Cell Interactions with Polymers. In: Principles of Tissue Engineering, 2d ed., 2000:221-35.

Sanford, The biolistic process. Trends Biotechnol. 1988;6:299-302.

Sato et al., Resolution of liver cirrhosis using vitamin A-coupled liposomes to deliver siRNA against a collagen-specific chaperone. Nat Biotechnol. Apr. 2008;26(4):431-42. doi: 10.1038/nbt1396. Epub Mar. 30, 2008.

(56) References Cited

OTHER PUBLICATIONS

Schaus et al., Highly Selective Hydrolytic Kinetic Resolution of Terminal Epoxides Catalyzed by Chiral (salen)CoIII Complexes. Practical Synthesis of Enantioenriched Terminal Epoxides and 1,2-Biols. J Am Chem Soc. 2002;124(7):1307-15.
Schutte et al., Cytokine profiling using monocytes/macrophages cultured on common biomaterials with a range of surface chemistries. J Biomed Mater Res A. Jan. 2009;88(1):128-39.
Shchori, Poly(secondary Amine)s from Diacrylates and Diamines. J Polym Sci Polymer. Jun. 1983;21(6):413-15.
Sioud, Induction of inflammatory cytokines and interferon responses by double-stranded and single-stranded siRNAs is sequence-dependent and requires endosomal localization. J Mol Biol. May 20, 2005;348(5):1079-90. Epub Mar. 22, 2005.
Staubli et al., Hydrolytically degradable amino acid containing polymers. J Am Chem Soc. 1990;45:4419-24.
Steinman et al., Taking dendritic cells into medicine. Nature. Sep. 27, 2007;449(7161):419-26.
Suh et al., Ionization of Poly(ethylenimine) and Poly(allylamine) at Various PHS. Bioorg Chem. 1994;22:318-27.
Swali et al., Solid-Phase Dendrimer Synthesis and the Generation of Super-High-Loading Resin Beads for Combinatorial Chemistry. J Org Chem Am Chem Soc. 1997;62:4902-03.
Tarcha et al., Synthesis and characterization of chemically condensed oligoethylenimine containing beta-aminopropionamide linkages for siRNA delivery. Biomaterials. Sep. 2007;28(25):3731-40. Epub May 3, 2007.
Thompson et al., Antiamebic action of 5-chloro-7-diethylaminomethyl-8-quinolinol and of other substituted 8-quinolinols in vitro and in experimental animals. Am J Trop Med Hyg. Mar. 1955;4(2):224-48.
Tsvetkov et al., [Neoglycoconjugates based on dendrimeric poly(aminoamides)]. Bioorg Khim. Nov.-Dec. 2002;28(6):518-34. Russian. Published in English in Russian Journal of Bioorganic Chemistry, 2002;28(6):470-86.
Urban-Klein et al., RNAi-mediated gene-targeting through systemic application of polyethylenimine (PEI)-complexed siRNA in vivo. Gene Ther. Mar. 2005;12(5):461-6.
Van De Wetering et al., Structure-activity relationships of water-soluble cationic methacrylate/methacrylamide polymers for nonviral gene delivery. Bioconjug Chem. Jul.-Aug. 1999;10(4):589-97.
Van Dijkhuizen-Radersma et al., Bio compatibility and degradation of poly(ether-ester) microspheres: in vitro and in vivo evaluation. Biomaterials. Dec. 2002;23(24):4719-29.
Vandenbroucke et al., Prolonged gene silencing in hepatoma cells and primary hepatocytes after small interfering RNA delivery with biodegradable poly(beta-amino esters). J Gene Med. Jul. 2008;10(7):783-94.
Von Harpe et al., Characterization of commercially available and synthesized polyethylenimines for gene delivery. J Control Release. Nov. 3, 2000;69(2):309-22.
Ward, A Review of the Foreign-body Response to Subcutaneously-implanted Devices: The Role of Macrophages and Cytokines in Biofouling and Fibrosis. J Diabetes Sci Technol. 2008;2:768-77.
Werth et al., A low molecular weight fraction of polyethylenimine (PEI) displays increased transfection efficiency of DNA and siRNA in fresh or lyophilized complexes. J Control Release. May 15, 2006;112(2):257-70. Epub Mar. 6, 2006.
White et al., Poly(hydroxyaminoethers): A New Family of Epoxy-Based Thermoplastics. Adv Mater. 2000;12:1791-1800.
White et al., Step-growth polymerization of 10,11-epoxyundecanoic acid. Synthesis and properties of a new hydroxy-functionalized thermopastic polyester. Adv Mater. 2007;48:3990-98.
Whitehead et al., In vitro-in vivo translation of lipid nanoparticles for hepatocellular siRNA delivery. ACS Nano. Aug. 28, 2012;6(8):6922-9. doi: 10.1021/nn301922x. Epub Jul. 6, 2012.
Williams, On the mechanisms of biocompatibility. Biomaterials. Jul. 2008;29(20):2941-53 Epub Apr. 28, 2008.

Wintermantel et al., Blocked polyurethane prepolymers as component A in reactive adhesives. STN International HCAPLUS Database. 2006. Accession No. 2006:215601.
Yoshioka et al., Epoxy-based Electroactive Polymer Gels. Experimental Mechanics. 2002;42:404-08.
Zagridullin et al., Monobasic amines. II. Cycloalkylation and hydroxyalkylation of cyclic and acyclic di- and polyamines.. Zhurnal Organicheskoi Khimii. 1990;26(1):184-88. Russian.
Zauner et al., Polylysine-based transfection systems utilizing receptor-mediated delivery. Adv Drug Deliv Rev. Mar. 2, 1998;30(1-3):97-113.
Zhang et al., Ionization behavior of amino lipids for siRNA delivery: determination of ionization constants, SAR, and the impact of lipid pKa on cationic lipid-biomembrane interactions. Langmuir. Mar. 1, 2011;27(5):1907-14. doi: 10.1021/la104590k. Epub Jan. 20, 2011.
Zintchenko et al., Simple modifications of branched PEI lead to highly efficient siRNA carriers with low toxicity. Bioconjug Chem. Jul. 2008;19(7):1448-55. Epub Jun. 14, 2008.
International Search Report and Written Opinion for PCT/US2014/036355, mailed Aug. 5, 2014.
Chiang et al., Synthesis, characterization and properties of novel self-extinguishing organic-inorganic nanocomposites containing nitrogen, silicon and phosphorus via sol-gel method. Composite Science and Technology. 2008;68(14):2849-57.
Gupta et al., A review of in vitro-in vivo investigations on dendrimers: the novel nanoscopic drug carriers. Nanomedicine. Jun. 2006;2(2):66-73.
Anderson et al., Nanoliter-scale synthesis of arrayed biomaterials and application to human embryonic stem cells. Nat. Biotechnol. Jul. 2004;22(7):863-6. Epub Jun. 13, 2004.
Astle et al., A VEGFR2 Antagonist and Other Peptoids Evade Immune Recognition. Int J Pept Res Ther. 2008;14(3):223-227.
Bartel, MicroRNAs: Genomics, Biogenesis, Mechanism, and Function. Cell. 2004;116:281-97.
Bossle et al., Synthesis and biological activity of new 2-substituted analogs of fluphenazine. J Med Chem. Mar. 1, 1976;19(3):370-3.
Bratlie et al., Rapid biocompatibility analysis of materials via in vivo fluorescence imaging of mouse models. PLoS One. Apr. 6, 2010;5(4):e10032.
Carter et al., Mechanobiology of skeletal regeneration. Clin Orthop Relat Res. Oct. 1998;(355 Suppl):S41-55.
Chan et al., Triplex DNA: fundamentals, advances, and potential applications for gene therapy. J Mol Med. Apr. 1997;75(4):267-82. Review.
Conley et al., Derivation, propagation and differentiation of human embryonic stem cells. Int J Biochem Cell Biol. Apr. 2004;36(4):555-67.
Crooke, Molecular mechanisms of action of antisense drugs. Biochim Biophys Acta. Dec. 10, 1999;1489(1):31-44. Review.
Dern et al., Toxicity studies of pyrimethamine (daraprim). Am J Trop Med Hyg. Mar. 1955;4(2):217-20.
Diebold et al., Innate antiviral responses by means of TLR7-mediated recognition of single-stranded Rna. Science. Mar. 5, 2004;303(5663):1529-31. Epub Feb. 19, 2004.
Elbashir et al., Duplexes of 21-nucleotide RNAs mediate RNA interference in cultured mammalian cells. Nature. May 24, 2001;411(6836):494-8.
Frank-Kamenetsky et al., Therapeutic RNAi targeting PCSK9 acutely lowers plasma cholesterol in rodents and LDL cholesterol in nonhuman primates. Proc Natl Acad Sci U S A. Aug. 19, 2008;105(33):11915-20. doi: 10.1073/pnas.0805434105. Epub Aug. 11, 2008.
Geissmann et al., Development of monocytes, macrophages, and dendritic cells. Science. Feb. 5, 2010;327(5966):656-61. doi: 10.1126/science.1178331.
Giuliani et al., Beyond natural antimicrobial peptides: multimeric peptides and other peptidomimetic approaches. Cell Mol Life Sci. Jul. 2011;68(13):2255-66. doi: 10.1007/s00018-011-0717-3. Epub May 20, 2011.
Gross et al., Bioluminescence imaging of myeloperoxidase activity in vivo. Nat Med. Apr. 2009;15(4):455-61. Epub Mar. 22, 2009.

(56) References Cited

OTHER PUBLICATIONS

Guan et al., Surface photo-grafting of polyurethane with 2-hydroxyethyl acrylate for promotion of human endothelial cell adhesion and growth. J Biomater Sci Polym Ed. 2000;11(5):523-36.
Hemmi et al., Small anti-viral compounds activate immune cells via the TLR7 MyD88-dependent signaling pathway. Nat Immunol. Feb. 2002;3(2):196-200. Epub Jan. 22, 2002.
Hoekenga, The treatment of malaria with hydrochloroquine. Am J Trop Med Hyg. Mar. 1955;4(2): 221-3.
Hornung et al., Sequence-specific potent induction of IFN-alpha by short interfering RNA in plasmacytoid dendritic cells through TLR7. Nat Med. Mar. 2005;11(3):263-70. Epub Feb. 20, 2005.
Huang et al., Claudin-3 gene silencing with siRNA suppresses ovarian tumor growth and metastasis. Proc Natl Acad Sci U S A. Mar. 3, 2009;106(9):3426-30. doi: 10.1073/pnas.0813348106. Epub Feb. 10, 2009.
Ikeda et al., Role of micafungin in the antifungal armamentarium. Curr Med Chem. 2007;14(11):1263-75.
Jarrossay et al., Specialization and complementarity in microbial molecule recognition by human myeloid and plasmacytoid dendritic cells. Eur J Immunol. Nov. 2001;31(11):3388-93.
John et al., Effective RNAi-mediated gene silencing without interruption of the endogenous microRNA pathway. Nature. Oct. 11, 2007;449(7163):745-7. Epub Sep. 26, 2007.
Judge et al., Design of noninflammatory synthetic siRNA mediating potent gene silencing in vivo. Mol Ther. Mar. 2006;13(3):494-505. Epub Dec. 15, 2005.
Kaufman et al., Hematopoietic colony-forming cells derived from human embryonic stem cells. Proc Natl Acad Sci U S A. Sep. 11, 2001;98(19):10716-21. Epub Sep. 4, 2001.
Krieg, The toll of too much TLR7. Immunity. Nov. 2007;27(5):695-7.
Lan et al., Stabilized immune modulatory RNA compounds as agonists of Toll-like receptors 7 and 8. Proc Natl Acad Sci U S A. Aug. 21, 2007;104(34):13750-5. Epub Aug. 14, 2007.
Levenberg et al., Differentiation of human embryonic stem cells on three-dimensional polymer scaffolds. Proc Natl Acad Sci U S A. Oct. 18, 2003;100(22):12741-6. Epub Oct. 15, 2003.
Li et al., Reverse Atom Transfer Radical Polymerization in Miniemulsion. Macromolecules. 2003;36(16):6028-6035.
Lyle et al., Cytokeratin 15 (K15) as an Epithelial Stem Cell Marker: Implications for Aging and Carcinogenesis. J Invest Derma. 1999;112(4):623. Abstract #606.
Marshak-Rothstein, Toll-like receptors in systemic autoimmune disease. Nat Rev Immunol. Nov. 2006;6(11):823-35.
Mattey et al., Demonstration of cytokeratin in endothelial cells of the synovial microvasculature in situ and in vitro. Br J Rheumatol. Aug. 1993;32(8):676-82.
Moll, [Cytokeratins as markers of differentiation. Expression profiled in epithelia and epithelial tumors] Veroff Pathil. 1993;142:1-197. German.
Morrissey et al., Potent and persistent in vivo anti-HBV activity of chemically modified siRNAs. Nat Biotechnol. Aug. 2005;23(8):1002-7. Epub Jul. 24, 2005.
Nahrendorf et al., Dual channel optical tomographic imaging of leukocyte recruitment and protease activity in the healing myocardial infarct. Circ Res. Apr. 27, 2007;100(8):1218-25. Epub Mar. 22, 2007.
Nolan et al., Quantification of mRNA using real-time RT-PCR. Nat Protoc. 2006;1(3):1559-82.
Odorico et al., Multilineage differentiation from human embryonic stem cell lines. Stem Cells. 2001;19(3):193-204.
Pashine et al., Targeting the innate immune response with improved vaccine adjuvants. Nat Med. Apr. 2005;11(4 Suppl):S63-8.
Pera et al., Human embryonic stem cells. J Cell Sci. Jan. 2000;113 ( Pt 1):5-10.
Robbins et al., siRNA and innate immunity. Oligonucleotides. Jun. 2009;19(2):89-102.
Sawaf et al., [Cytokeratins, markers of epithelial cell differentiation: expression in normal epithelia.] Pathol Biol (Paris). 1992;40:655-65. French.
Schuldiner et al., Effects of eight growth factors on the differentiation of cells derived from human embryonic stem cells. Proc Natl Acad Sci U S A. Oct. 10, 2000;97(21):11307-12.
Schweizer et al., Synthetic Studies towards the Total Synthesis of Providencin. Synthesis. 2007;24:3807-14.
Spradling et al., Stem cells find their niche. Nature. Nov. 1, 2001;414(6859):98-104.
Streuli, Extracellular matrix remodeling and cellular differentiation. Curr Opin Cell Biol. 1999;11:634-40.
Tabara et al., The rde-1 Gene, RNA Interference, and Transposon Silencing in C. elegans. Cell. 1999;99:123-32.
Tang et al., In vitro gene delivery by degraded polyamidoamine dendrimers. Bioconjug Chem. Nov.-Dec. 1996;7(6):703-14.
Thomson et al., Embryonic stem cell lines derived from human blastocysts. Science. Nov. 6, 1998;282(5391):1145-7.
Unkeless et al., Structure and function of human and murine receptors for IgG. Annu Rev Immunol. 1988;6:251-81.
Wang et al., The functions of microRNAs in plants. Front Biosci. 2007;12:3975-82.
Wilen et al., Strategies in Optical Resolutions. Tetrahedron. 1977;33:2725-36.
Wobus, Potential of embryonic stem cells. Mol Aspects Med. Jun. 2001;22(3):149-64.
Yaffee et al., Serial passaging and differentiation of myogenic cells isolated from dystrophic mouse muscle. Nature. 1977;270:725-27.
Zhang et al., Human Toll-like receptor-dependent induction of interferons in protective immunity to viruses. Immunol Rev. Dec. 2007;220:225-36.

* cited by examiner

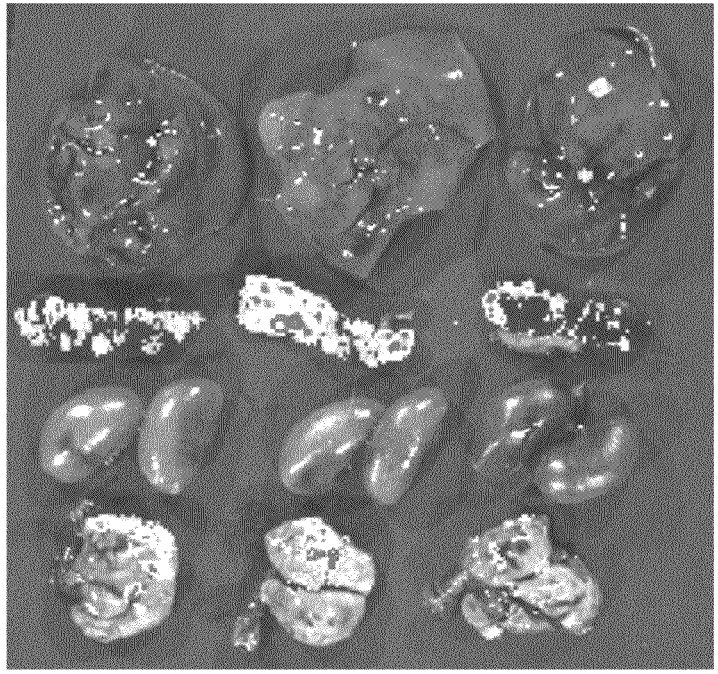
I-3 (1.25 mg/kg)  Figure 6B
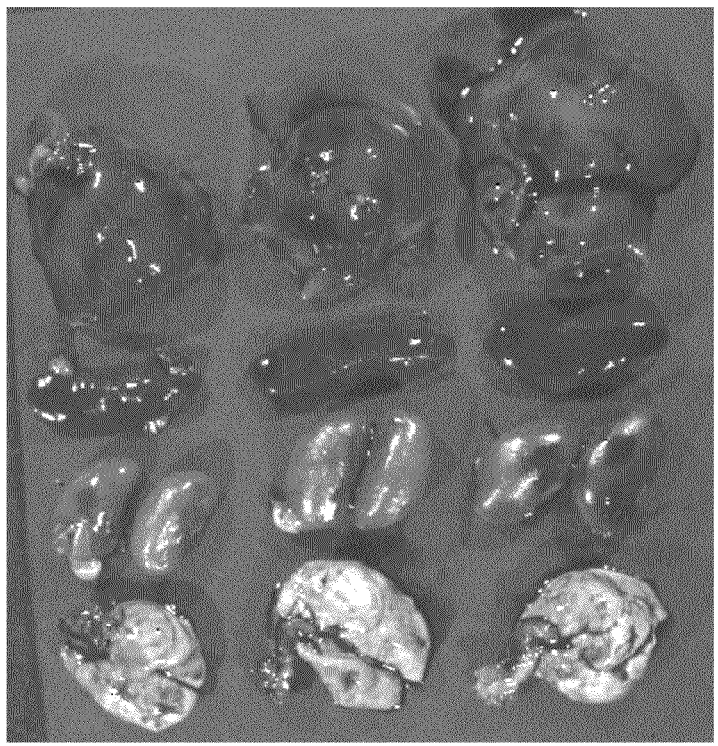
PBS  Figure 6A

1,3,5-TRIAZINANE-2,4,6-TRIONE DERIVATIVES AND USES THEREOF

RELATED APPLICATIONS

The present application claims priority under 35 U.S.C. §119(e) to U.S. provisional patent application, U.S. Ser. No. 61/818,295, filed May 1, 2013, which is incorporated herein by reference.

GOVERNMENT SUPPORT

This invention was made with U.S. Government support under Grant No. R37 EB000244 awarded by the National Institutes of Health. The U.S. government has certain rights in this invention.

BACKGROUND OF THE INVENTION

The ability to silence genes via RNA interference (RNAi) was reported by Mello and Fire in 1998. See Fire et al., *Nature* (1998) 391:806-811. Since then, scientists have rushed to take advantage of the enormous therapeutic potential driven by targeted gene knockdown. This is evidenced by the fact that the first report of small interfering RNA (siRNA) mediated RNAi in human beings was reported only twelve years after the phenomenon was described in *Caenorhabditis elegans*. See Davis et al., *Nature* (2010) 464:1067-1070. The advantages of siRNA therapeutics include high target selectivity and specificity, and the potential to target pathways currently believed to be "undruggable" for the treatment of genetic diseases without effective therapy. siRNA therapeutics has shown promising results for the treatment of various diseases, such as hepatic carcinoma, hypercholesterolemia, refractory anemia, and familial amyloid neuropathy.

However, the efficient delivery of siRNA is still a challenge in the development of siRNA therapeutics. Due to issues associated with delivery efficiency and toxicity, the clinical use of siRNA requires safer and more effective delivery systems. It is understood that the development of genetic drugs is slowed by the inability to deliver nucleic acids effectively in vivo. When unprotected, genetic materials injected into the bloodstream can be degraded by deoxyribonucleases (DNAases) and ribonucleases (RNAases), or, if not degraded, the genetic materials can stimulate an immune response. See, e.g., Whitehead et al., *Nature Reviews Drug Discovery* (2009) 8:129-138; Robbins et al., *Oligonucleotides* (2009) 19:89-102. Intact siRNA must then enter the cytosol, where the antisense strand is incorporated into the RNA-induced silencing complex (RISC) (Whitehead et al., supra). The RISC associates with and degrades complementary mRNA sequences, thereby preventing translation of the target mRNA into protein, i.e., "silencing" the gene.

To overcome difficulties in delivery, polynucleotides have been complexed with a wide variety of delivery systems, including polymers, lipids, inorganic nanoparticles, and viruses. See, e.g., Peer et al. *Nature Nanotechnology*, (2007) 2:751-760. However, despite promising data from ongoing clinical trials for the treatment of respiratory syncytial virus and liver cancers (see, e.g., Zamora et al., *Am. J. Respir. Crit. Care Med.* (2011) 183:531-538), the clinical use of siRNA continues to require development of safer and more effective delivery systems. Toward this end, numerous lipid-like molecules have been developed including poly β-amino esters and amino alcohol lipids. See, e.g., international PCT Patent Application Publications, WO 2002/031025, WO 2004/106411, WO 2008/011561, WO 2007/143659, WO 2006/138380, and WO 2010/053572. Amino acid, peptide, polypeptide-lipids have also been studied for a variety of applications, including use as therapeutics, biosurfactants, and nucleotide delivery systems. See, e.g., Giuliani et al., *Cellular and Molecular Life Sciences* (2011) 68:2255-2266; Ikeda et al., *Current Medicinal Chemistry* (2007) 14: 111263-1275; Sen, *Advances in Experimental Medicine and Biology* (2010) 672:316-323; and Damen et al., *Journal of Controlled Release* (2010) 145:33-39. However, there continues to remain a need to investigate and develop new and improved polynucleotide delivery systems, such as ones that are more efficient and/or less toxic than existing systems.

SUMMARY OF THE INVENTION

The present invention provides novel 1,3,5-triazinane-2,4,6-trione derivatives and uses thereof. Also provided are compositions (e.g., pharmaceutical compositions) including a compound of the invention and an agent (e.g., an siRNA, mRNA, or plasmid DNA). The present invention also provides methods and kits using the compositions for delivering an agent to a subject (e.g., to the liver, spleen, or lung of the subject) or cell and for treating and/or preventing a range of diseases, such as genetic diseases, proliferative disease, hematological diseases, neurological diseases, liver diseases, spleen diseases, and lung diseases.

In one aspect, the invention provides compounds of Formula (I):

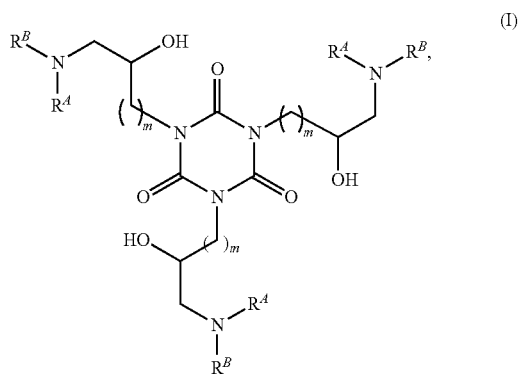

and salts thereof, wherein $R^A$, $R^B$, and m are as described herein.

Exemplary compounds of Formula (I) include, but are not limited to:

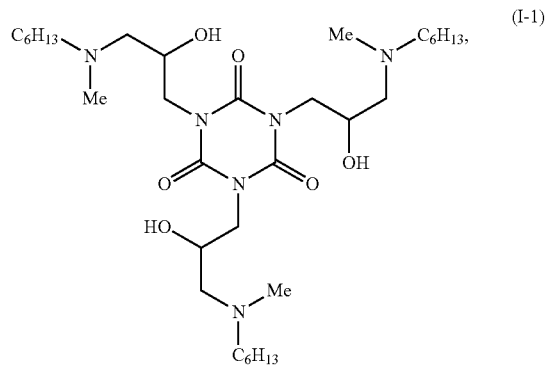

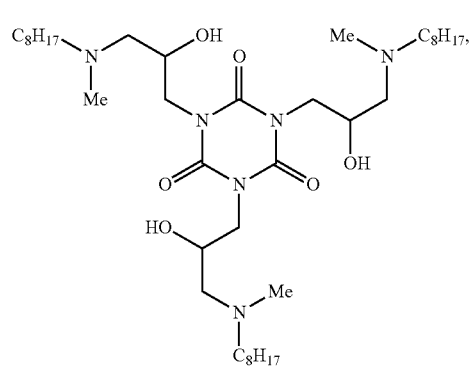
(I-2)
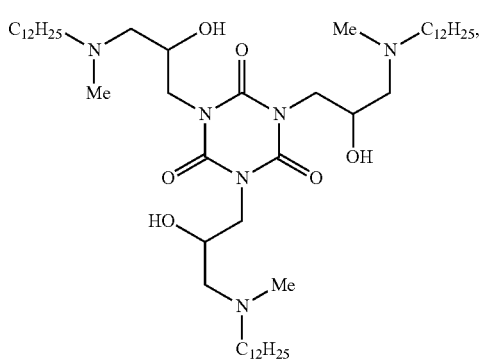
(I-3)
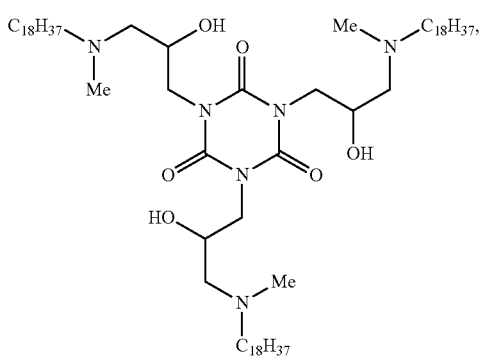
(I-4)
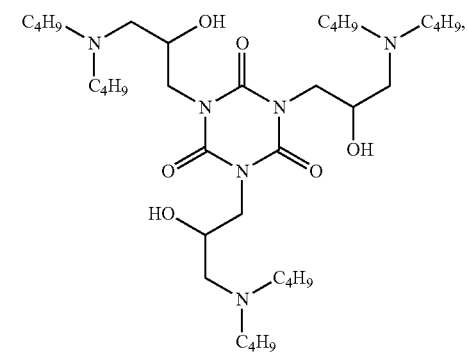
(I-5)
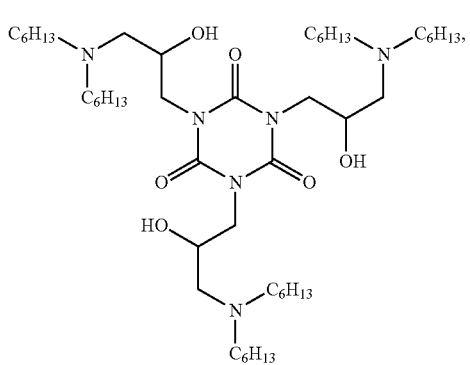
(I-6)
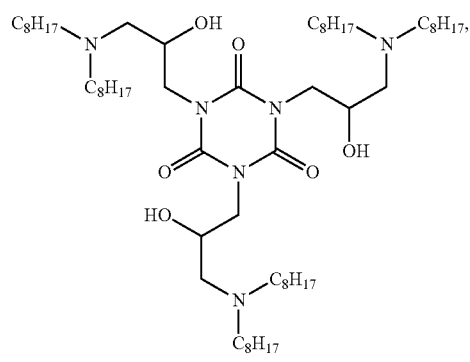
(I-7)
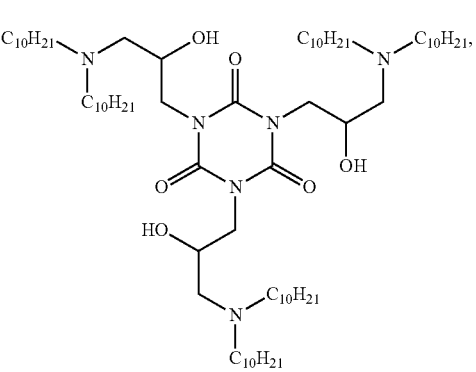
(I-8)
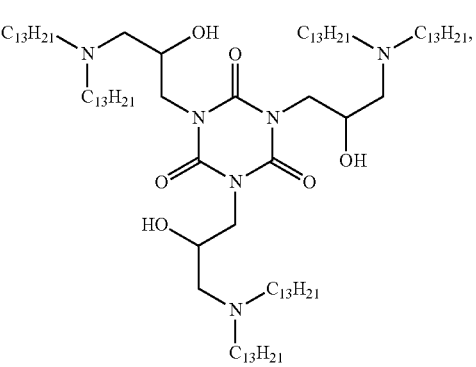
(I-9)
and salts thereof.

In another aspect, the invention provides compounds of Formula (II):

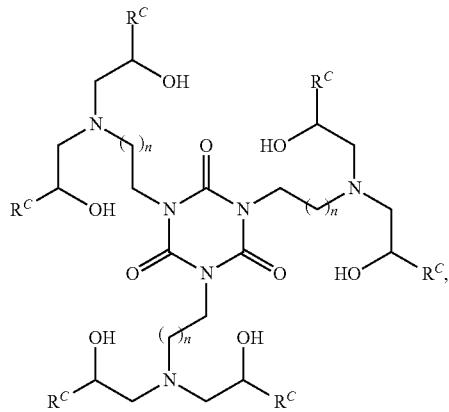

and salts thereof, wherein $R^C$ and n are as described herein.

In yet another aspect, the present invention provides compositions (e.g., pharmaceutical compositions) comprising a compound of the invention, an agent (e.g., an agent, such as a polynucleotide), and optionally an excipient (e.g., a pharmaceutically acceptable excipient). Without wishing to be bound by any particular theory, the inventive compositions are thought to be useful for delivering the agent to a subject (e.g., to the liver, spleen, or lung of the subject) or cell. Without wishing to be bound by any particular theory, a compound of the invention, which includes more than one amino moiety that may be protonated to form positively charged ammonium cations, may bind to an agent that includes negatively charged moieties, such as a polynucleotide, to form a complex. A compound of the invention also typically includes more than one unsubstituted or substituted alkyl moiety, which is hydrophobic and may assist the inventive compound and/or the complex of the inventive compound and the agent to pass through cell membranes or be taken up by cells.

The compositions of the invention (e.g., pharmaceutical compositions) may also be useful in treating and/or preventing a range of diseases (e.g., genetic diseases, proliferative diseases, hematological diseases, neurological diseases, liver diseases, spleen diseases, and lung diseases) in a subject in need thereof. In certain embodiments, a composition of the invention includes an effective amount of the agent. The inventive compositions may also be useful in treating and/or preventing a disease, such as a genetic disease, a proliferative disease, a hematological disease, a neurological disease, a liver disease, a spleen disease, or a lung disease. In certain embodiments, the inventive compositions are useful in treating and/or preventing hepatic carcinoma, hypercholesterolemia, refractory anemia, or familial amyloid neuropathy.

Another aspect of the present invention relates to methods of delivering an agent to a subject (e.g., to the liver, spleen, or lung of the subject) or cell.

In certain embodiments, the method of delivering an agent comprises administering a composition of the invention to the subject or cell.

Another aspect of the invention relates to methods of increasing the exposure of an agent to a subject or cell.

Another aspect of the invention relates to methods of increasing the concentration of an agent in a subject or cell.

In another aspect, the present invention provides methods of treating and/or preventing a disease, such as a genetic disease, a proliferative disease, a hematological disease, a neurological disease, a liver disease, a spleen disease, or a lung disease in a subject in need thereof. In certain embodiments, the disease that is treated and/or prevented by the inventive methods is hepatic carcinoma, hypercholesterolemia, refractory anemia, or familial amyloid neuropathy. In certain embodiments, the method of treating and/or preventing a disease comprises administering a composition of the invention to the subject.

Another aspect of the invention relates to methods of screening a library of compounds to identify one or more compounds that are useful in the methods of the invention. The compound identified by the methods of screening may be useful for delivering an agent (e.g., a polynucleotide) to a subject (e.g., to the liver, spleen, or lung of the subject) or cell. The compound identified by the methods of screening may also be useful in treating and/or preventing a disease described herein.

In yet another aspect, the present invention provides compositions described herein for use in delivering an agent to a subject (e.g., to the liver, spleen, or lung of the subject) or cell.

In still another aspect, the present invention provides compositions described herein for use in treating and/or preventing a disease described herein in a subject in need thereof.

Another aspect of the present invention relates to methods of preparing compounds of Formula (I), and salts thereof, by a nucleophilic reaction of a primary or secondary amine with an 1,3,5-triazinane-2,4,6-trione derivative substituted with three epoxide moieties. In certain embodiments, the methods of preparing compounds of Formula (I) include reacting a compound of Formula (A), or a salt thereof, with a compound of Formula (B), or a salt thereof, to provide a compound of Formula (I), or a salt thereof:

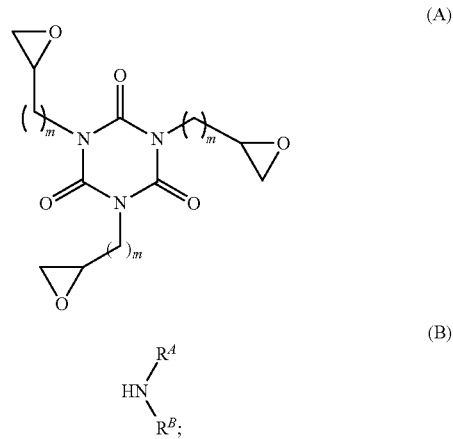

wherein $R^A$, $R^B$, and m are as described herein.

In another aspect, the present invention provides methods of preparing compounds of Formula (II), and salts thereof, by an electrophilic reaction of a substituted epoxide with an 1,3,5-triazinane-2,4,6-trione derivative substituted with three primary amino moieties. In certain embodiments, the methods of preparing compounds of Formula (II) include reacting a compound of Formula (C), or a salt thereof, with a compound of Formula (D), or a salt thereof, to provide a compound of Formula (II), or a salt thereof:

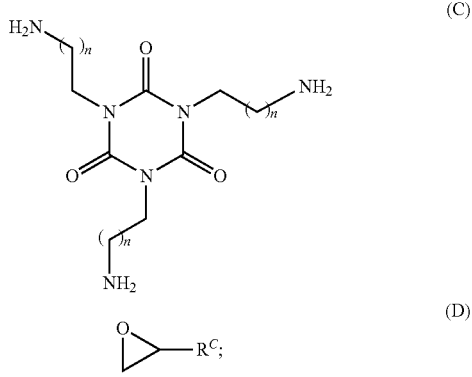

(C) and (D) structures wherein $R^C$ and n are as described herein.

Another aspect of the present invention relates to kits comprising a container with a composition of the invention. The kits of the invention may include a single dose or multiple doses of the composition. The provided kits may be useful in delivering an agent to a subject (e.g., to the liver, spleen, or lung of the subject) or cell. The provided kits may also be useful in in treating and/or preventing a disease described herein in a subject in need thereof. In certain embodiments, the kits further include instructions for administering the composition to the subject.

The details of one or more embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated ("heterocycloalkyl") or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinolizinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-5}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, t-butyloxycarbonyl (BOC or Boc), methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, the term "lipophilic" or "hydrophobic" refers to the ability of a compound to dissolve, or the ability of a moiety of a compound to assist the compound in dissolving in fats, oils, lipids, and/or non-polar solvents (e.g., hexane or toluene). Lipophilic moieties include, but are not limited to, substituted or unsubstituted, branched or unbranched alkyl groups having 1 to 50 carbon atoms. In certain embodiments, the lipophilic moiety is an alkyl group including at least 1, at least 6, at least 12, at least 18, at least 24, at least 36, or at least 50 carbon atoms. In certain embodiments, the lipophilic moiety is an alkyl group including at most 50, at most 36, at most 24, at most 18, at most 12, or at most 6 carbon atoms. Combinations of the above-referenced ranges (e.g., at least about 1 and at most about 24 carbon atoms) are also within the scope of the invention. In certain embodiments, the lipophilic moiety is unsubstituted alkyl. In certain embodiments, the lipophilic moiety is unsubstituted and unbranched alkyl. In certain embodiments, the lipophilic moiety is unsubstituted and unbranched $C_{1-24}$ alkyl. In certain embodiments, the lipophilic moiety is unsubstituted and unbranched $C_{6-24}$ alkyl. In certain embodiments, the lipophilic moiety is unsubstituted and unbranched $C_{12-24}$ alkyl.

As used herein, the term "small organic molecule" or "small molecule" refers to an organic molecule with a molecular weight of 1,000 g/mol or less. In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as an "small organometallic molecule."

As used herein, a "large organic molecule" or "large molecule" refers to an organic compound with a molecular weight of greater than about 1,000 g/mol. In certain embodiments, the molecular weight of a large molecule is greater than about 2,000 g/mol, greater than about 3,000 g/mol, greater than about 4,000 g/mol, or greater than about 5,000 g/mol. In certain embodiments, the molecular weight of a large molecule is at most about 100,000 g/mol, at most about 30,000 g/mol, at most about 10,000 g/mol, at most about 5,000 g/mol, or at most about 2,000 g/mol. Combinations of the above ranges (e.g., greater than about 2,000 g/mol and at most about 10,000 g/mol) are also possible. In certain embodiments, the large molecule is a therapeutically active agent such as a drug (e.g., a molecule approved by the U.S. Food and Drug Administration as provided in the Code of Federal Regulations (C.F.R.)). The large molecule may also be complexed with one or more metal atoms and/or metal ions. In this instance, the large molecule is also referred to as an "large organometallic compound."

A "protein," "peptide," or "polypeptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "apolipoprotein" refers to a protein that binds a lipid (e.g., triacylglycerol or cholesterol) to form a lipoprotein. Apolipoproteins also serve as enzyme cofactors, receptor ligands, and lipid transfer carriers that regulate the metabolism of lipoproteins and their uptake in tissues. Major types of apolipoproteins include integral and non-integral apolipoproteins. Exemplary apolipoproteins include apoA (e.g., apoA-I, apoA-II, apoA-IV, and apoA-V); apoB (e.g., apoB48 and apoB 100); apoC (e.g., apoC-I, apoC-II, apoC-III, and apoC-IV); apoD; apoE; apoH; and apoJ.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), a provirus, a lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), a polyinosinic acid, a ribozyme, a flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., Nucl. Acids Res., 16, 3209, (1988), methylphosphonate oligonucleotides can be prepared by use of controlled pore glass polymer supports (Sarin et al., Proc. Natl. Acad. Sci. U.S.A. 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include, but are not limited to: the SV40 early promoter region (Bernoist et al., Nature, 290, 304-310, (1981); Yamamoto et al., Cell, 22, 787-797, (1980); Wagner et al., Proc. Natl. Acad. Sci. U.S.A. 78, 1441-1445, (1981); Brinster et al., Nature 296, 39-42, (1982)). Any type of plasmid, cosmid, yeast artificial chromosome or viral vector can be used to prepare the recombinant DNA construct that can be introduced directly into the tissue site. Alternatively, viral vectors can be used which selectively infect the desired tissue, in which case administration may be accomplished by another route (e.g., systemically).

The polynucleotides may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "recombinant nucleic acid molecule" is a nucleic acid molecule that has undergone a molecular biological manipulation, i.e., non-naturally occurring nucleic acid molecule or genetically engineered nucleic acid molecule. Furthermore, the term "recombinant DNA molecule" refers to a nucleic acid sequence which is not naturally occurring, or can be made by the artificial combination of two otherwise separated segments of nucleic acid sequence, i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., Molecular Cloning, second edition, Cold Spring Harbor Laboratory, Plainview, N.Y.; (1989), or Ausubel et al., Current Protocols in Molecular Biology, Current Protocols (1989), and DNA Cloning: A Practical Approach, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design. Examples of recombinant nucleic acid molecule include recombinant vectors, such as cloning or expression vectors which contain DNA sequences encoding Ror family proteins or immunoglobulin proteins which are in a 5' to 3' (sense) orientation or in a 3' to 5' (antisense) orientation.

The term "pDNA," "plasmid DNA," or "plasmid" refers to a small DNA molecule that is physically separate from, and can replicate independently of, chromosomal DNA within a cell. Plasmids can be found in all three major domains: Archaea, Bacteria, and Eukarya. In nature, plasmids carry genes that may benefit survival of the subject (e.g., antibiotic resistance) and can frequently be transmitted from one bacterium to another (even of another species) via horizontal gene transfer. Artificial plasmids are widely used as vectors in molecular cloning, serving to drive the replication of recombinant DNA sequences within host subjects. Plasmid sizes may vary from 1 to over 1,000 kbp. Plasmids are considered replicons, capable of replicating autonomously within a suitable host.

"RNA transcript" refers to the product resulting from RNA polymerase-catalyzed transcription of a DNA sequence. When the RNA transcript is a complementary copy of the DNA sequence, it is referred to as the primary transcript or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. The cDNA can be single-stranded or converted to double-stranded form using, for example, the Klenow fragment of DNA polymerase I.

A sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The terms "nucleic acid" or "nucleic acid sequence", "nucleic acid molecule", "nucleic acid fragment" or "polynucleotide" may be used interchangeably with "gene", "mRNA encoded by a gene" and "cDNA".

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "gene silencing" refers to an epigenetic process of gene regulation where a gene is "switched off" by a mechanism other than genetic modification. That is, a gene which would be expressed (i.e., "turned on") under normal circumstances is switched off by machinery in the cell. Gene silencing occurs when RNA is unable to make a protein during translation. Genes are regulated at either the transcriptional or post-transcriptional level. Transcriptional gene silencing is the result of histone modifications, creating an environment of heterochromatin around a gene that makes it inaccessible to transcriptional machinery (e.g., RNA polymerase and transcription factors). Post-transcriptional gene silencing is the result of mRNA of a particular gene being destroyed or blocked. The destruction of the mRNA prevents translation and thus the formation of a gene product (e.g., a protein). A common mechanism of post-transcriptional gene silencing is RNAi.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

As defined herein, the term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering," or "administration," as used herein, refers to implanting, absorbing, ingesting, injecting, inhaling, or otherwise introducing an inventive compound, or a composition thereof, in or on a subject.

As used herein, the terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

As used herein, the terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adrenoleukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

As used herein, the term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

As used herein, the term "inflammatory disease" or "inflammation" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigusvulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

As used herein, a "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as Pernicious Anemia, Hemorrhagic Anemia, Hemolytic Anemia, Aplastic Anemia, Sickle Cell Anemia, Sideroblastic Anemia, Anemia associated with chronic infections such as Malaria, Trypanosomiasis, HTV, Hepatitis virus or other viruses, Myelophthisic Anemias caused by marrow deficiencies, renal failure resulting from Anemia, Anemia, Polycethemia, Infectious Mononucleosis (EVI), Acute Non-Lymphocytic Leukemia (ANLL), Acute Myeloid Leukemia (AML), Acute Promyelocytic Leukemia (APL), Acute Myelomonocytic Leukemia (AMMoL), Polycethemia Vera, Lymphoma, Acute Lymphocytic Leukemia (ALL), Chronic Lymphocytic Leukemia, Wilm's Tumor, Ewing's Sarcoma, Retinoblastoma, Hemophilia, disorders associated with an increased risk of Thrombosis, Herpes, Thalessemia, antibody-mediated disorders such as transfusion reactions and Erythroblastosis, mechanical trauma to red blood cells such as micro-angiopathic hemolytic anemias, Thrombotic Thrombocytopenic Purpura and disseminated intravascular coagulation, infections by parasites such as *Plasmodium*, chemical injuries from, e.g., lead poisoning, and Hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases also refer to a type of neurological disease marked by the loss of nerve cells, including, but not limited to, Alzheimer's disease, Parkinson's disease, amyotrophic lateral sclerosis, tauopathies (including fronto-temporal dementia), and Huntington's disease. Examples of neurological diseases include, but are not limited to, headache, stupor and coma, dementia, seizure, sleep disorders, trauma, infections, neoplasms, neuroophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include Acquired Epileptiform Aphasia; Acute Disseminated Encephalomyelitis; Adrenoleukodystrophy; agenesis of the corpus callosum; Agnosia; Aicardi syndrome; Alexander disease; Alpers' disease; Alternating hemiplegia; Alzheimer's disease; Amyotrophic lateral sclerosis; anencephaly; Angelman syndrome; Angiomatosis; Anoxia; aphasia; apraxia; Arachnoid Cysts; Arachnoiditis; Arnold-Chiari malformation; Arteriovenous malformation; Asperger syndrome; Ataxia Telangiectasia; Attention Deficit Hyperactivity Disorder; autism; autonomic dysfunction; Back Pain; Batten disease; Behcet's disease; Bell's palsy; Benign Essential Blepharospasm; Benign Focal; Amyotrophy; Benign Intracranial Hypertension; Binswanger's disease; Blepharospasm; Bloch Sulzberger syndrome; Brachial plexus injury; Brain abscess; Brain injury; Brain tumors (including Glioblastoma multiforme); Spinal tumor; Brown-Sequard syndrome; Canavan disease; Carpal tunnel syndrome (CTS); Causalgia; Central pain syndrome; Central pontine myelinolysis; Cephalic disorder; Cerebral aneurysm; Cerebral arteriosclerosis; Cerebral atrophy; Cerebral gigantism; Cerebral palsy; Charcot-Marie-Tooth disease; Chemotherapy-induced neuropathy and neuropathic pain; Chiari malformation; Chorea; Chronic inflammatory demyelinating polyneuropathy (CIDP); Chronic pain; Chronic regional pain syndrome; Coffin Lowry syndrome; Coma, including Persistent Vegetative State; Congenital facial diplegia; Corticobasal degeneration; Cranial arteritis; Craniosynostosis; Creutzfeldt-Jakob disease; Cumulative trauma disorders; Cushing's syndrome; Cytomegalic inclusion body disease (CIBD); Cytomegalovirus Infection; Dancing eyes-dancing feet syndrome; Dandy-Walker syndrome; Dawson disease; De Morsier's syndrome; Dejerine-Klumpke palsy; Dementia; Dermatomyositis; Diabetic neuropathy; Diffuse sclerosis; Dysautonomia; Dysgraphia; Dyslexia; Dystonias; Early infantile epileptic encephalopathy; Empty sella syndrome; Encephalitis; Encephaloceles; Encephalotrigeminal angiomatosis; Epilepsy; Erb's palsy; Essential tremor; Fabry's disease; Fahr's syndrome; Fainting; Familial spastic paralysis; Febrile seizures; Fisher syndrome; Friedreich's ataxia; Fronto-Temporal Dementia and other "Tauopathies"; Gaucher's disease; Gerstmann's syndrome; Giant cell arteritis; Giant cell inclusion disease; Globoid cell Leukodystrophy; Guillain-Barre syndrome; HTLV-1 associated myelopathy; Hallervorden-Spatz disease; Head injury; Headache; Hemifacial Spasm; Hereditary Spastic Paraplegia; Heredopathia atactica polyneuritiformis; Herpes zoster oticus; Herpes zoster; Hirayama syndrome; HIV-Associated Dementia and Neuropathy (see also Neurological manifestations of AIDS); Holoprosencephaly; Huntington's disease and other polyglutamine repeat diseases; Hydranencephaly; Hydrocephalus; Hypercortisolism; Hypoxia; Immune-Mediated encephalomyelitis; Inclusion body myositis; Incontinentia pigmenti; Infantile; phytanic acid storage disease; Infantile Refsum disease; Infantile spasms; Inflammatory myopathy; Intracranial cyst; Intracranial hypertension; Joubert syndrome; Kearns-Sayre syndrome; Kennedy disease; Kinsbourne syndrome; Klippel Feil syndrome; Krabbe disease; Kugelberg-Welander disease; Kuru; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Lewy body dementia; Lissencephaly; Locked-In syndrome; Lou Gehrig's disease (aka Motor Neuron Disease or Amyotrophic Lateral Sclerosis); Lumbar disc disease; Lyme disease-Neurological Sequelae; Machado-Joseph disease; Macrencephaly; Megalencephaly; Melkersson-Rosenthal syndrome; Menieres disease; Meningitis; Menkes disease; Metachromatic leukodystrophy; Microcephaly; Migraine; Miller Fisher syndrome; Mini-Strokes; Mitochondrial Myopathies; Mobius syndrome; Monomelic amyotrophy; Motor Neurone Disease; Moyamoya disease; Mucopolysaccharidoses; Multi-Infarct Dementia; Multifocal motor neuropathy; Multiple sclerosis and other demyelinating disorders; Multiple system atrophy with postural hypotension; Muscular dystrophy; Myasthenia gravis; Myelinoclastic diffuse sclerosis; Myoclonic encephalopathy of infants; Myoclonus; Myopathy; Myotonia congenital; Narcolepsy; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Niemann-Pick disease; O'Sullivan-McLeod syndrome; Occipital Neuralgia; Occult Spinal Dysraphism Sequence; Ohtahara syndrome; Olivopontocerebellar Atrophy; Opsoclonus Myoclonus; Optic neuritis; Orthostatic Hypotension; Overuse syndrome; Paresthesia; Parkinson's disease; Paramyotonia Congenita; Paraneoplastic diseases; Paroxysmal attacks; Parry Romberg syndrome; Pelizaeus-Merzbacher disease; Periodic Paralyses; Peripheral Neuropathy; Painful Neuropathy and Neuropathic Pain; Persistent Vegetative State; Pervasive developmental disorders; Photic sneeze reflex; Phytanic Acid Storage disease; Pick's disease; Pinched Nerve; Pituitary Tumors; Polymyositis; Porencephaly; Post-Polio syndrome; Postherpetic Neuralgia (PHN); Postinfectious Encephalomyelitis; Postural Hypotension; Prader-Willi syndrome; Primary Lateral Sclerosis; Prion diseases; Progressive; Hemifacial Atrophy; Progressive multifocal leukoencephalopathy; Progressive Sclerosing Poliodystrophy; Progressive Supranuclear Palsy; Pseudotumor cerebri; Ramsay-Hunt syndrome (Type I and Type II); Rasmussen's Encephalitis; Reflex Sympathetic Dystrophy syndrome; Refsum disease; Repetitive Motion Disorders; Repetitive Stress Injuries; Restless Legs syndrome; Retrovirus-Associated Myelopathy; Rett syndrome; Reye's syndrome; Saint Vitus Dance; Sandhoff disease; Schilder's disease; Schizencephaly; Septo-Optic Dysplasia; Shaken Baby syndrome; Shingles; Shy-Drager syndrome; Sjogren's syndrome; Sleep Apnea; Soto's syndrome; Spasticity; Spina bifida; Spinal cord injury; Spinal cord tumors; Spinal Muscular Atrophy; Stiff-Person syndrome; Stroke; Sturge-Weber syndrome; Subacute Sclerosing Panencephalitis; Subarachnoid Hemorrhage; Subcortical Arteriosclerotic Encephalopathy; Sydenham Chorea; Syncope; Syringomyelia; Tardive dyskinesia; Tay-Sachs disease; Temporal arteritis; Tethered Spinal Cord syndrome; Thomsen disease; Thoracic Outlet syndrome; Tic Douloureux; Todd's Paralysis; Tourette syndrome; Transient ischemic attack; Transmissible Spongiform Encephalopathies; Transverse myelitis; Traumatic Brain injury; Tremor; Trigeminal Neuralgia; Tropical Spastic Paraparesis; Tuberous Sclerosis; Vascular Dementia (Multi-Infarct Dementia); Vasculitis including Temporal Arteritis; Von Hippel-Lindau Disease (VHL); Wallenberg's syndrome; Werdnig-Hoffman disease; West syndrome; Whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

BRIEF DESCRIPTION OF THE DRAWINGS

FIGS. 6A-6B show the expression of luciferase protein in mice (e.g., in the lung, kidney, spleen, and liver) treated with compound I-3 formulated luciferase plasmid DNA (FIG. 6B) compared to mice treated with PBS (FIG. 6A).

DETAILED DESCRIPTION OF CERTAIN EMBODIMENTS OF THE INVENTION

Figure 1:
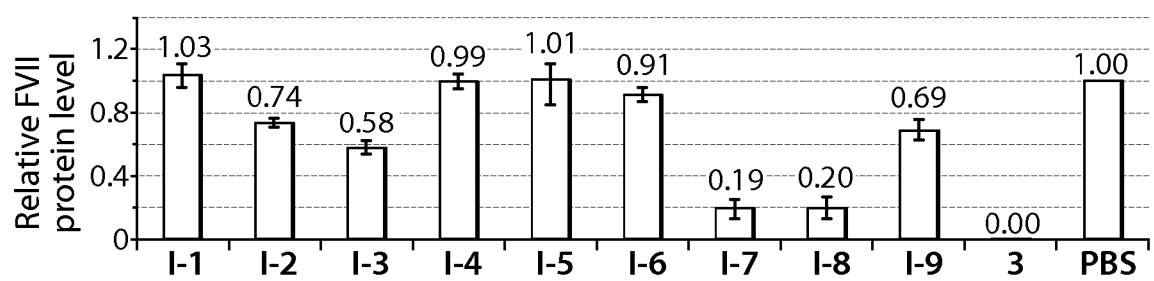
FIG. 1 shows the results of an in vivo liver gene silencing experiment. Compounds I-1 to I-9 were dosed in mice at about 1 mg/kg. Compound 3 was used as a positive control. Relative Factor VII (FVII) protein levels were measured 24 hours post dose.

The present invention provides novel 1,3,5-triazinane-2,4,6-trione derivatives and uses thereof (e.g. in drug delivery). In one aspect, the invention provides compounds of Formula (I), and salts thereof. In another aspect, the invention provides compounds of Formula (II), and salts thereof. Also provided in the present invention are compositions including a compound of the invention and an agent. The compositions have been found to be able to deliver effectively and efficiently the agent to a subject or cell. A compound of the invention, which includes more than one amino moiety that may be protonated to form a positively charged ammonium cation, may bind to an agent (e.g., a polynucleotide, such as an siRNA, mRNA, or plasmid DNA) that includes negatively charged moieties to form a complex. A compound of the invention also typically include more than one unsubstituted or substituted alkyl moiety, which are hydrophobic and may assist the inventive compound and/or the complex of the inventive compound and the agent to pass through cell membranes and/or mask the charge on the agent to be delivered. In certain embodiments, the inventive compositions are useful in delivering the agent selectively to a particular tissue or organ (e.g., the liver, spleen, or lung) of the subject. The compositions of the invention (e.g., pharmaceutical compositions) may also be useful in treating and/or preventing a range of diseases (e.g., genetic diseases, proliferative diseases, hematological diseases, neurological diseases, liver diseases, spleen diseases, and lung diseases) in a subject in need thereof.

Compounds

In one aspect, the present invention provides compounds of Formula (I):

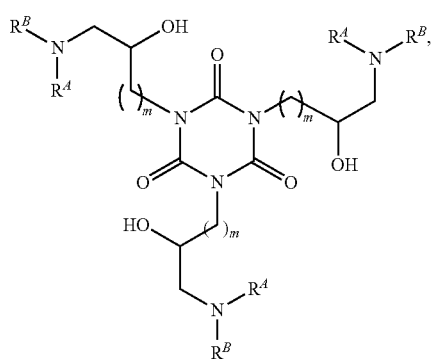

and salts thereof;
wherein:

each instance of $R^A$ is independently hydrogen or substituted or unsubstituted alkyl;

each instance of $R^B$ is independently substituted or unsubstituted alkyl; and each instance of m is independently 1, 2, 3, 4, 5, or 6.

In certain embodiments, provided are compounds of Formula (I), and pharmaceutically acceptable salts thereof.

In certain embodiments, the compound of Formula (I) is of the formula:

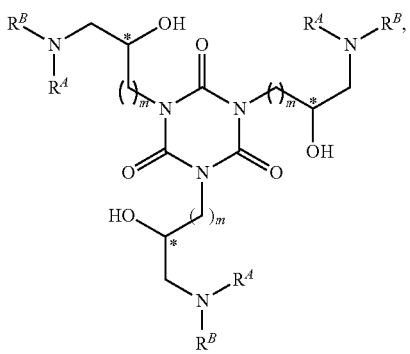

wherein the stereochemistry of each one of the three carbon atoms labeled with "*" is independently S or R. In certain embodiments, the compounds of Formula (I) are a mixture of stereoisomers. In certain embodiments, the mixture of stereoisomers is racemic.

In certain embodiments, all instances of $R^A$ are hydrogen or substituted or unsubstituted alkyl; all instances of $R^B$ are substituted or unsubstituted alkyl; and all instances of m are 1, 2, 3, 4, 5, or 6.

Compounds of Formula (I) include $R^A$ groups on the amino moieties. In certain embodiments, at least one instance of $R^A$ is H. In certain embodiments, at least one instance of $R^A$ is unsubstituted alkyl. In certain embodiments, at least one instance of $R^A$ is substituted alkyl. In certain embodiments, at least one instance of $R^A$ is unbranched alkyl. In certain embodiments, at least one instance of $R^A$ is unbranched and unsubstituted alkyl. In certain embodiments, at least one instance of $R^A$ is branched alkyl. In certain embodiments, at least one instance of $R^A$ is unsubstituted $C_{1-24}$ alkyl. In certain embodiments, at least one instance of $R^A$ is substituted $C_{1-24}$ alkyl. In certain embodiments, at least one instance of $R^A$ is unsubstituted $C_{6-24}$ alkyl. In certain embodiments, at least one instance of $R^A$ is substituted $C_{6-24}$ alkyl. In certain embodiments, at least one instance of $R^A$ is unsubstituted $C_{12-24}$ alkyl. In certain embodiments, at least one instance of $R^A$ is substituted $C_{12-24}$ alkyl. In certain embodiments, at least one instance of $R^A$ is unsubstituted $C_{18-24}$ alkyl. In certain embodiments, at least one instance of $R^A$ is substituted $C_{18-24}$ alkyl. In certain embodiments, at least one instance of $R^A$ is unsubstituted $C_{1-18}$ alkyl. In certain embodiments, at least one instance of $R^A$ is substituted $C_{1-18}$ alkyl. In certain embodiments, at least one instance of $R^A$ is unsubstituted $C_{6-18}$ alkyl. In certain embodiments, at least one instance of $R^A$ is substituted $C_{6-18}$ alkyl. In certain embodiments, at least one instance of $R^A$ is unsubstituted $C_{12-18}$ alkyl. In certain embodiments, at least one instance of $R^A$ is substituted $C_{12-18}$ alkyl. In certain embodiments, at least one instance of $R^A$ is unsubstituted $C_{1-12}$ alkyl. In certain embodiments, at least one instance of $R^A$ is substituted $C_{1-12}$ alkyl. In certain embodiments, at least one instance of $R^A$ is unsubstituted $C_{6-12}$ alkyl. In certain embodiments, at least one instance of $R^A$ is substituted $C_{6-12}$ alkyl. In certain embodiments, at least one instance of $R^A$ is unsubstituted $C_{1-6}$ alkyl. In certain embodiments, at least one instance of $R^A$ is substituted $C_{1-6}$ alkyl. In certain embodiments, at least one instance of $R^A$ is unsubstituted $C_{4-6}$ alkyl. In certain embodiments, at least one instance of $R^A$ is substituted $C_{4-6}$ alkyl. In certain embodiments, at least one instance of $R^A$ is unsubstituted $C_{1-4}$ alkyl. In certain embodiments, at least one instance of $R^A$ is substituted $C_{1-4}$ alkyl. In certain embodiments, at least one instance of $R^A$ is unsubstituted methyl. In certain embodiments, at least one instance of $R^A$ is substituted methyl. In certain embodiments, at least one instance of $R^A$ is —CH$_2$F. In certain embodiments, at least one instance of $R^A$ is —CHF$_2$. In certain embodiments, at least one instance of $R^A$ is —CF$_3$. In certain embodiments, at least one instance of $R^A$ is unsubstituted ethyl. In certain embodiments, at least one instance of $R^A$ is substituted ethyl. In certain embodiments, at least one instance of $R^A$ is fluorinated ethyl. In certain embodiments, at least one instance of $R^A$ is perfluorinated ethyl. In certain embodiments, at least one instance of $R^A$ is unsubstituted propyl. In certain embodiments, at least one instance of $R^A$ is substituted propyl. In certain embodiments, at least one instance of $R^A$ is fluorinated propyl. In certain embodiments, at least one instance of $R^A$ is perfluorinated propyl. In certain embodiments, at least one instance of $R^A$ is unsubstituted butyl. In certain embodiments, at least one instance of $R^A$ is substituted butyl. In certain embodiments, at least one instance of $R^A$ is fluorinated butyl. In certain embodiments, at least one instance of $R^A$ is perfluorinated butyl. In certain embodiments, at least one instance of $R^A$ is unsubstituted pentyl. In certain embodiments, at least one instance of $R^A$ is substituted pentyl. In certain embodiments, at least one instance of $R^A$ is fluorinated pentyl. In certain embodiments, at least one instance of $R^A$ is perfluorinated pentyl. In certain embodiments, at least one instance of $R^A$ is unsubstituted hexyl. In certain embodiments, at least one instance of $R^A$ is substituted hexyl. In certain embodiments, at least one instance of $R^A$ is fluorinated hexyl. In certain embodiments, at least one instance of $R^A$ is perfluorinated hexyl. In certain embodiments, at least one instance of $R^A$ is unsubstituted heptyl. In certain embodiments, at least one instance of $R^A$ is substituted heptyl. In certain embodiments, at least one instance of $R^A$ is fluorinated heptyl. In certain embodiments, at least one instance of $R^A$ is perfluorinated heptyl. In certain embodiments, at least one instance of $R^A$ is unsubstituted octyl. In certain embodiments, at least one instance of $R^A$ is substituted octyl. In certain embodiments, at least one instance of $R^A$ is fluorinated octyl. In certain embodiments, at least one instance of $R^A$ is perfluorinated octyl. In certain embodiments, at least one instance of $R^A$ is unsubstituted nonyl. In certain embodiments, at least one instance of $R^A$ is substituted nonyl. In certain embodiments, at least one instance of $R^A$ is fluorinated nonyl. In certain embodiments, at least one instance of $R^A$ is perfluorinated nonyl. In certain embodiments, at least one instance of $R^A$ is unsubstituted decyl. In certain embodiments, at least one instance of $R^A$ is substituted decyl. In certain embodiments, at least one instance of $R^A$ is fluorinated decyl. In certain embodiments, at least one instance of $R^A$ is perfluorinated decyl. In certain embodiments, at least one instance of $R^A$ is unsubstituted undecyl. In certain embodiments, at least one instance of $R^A$ is substituted undecyl. In certain embodiments, at least one instance of $R^A$ is fluorinated undecyl. In certain embodiments, at least one instance of $R^A$ is perfluorinated undecyl. In certain embodiments, at least one instance of $R^A$ is unsubstituted dodecyl. In certain embodiments, at least one instance of $R^A$ is substituted dodecyl. In certain embodiments, at least one instance of $R^A$ is fluorinated dodecyl. In certain embodiments, at least one instance of $R^A$ is perfluorinated dodecyl. In certain embodiments, at least one instance of $R^A$ is unsubstituted tridecyl. In certain embodiments, at least one instance of $R^A$ is substituted tridecyl. In certain embodiments, at least one instance of $R^A$ is fluorinated tridecyl. In certain embodiments, at least one instance of $R^A$ is perfluorinated tridecyl. In certain embodiments, at least one instance of $R^A$ is unsubstituted tetradecyl. In certain embodiments, at least one instance of $R^A$ is substituted tetradecyl. In certain embodiments, at least one instance of $R^A$ is fluorinated tetradecyl. In certain embodiments, at least one instance of $R^A$ is perfluorinated tetradecyl. In certain embodiments, at least one instance of $R^A$ is unsubstituted pentadecyl. In certain embodiments, at least one instance of $R^A$ is substituted pentadecyl. In certain embodiments, at least one instance of $R^A$ is fluorinated pentadecyl. In certain embodiments, at least one instance of $R^A$ is perfluorinated pentadecyl. In certain embodiments, at least one instance of $R^A$ is unsubstituted hexadecyl. In certain embodiments, at least one instance of $R^A$ is substituted hexadecyl. In certain embodiments, at least one instance of $R^A$ is fluorinated hexadecyl. In certain embodiments, at least one instance of $R^A$ is perfluorinated hexadecyl. In certain embodiments, at least one instance of $R^A$ is unsubstituted heptadecyl. In certain embodiments, at least one instance of $R^A$ is substituted heptadecyl. In certain embodiments, at least one instance of $R^A$ is fluorinated heptadecyl. In certain embodiments, at least one instance of $R^A$ is perfluorinated heptadecyl. In certain embodiments, at least one instance of $R^A$ is unsubstituted octadecyl. In certain embodiments, at least one instance of $R^A$ is substituted octadecyl. In certain embodiments, at least one instance of $R^A$ is fluorinated octadecyl. In certain embodiments, at least one instance of $R^A$ is perfluorinated octadecyl. In certain embodiments, at least one instance of $R^A$ is unsubstituted nonadecyl. In certain embodiments, at least one instance of $R^A$ is substituted nonadecyl. In certain embodiments, at least one instance of $R^A$ is fluorinated nonadecyl. In certain embodiments, at least one instance of $R^A$ is perfluorinated nonadecyl. In certain embodiments, at least one instance of $R^A$ is unsubstituted eicosyl. In certain embodiments, at least one instance of $R^A$ is substituted eicosyl. In certain embodiments, at least one instance of $R^A$ is fluorinated eicosyl. In certain embodiments, at least one instance of $R^A$ is perfluorinated eicosyl. In certain embodiments, at least one instance of $R^A$ is unsubstituted heneicosyl. In certain embodiments, at least one instance of $R^A$ is substituted heneicosyl. In certain embodiments, at least one instance of $R^A$ is fluorinated heneicosyl. In certain embodiments, at least one instance of $R^A$ is perfluorinated heneicosyl. In certain embodiments, at least one instance of $R^A$ is unsubstituted docosyl. In certain embodiments, at least one instance of $R^A$ is substituted docosyl. In certain embodiments, at least one instance of $R^A$ is fluorinated docosyl. In certain embodiments, at least one instance of $R^A$ is perfluorinated docosyl. In certain embodiments, at least one instance of $R^A$ is unsubstituted tricosyl. In certain embodiments, at least one instance of $R^A$ is substituted tricosyl. In certain embodiments, at least one instance of $R^A$ is fluorinated tricosyl. In certain embodiments, at least one instance of $R^A$ is perfluorinated tricosyl. In certain embodiments, at least one instance of $R^A$ is unsubstituted tetracosyl. In certain embodiments, at least one instance of $R^A$ is substituted tetracosyl. In certain embodiments, at least one instance of $R^A$ is fluorinated tetracosyl. In certain embodiments, at least one instance of $R^A$ is perfluorinated tetracosyl.

In certain embodiments, at least two instances of $R^A$ are H. In certain embodiments, at least two instances of $R^A$ are unsubstituted alkyl. In certain embodiments, at least two instances of $R^A$ are substituted alkyl. In certain embodiments, at least two instances of $R^A$ are unbranched alkyl. In certain embodiments, at least two instance of $R^A$ are unbranched and unsubstituted alkyl. In certain embodiments, at least two instances of $R^A$ are branched alkyl. In certain embodiments, at least two instances of $R^A$ are unsubstituted $C_{1-24}$ alkyl. In certain embodiments, at least two instances of $R^A$ are substituted $C_{1-24}$ alkyl. In certain embodiments, at least two instances of $R^A$ are unsubstituted $C_{6-24}$ alkyl. In certain embodiments, at least two instances of $R^A$ are substituted $C_{6-24}$ alkyl. In certain embodiments, at least two instances of $R^A$ are unsubstituted $C_{12-24}$ alkyl. In certain embodiments, at least two instances of $R^A$ are substituted $C_{12-24}$ alkyl. In certain embodiments, at least two instances of $R^A$ are unsubstituted $C_{18-24}$ alkyl. In certain embodiments, at least two instances of $R^A$ are substituted $C_{18-24}$ alkyl. In certain embodiments, at least two instances of $R^A$ are unsubstituted $C_{1-18}$ alkyl. In certain embodiments, at least two instances of $R^A$ are substituted $C_{1-18}$ alkyl. In certain embodiments, at least two instances of $R^A$ are unsubstituted $C_{6-18}$ alkyl. In certain embodiments, at least two instances of $R^A$ are substituted $C_{6-18}$ alkyl. In certain embodiments, at least two instances of $R^A$ are unsubstituted $C_{12-18}$ alkyl. In certain embodiments, at least two instances of $R^A$ are substituted $C_{12-18}$ alkyl. In certain embodiments, at least two instances of $R^A$ are unsubstituted $C_{1-12}$ alkyl. In certain embodiments, at least two instances of $R^A$ are substituted $C_{1-12}$ alkyl. In certain embodiments, at least two instances of $R^A$ are unsubstituted $C_{6-12}$ alkyl. In certain embodiments, at least two instances of $R^A$ are substituted $C_{6-12}$ alkyl. In certain embodiments, at least two instances of $R^A$ are unsubstituted $C_{1-6}$ alkyl. In certain embodiments, at least two instances of $R^A$ are substituted $C_{1-6}$ alkyl. In certain embodiments, at least two instances of $R^A$ are unsubstituted $C_{4-6}$ alkyl. In certain embodiments, at least two instances of $R^A$ are substituted $C_{4-6}$ alkyl. In certain embodiments, at least two instances of $R^A$ are unsubstituted $C_{1-4}$ alkyl. In certain embodiments, at least two instances of $R^A$ are substituted $C_{1-4}$ alkyl. In certain embodiments, at least two instances of $R^A$ are unsubstituted methyl. In certain embodiments, at least two instances of $R^A$ are substituted methyl. In certain embodiments, at least two instances of $R^A$ are —$CH_2F$. In certain embodiments, at least two instances of $R^A$ are —$CHF_2$. In certain embodiments, at least two instances of $R^A$ are —$CF_3$. In certain embodiments, at least two instances of $R^A$ are unsubstituted ethyl. In certain embodiments, at least two instances of $R^A$ are substituted ethyl. In certain embodiments, at least two instances of $R^A$ are fluorinated ethyl. In certain embodiments, at least two instances of $R^A$ are perfluorinated ethyl. In certain embodiments, at least two instances of $R^A$ are unsubstituted propyl. In certain embodiments, at least two instances of $R^A$ are substituted propyl. In certain embodiments, at least two instances of $R^A$ are fluorinated propyl. In certain embodiments, at least two instances of $R^A$ are perfluorinated propyl. In certain embodiments, at least two instances of $R^A$ are unsubstituted butyl. In certain embodiments, at least two instances of $R^A$ are substituted butyl. In certain embodiments, at least two instances of $R^A$ are fluorinated butyl. In certain embodiments, at least two instances of $R^A$ are perfluorinated butyl. In certain embodiments, at least two instances of $R^A$ are unsubstituted pentyl. In certain embodiments, at least two instances of $R^A$ are substituted pentyl. In certain embodiments, at least two instances of $R^A$ are fluorinated pentyl. In certain embodiments, at least two instances of $R^A$ are perfluorinated pentyl. In certain embodiments, at least two instances of $R^A$ are unsubstituted hexyl. In certain embodiments, at least two instances of $R^A$ are substituted hexyl. In certain embodiments, at least two instances of $R^A$ are fluorinated hexyl. In certain embodiments, at least two instances of $R^A$ are perfluorinated hexyl. In certain embodiments, at least two instances of $R^A$ are unsubstituted heptyl. In certain embodiments, at least two instances of $R^A$ are substituted heptyl. In certain embodiments, at least two instances of $R^A$ are fluorinated heptyl. In certain embodiments, at least two instances of $R^A$ are perfluorinated heptyl. In certain embodiments, at least two instances of $R^A$ are unsubstituted octyl. In certain embodiments, at least two instances of $R^A$ are substituted octyl. In certain embodiments, at least two instances of $R^A$ are fluorinated octyl. In certain embodiments, at least two instances of $R^A$ are perfluorinated octyl. In certain embodiments, at least two instances of $R^A$ are unsubstituted nonyl. In certain embodiments, at least two instances of $R^A$ are substituted nonyl. In certain embodiments, at least two instances of $R^A$ are fluorinated nonyl. In certain embodiments, at least two instances of $R^A$ are perfluorinated nonyl. In certain embodiments, at least two instances of $R^A$ are unsubstituted decyl. In certain embodiments, at least two instances of $R^A$ are substituted decyl. In certain embodiments, at least two instances of $R^A$ are fluorinated decyl. In certain embodiments, at least two instances of $R^A$ are perfluorinated decyl. In certain embodiments, at least two instances of $R^A$ are unsubstituted undecyl. In certain embodiments, at least two instances of $R^A$ are substituted undecyl. In certain embodiments, at least two instances of $R^A$ are fluorinated undecyl. In certain embodiments, at least two instances of $R^A$ are perfluorinated undecyl. In certain embodiments, at least two instances of $R^A$ are unsubstituted dodecyl. In certain embodiments, at least two instances of $R^A$ are substituted dodecyl. In certain embodiments, at least two instances of $R^A$ are fluorinated dodecyl. In certain embodiments, at least two instances of $R^A$ are perfluorinated dodecyl. In certain embodiments, at least two instances of $R^A$ are unsubstituted tridecyl. In certain embodiments, at least two instances of $R^A$ are substituted tridecyl. In certain embodiments, at least two instances of $R^A$ are fluorinated tridecyl. In certain embodiments, at least two instances of $R^A$ are perfluorinated tridecyl. In certain embodiments, at least two instances of $R^A$ are unsubstituted tetradecyl. In certain embodiments, at least two instances of $R^A$ are substituted tetradecyl. In certain embodiments, at least two instances of $R^A$ are fluorinated tetradecyl. In certain embodiments, at least two instances of $R^A$ are perfluorinated tetradecyl. In certain embodiments, at least two instances of $R^A$ are unsubstituted pentadecyl. In certain embodiments, at least two instances of $R^A$ are substituted pentadecyl. In certain embodiments, at least two instances of $R^A$ are fluorinated pentadecyl. In certain embodiments, at least two instances of $R^A$ are perfluorinated pentadecyl. In certain embodiments, at least two instances of $R^A$ are unsubstituted hexadecyl. In certain embodiments, at least two instances of $R^A$ are substituted hexadecyl. In certain embodiments, at least two instances of $R^A$ are fluorinated hexadecyl. In certain embodiments, at least two instances of $R^A$ are perfluorinated hexadecyl. In certain embodiments, at least two instances of $R^A$ are unsubstituted heptadecyl. In certain embodiments, at least two instances of $R^A$ are substituted heptadecyl. In certain embodiments, at least two instances of $R^A$ are fluorinated heptadecyl. In certain embodiments, at least two instances of $R^A$ are perfluorinated heptadecyl. In certain embodiments, at least two instances of $R^A$ are unsubstituted octadecyl. In certain embodiments, at least two instances of $R^A$ are substituted octadecyl. In certain embodiments, at least two instances of $R^A$ are fluorinated octadecyl. In certain embodiments, at least two instances of $R^A$ are perfluorinated octadecyl. In certain embodiments, at least two instances of $R^A$ are unsubstituted nonadecyl. In certain embodiments, at least two instances of $R^A$ are substituted nonadecyl. In certain embodiments, at least two instances of $R^A$ are fluorinated nonadecyl. In certain embodiments, at least two instances of $R^A$ are perfluorinated nonadecyl. In certain embodiments, at least two instances of $R^A$ are unsubstituted eicosyl. In certain embodiments, at least two instances of $R^A$ are substituted eicosyl. In certain embodiments, at least two instances of $R^A$ are fluorinated eicosyl. In certain embodiments, at least two instances of $R^A$ are perfluorinated eicosyl. In certain embodiments, at least two instances of $R^A$ are unsubstituted heneicosyl. In certain embodiments, at least two instances of $R^A$ are substituted heneicosyl. In certain embodiments, at least two instances of $R^A$ are fluorinated heneicosyl. In certain embodiments, at least two instances of $R^A$ are perfluorinated heneicosyl. In certain embodiments, at least two instances of $R^A$ are unsubstituted docosyl. In certain embodiments, at least two instances of $R^A$ are substituted docosyl. In certain embodiments, at least two instances of $R^A$ are fluorinated docosyl. In certain embodiments, at least two instances of $R^A$ are perfluorinated docosyl. In certain embodiments, at least two instances of $R^A$ are unsubstituted tricosyl. In certain embodiments, at least two instances of $R^A$ are substituted tricosyl. In certain embodiments, at least two instances of $R^A$ are fluorinated tricosyl. In certain embodiments, at least two instances of $R^A$ are perfluorinated tricosyl. In certain embodiments, at least two instances of $R^A$ are unsubstituted tetracosyl. In certain embodiments, at least two instances of $R^A$ are substituted tetracosyl. In certain embodiments, at least two instances of $R^A$ are fluorinated tetracosyl. In certain embodiments, at least two instances of $R^A$ are perfluorinated tetracosyl.

In certain embodiments, all instances of $R^A$ are H. In certain embodiments, all instances of $R^A$ are unsubstituted alkyl. In certain embodiments, all instances of $R^A$ are substituted alkyl. In certain embodiments, all instances of $R^A$ are unbranched alkyl. In certain embodiments, all instances of $R^A$ are unbranched and unsubstituted alkyl. In certain embodiments, all instances of $R^A$ are branched alkyl. In certain embodiments, all instances of $R^A$ are unsubstituted $C_{1-24}$ alkyl. In certain embodiments, all instances of $R^A$ are substituted $C_{1-24}$ alkyl. In certain embodiments, all instances of $R^A$ are unsubstituted $C_{6-24}$ alkyl. In certain embodiments, all instances of $R^A$ are substituted $C_{6-24}$ alkyl. In certain embodiments, all instances of $R^A$ are unsubstituted $C_{12-24}$ alkyl. In certain embodiments, all instances of $R^A$ are substituted $C_{12-24}$ alkyl. In certain embodiments, all instances of $R^A$ are unsubstituted $C_{18-24}$ alkyl. In certain embodiments, all instances of $R^A$ are substituted $C_{18-24}$ alkyl. In certain embodiments, all instances of $R^A$ are unsubstituted $C_{1-18}$ alkyl. In certain embodiments, all instances of $R^A$ are substituted $C_{1-18}$ alkyl. In certain embodiments, all instances of $R^A$ are unsubstituted $C_{6-18}$ alkyl. In certain embodiments, all instances of $R^A$ are substituted $C_{6-18}$ alkyl. In certain embodiments, all instances of $R^A$ are unsubstituted $C_{12-18}$ alkyl. In certain embodiments, all instances of $R^A$ are substituted $C_{12-18}$ alkyl. In certain embodiments, all instances of $R^A$ are unsubstituted $C_{1-12}$ alkyl. In certain embodiments, all instances of $R^A$ are substituted $C_{1-12}$ alkyl. In certain embodiments, all instances of $R^A$ are unsubstituted $C_{6-12}$ alkyl. In certain embodiments, all instances of $R^A$ are substituted $C_{6-12}$ alkyl. In certain embodiments, all instances of $R^A$ are unsubstituted $C_{1-6}$ alkyl. In certain embodiments, all instances of $R^A$ are substituted $C_{1-6}$ alkyl. In certain embodiments, all instances of $R^A$ are unsubstituted $C_{4-6}$ alkyl. In certain embodiments, all instances of $R^A$ are substituted $C_{4-6}$ alkyl. In certain embodiments, all instances of $R^A$ are unsubstituted $C_{1-4}$ alkyl. In certain embodiments, all instances of $R^A$ are substituted $C_{1-4}$ alkyl. In certain embodiments, all instances of $R^A$ are unsubstituted methyl. In certain embodiments, all instances of $R^A$ are substituted methyl. In certain embodiments, all instances of $R^A$ are —$CH_2F$. In certain embodiments, all instances of $R^A$ are —$CHF_2$. In certain embodiments, all instances of $R^A$ are —$CF_3$. In certain embodiments, all instances of $R^A$ are unsubstituted ethyl. In certain embodiments, all instances of $R^A$ are substituted ethyl. In certain embodiments, all instances of $R^A$ are fluorinated ethyl. In certain embodiments, all instances of $R^A$ are perfluorinated ethyl. In certain embodiments, all instances of $R^A$ are unsubstituted propyl. In certain embodiments, all instances of $R^A$ are substituted propyl. In certain embodiments, all instances of $R^A$ are fluorinated propyl. In certain embodiments, all instances of $R^A$ are perfluorinated propyl. In certain embodiments, all instances of $R^A$ are unsubstituted butyl. In certain embodiments, all instances of $R^A$ are substituted butyl. In certain embodiments, all instances of $R^A$ are fluorinated butyl. In certain embodiments, all instances of $R^A$ are perfluorinated butyl. In certain embodiments, all instances of $R^A$ are unsubstituted pentyl. In certain embodiments, all instances of $R^A$ are substituted pentyl. In certain embodiments, all instances of $R^A$ are fluorinated pentyl. In certain embodiments, all instances of $R^A$ are perfluorinated pentyl. In certain embodiments, all instances of $R^A$ are unsubstituted hexyl. In certain embodiments, all instances of $R^A$ are substituted hexyl. In certain embodiments, all instances of $R^A$ are fluorinated hexyl. In certain embodiments, all instances of $R^A$ are perfluorinated hexyl. In certain embodiments, all instances of $R^A$ are unsubstituted heptyl. In certain embodiments, all instances of $R^A$ are substituted heptyl. In certain embodiments, all instances of $R^A$ are fluorinated heptyl. In certain embodiments, all instances of $R^A$ are perfluorinated heptyl. In certain embodiments, all instances of $R^A$ are unsubstituted octyl. In certain embodiments, all instances of $R^A$ are substituted octyl. In certain embodiments, all instances of $R^A$ are fluorinated octyl. In certain embodiments, all instances of $R^A$ are perfluorinated octyl. In certain embodiments, all instances of $R^A$ are unsubstituted nonyl. In certain embodiments, all instances of $R^A$ are substituted nonyl. In certain embodiments, all instances of $R^A$ are fluorinated nonyl. In certain embodiments, all instances of $R^A$ are perfluorinated nonyl. In certain embodiments, all instances of $R^A$ are unsubstituted decyl. In certain embodiments, all instances of $R^A$ are substituted decyl. In certain embodiments, all instances of $R^A$ are fluorinated decyl. In certain embodiments, all instances of $R^A$ are perfluorinated decyl. In certain embodiments, all instances of $R^A$ are unsubstituted undecyl. In certain embodiments, all instances of $R^A$ are substituted undecyl. In certain embodiments, all instances of $R^A$ are fluorinated undecyl. In certain embodiments, all instances of $R^A$ are perfluorinated undecyl. In certain embodiments, all instances of $R^A$ are unsubstituted dodecyl. In certain embodiments, all instances of $R^A$ are substituted dodecyl. In certain embodiments, all instances of $R^A$ are fluorinated dodecyl. In certain embodiments, all instances of $R^A$ are perfluorinated dodecyl. In certain embodiments, all instances of $R^A$ are unsubstituted tridecyl. In certain embodiments, all instances of $R^A$ are substituted tridecyl. In certain embodiments, all instances of $R^A$ are fluorinated tridecyl. In certain embodiments, all instances of $R^A$ are perfluorinated tridecyl. In certain embodiments, all instances of $R^A$ are unsubstituted tetradecyl. In certain embodiments, all instances of $R^A$ are substituted tetradecyl. In certain embodiments, all instances of $R^A$ are fluorinated tetradecyl. In certain embodiments, all instances of $R^A$ are perfluorinated tetradecyl. In certain embodiments, all instances of $R^A$ are unsubstituted pentadecyl. In certain embodiments, all instances of $R^A$ are substituted pentadecyl. In certain embodiments, all instances of $R^A$ are fluorinated pentadecyl. In certain embodiments, all instances of $R^A$ are perfluorinated pentadecyl. In certain embodiments, all instances of $R^A$ are unsubstituted hexadecyl. In certain embodiments, all instances of $R^A$ are substituted hexadecyl. In certain embodiments, all instances of $R^A$ are fluorinated hexadecyl. In certain embodiments, all instances of $R^A$ are perfluorinated hexadecyl. In certain embodiments, all instances of $R^A$ are unsubstituted heptadecyl. In certain embodiments, all instances of $R^A$ are substituted heptadecyl. In certain embodiments, all instances of $R^A$ are fluorinated heptadecyl. In certain embodiments, all instances of $R^A$ are perfluorinated heptadecyl. In certain embodiments, all instances of $R^A$ are unsubstituted octadecyl. In certain embodiments, all instances of $R^A$ are substituted octadecyl. In certain embodiments, all instances of $R^A$ are fluorinated octadecyl. In certain embodiments, all instances of $R^A$ are perfluorinated octadecyl. In certain embodiments, all instances of $R^A$ are unsubstituted nonadecyl. In certain embodiments, all instances of $R^A$ are substituted nonadecyl. In certain embodiments, all instances of $R^A$ are fluorinated nonadecyl. In certain embodiments, all instances of $R^A$ are perfluorinated nonadecyl. In certain embodiments, all instances of $R^A$ are unsubstituted eicosyl. In certain embodiments, all instances of $R^A$ are substituted eicosyl. In certain embodiments, all instances of $R^A$ are fluorinated eicosyl. In certain embodiments, all instances of $R^A$ are perfluorinated eicosyl. In certain embodiments, all instances of $R^A$ are unsubstituted heneicosyl. In certain embodiments, all instances of $R^A$ are substituted heneicosyl. In certain embodiments, all instances of $R^A$ are fluorinated heneicosyl. In certain embodiments, all instances of $R^A$ are perfluorinated heneicosyl. In certain embodiments, all instances of $R^A$ are unsubstituted docosyl. In certain embodiments, all instances of $R^A$ are substituted docosyl. In certain embodiments, all instances of $R^A$ are fluorinated docosyl. In certain embodiments, all instances of $R^A$ are perfluorinated docosyl. In certain embodiments, all instances of $R^A$ are unsubstituted tricosyl. In certain embodiments, all instances of $R^A$ are substituted tricosyl. In certain embodiments, all instances of $R^A$ are fluorinated tricosyl. In certain embodiments, all instances of $R^A$ are perfluorinated tricosyl. In certain embodiments, all instances of $R^A$ are unsubstituted tetracosyl. In certain embodiments, all instances of $R^A$ are substituted tetracosyl. In certain embodiments, all instances of $R^A$ are fluorinated tetracosyl. In certain embodiments, all instances of $R^A$ are perfluorinated tetracosyl.

Compounds of Formula (I) include $R^B$ groups on the amino moieties. In certain embodiments, at least one instance of $R^B$ is H. In certain embodiments, at least one instance of $R^B$ is unsubstituted alkyl. In certain embodiments, at least one instance of $R^B$ is substituted alkyl. In certain embodiments, at least one instance of $R^B$ is unbranched alkyl. In certain embodiments, at least one instance of $R^B$ is unbranched and unsubstituted alkyl. In certain embodiments, at least one instance of $R^B$ is branched alkyl. In certain embodiments, at least one instance of $R^B$ is unsubstituted $C_{1-24}$ alkyl. In certain embodiments, at least one instance of $R^B$ is substituted $C_{1-24}$ alkyl. In certain embodiments, at least one instance of $R^B$ is unsubstituted $C_{6-24}$ alkyl. In certain embodiments, at least one instance of $R^B$ is substituted $C_{6-24}$ alkyl. In certain embodiments, at least one instance of $R^B$ is unsubstituted $C_{12-24}$ alkyl. In certain embodiments, at least one instance of $R^B$ is substituted $C_{12-24}$ alkyl. In certain embodiments, at least one instance of $R^B$ is unsubstituted $C_{18-24}$ alkyl. In certain embodiments, at least one instance of $R^B$ is substituted $C_{18-24}$ alkyl. In certain embodiments, at least one instance of $R^B$ is unsubstituted $C_{1-18}$ alkyl. In certain embodiments, at least one instance of $R^B$ is substituted $C_{1-18}$ alkyl. In certain embodiments, at least one instance of $R^B$ is unsubstituted $C_{6-18}$ alkyl. In certain embodiments, at least one instance of $R^B$ is substituted $C_{6-18}$ alkyl. In certain embodiments, at least one instance of $R^B$ is unsubstituted $C_{12-18}$ alkyl. In certain embodiments, at least one instance of $R^B$ is substituted $C_{12-18}$ alkyl. In certain embodiments, at least one instance of $R^B$ is unsubstituted $C_{1-12}$ alkyl. In certain embodiments, at least one instance of $R^B$ is substituted $C_{1-12}$ alkyl. In certain embodiments, at least one instance of $R^B$ is unsubstituted $C_{6-12}$ alkyl. In certain embodiments, at least one instance of $R^B$ is substituted $C_{6-12}$ alkyl. In certain embodiments, at least one instance of $R^B$ is unsubstituted $C_{1-6}$ alkyl. In certain embodiments, at least one instance of $R^B$ is substituted $C_{1-6}$ alkyl. In certain embodiments, at least one instance of $R^B$ is unsubstituted $C_{4-6}$ alkyl. In certain embodiments, at least one instance of $R^B$ is substituted $C_{4-6}$ alkyl. In certain embodiments, at least one instance of $R^B$ is unsubstituted $C_{1-4}$ alkyl. In certain embodiments, at least one instance of $R^B$ is substituted $C_{1-4}$ alkyl. In certain embodiments, at least one instance of $R^B$ is unsubstituted methyl. In certain embodiments, at least one instance of $R^B$ is substituted methyl. In certain embodiments, at least one instance of $R^B$ is —$CH_2F$. In certain embodiments, at least one instance of $R^B$ is —$CHF_2$. In certain embodiments, at least one instance of $R^B$ is —$CF_3$. In certain embodiments, at least one instance of $R^B$ is unsubstituted ethyl. In certain embodiments, at least one instance of $R^B$ is substituted ethyl. In certain embodiments, at least one instance of $R^B$ is fluorinated ethyl. In certain embodiments, at least one instance of $R^B$ is perfluorinated ethyl. In certain embodiments, at least one instance of $R^B$ is unsubstituted propyl. In certain embodiments, at least one instance of $R^B$ is substituted propyl. In certain embodiments, at least one instance of $R^B$ is fluorinated propyl. In certain embodiments, at least one instance of $R^B$ is perfluorinated propyl. In certain embodiments, at least one instance of $R^B$ is unsubstituted butyl. In certain embodiments, at least one instance of $R^B$ is substituted butyl. In certain embodiments, at least one instance of $R^B$ is fluorinated butyl. In certain embodiments, at least one instance of $R^B$ is perfluorinated butyl. In certain embodiments, at least one instance of $R^B$ is unsubstituted pentyl. In certain embodiments, at least one instance of $R^B$ is substituted pentyl. In certain embodiments, at least one instance of $R^B$ is fluorinated pentyl. In certain embodiments, at least one instance of $R^B$ is perfluorinated pentyl. In certain embodiments, at least one instance of $R^B$ is unsubstituted hexyl. In certain embodiments, at least one instance of $R^B$ is substituted hexyl. In certain embodiments, at least one instance of $R^B$ is fluorinated hexyl. In certain embodiments, at least one instance of $R^B$ is perfluorinated hexyl. In certain embodiments, at least one instance of $R^B$ is unsubstituted heptyl. In certain embodiments, at least one instance of $R^B$ is substituted heptyl. In certain embodiments, at least one instance of $R^B$ is fluorinated heptyl. In certain embodiments, at least one instance of $R^B$ is perfluorinated heptyl. In certain embodiments, at least one instance of $R^B$ is unsubstituted octyl. In certain embodiments, at least one instance of $R^B$ is substituted octyl. In certain embodiments, at least one instance of $R^B$ is fluorinated octyl. In certain embodiments, at least one instance of $R^B$ is perfluorinated octyl. In certain embodiments, at least one instance of $R^B$ is unsubstituted nonyl. In certain embodiments, at least one instance of $R^B$ is substituted nonyl. In certain embodiments, at least one instance of $R^B$ is fluorinated nonyl. In certain embodiments, at least one instance of $R^B$ is perfluorinated nonyl. In certain embodiments, at least one instance of $R^B$ is unsubstituted decyl. In certain embodiments, at least one instance of $R^B$ is substituted decyl. In certain embodiments, at least one instance of $R^B$ is fluorinated decyl. In certain embodiments, at least one instance of $R^B$ is perfluorinated decyl. In certain embodiments, at least one instance of $R^B$ is unsubstituted undecyl. In certain embodiments, at least one instance of $R^B$ is substituted undecyl. In certain embodiments, at least one instance of $R^B$ is fluorinated undecyl. In certain embodiments, at least one instance of $R^B$ is perfluorinated undecyl. In certain embodiments, at least one instance of $R^B$ is unsubstituted dodecyl. In certain embodiments, at least one instance of $R^B$ is substituted dodecyl. In certain embodiments, at least one instance of $R^B$ is fluorinated dodecyl. In certain embodiments, at least one instance of $R^B$ is perfluorinated dodecyl. In certain embodiments, at least one instance of $R^B$ is unsubstituted tridecyl. In certain embodiments, at least one instance of $R^B$ is substituted tridecyl. In certain embodiments, at least one instance of $R^B$ is fluorinated tridecyl. In certain embodiments, at least one instance of $R^B$ is perfluorinated tridecyl. In certain embodiments, at least one instance of $R^B$ is unsubstituted tetradecyl. In certain embodiments, at least one instance of $R^B$ is substituted tetradecyl. In certain embodiments, at least one instance of $R^B$ is fluorinated tetradecyl. In certain embodiments, at least one instance of $R^B$ is perfluorinated tetradecyl. In certain embodiments, at least one instance of $R^B$ is unsubstituted pentadecyl. In certain embodiments, at least one instance of $R^B$ is substituted pentadecyl. In certain embodiments, at least one instance of $R^B$ is fluorinated pentadecyl. In certain embodiments, at least one instance of $R^B$ is perfluorinated pentadecyl. In certain embodiments, at least one instance of $R^B$ is unsubstituted hexadecyl. In certain embodiments, at least one instance of $R^B$ is substituted hexadecyl. In certain embodiments, at least one instance of $R^B$ is fluorinated hexadecyl. In certain embodiments, at least one instance of $R^B$ is perfluorinated hexadecyl. In certain embodiments, at least one instance of $R^B$ is unsubstituted heptadecyl. In certain embodiments, at least one instance of $R^B$ is substituted heptadecyl. In certain embodiments, at least one instance of $R^B$ is fluorinated heptadecyl. In certain embodiments, at least one instance of $R^B$ is perfluorinated heptadecyl. In certain embodiments, at least one instance of $R^B$ is unsubstituted octadecyl. In certain embodiments, at least one instance of $R^B$ is substituted octadecyl. In certain embodiments, at least one instance of $R^B$ is fluorinated octadecyl. In certain embodiments, at least one instance of $R^B$ is perfluorinated octadecyl. In certain embodiments, at least one instance of $R^B$ is unsubstituted nonadecyl. In certain embodiments, at least one instance of $R^B$ is substituted nonadecyl. In certain embodiments, at least one instance of $R^B$ is fluorinated nonadecyl. In certain embodiments, at least one instance of $R^B$ is perfluorinated nonadecyl. In certain embodiments, at least one instance of $R^B$ is unsubstituted eicosyl. In certain embodiments, at least one instance of $R^B$ is substituted eicosyl. In certain embodiments, at least one instance of $R^B$ is fluorinated eicosyl. In certain embodiments, at least one instance of $R^B$ is perfluorinated eicosyl. In certain embodiments, at least one instance of $R^B$ is unsubstituted heneicosyl. In certain embodiments, at least one instance of $R^B$ is substituted heneicosyl. In certain embodiments, at least one instance of $R^B$ is fluorinated heneicosyl. In certain embodiments, at least one instance of $R^B$ is perfluorinated heneicosyl. In certain embodiments, at least one instance of $R^B$ is unsubstituted docosyl. In certain embodiments, at least one instance of $R^B$ is substituted docosyl. In certain embodiments, at least one instance of $R^B$ is fluorinated docosyl. In certain embodiments, at least one instance of $R^B$ is perfluorinated docosyl. In certain embodiments, at least one instance of $R^B$ is unsubstituted tricosyl. In certain embodiments, at least one instance of $R^B$ is substituted tricosyl. In certain embodiments, at least one instance of $R^B$ is fluorinated tricosyl. In certain embodiments, at least one instance of $R^B$ is perfluorinated tricosyl. In certain embodiments, at least one instance of $R^B$ is unsubstituted tetracosyl. In certain embodiments, at least one instance of $R^B$ is substituted tetracosyl. In certain embodiments, at least one instance of $R^B$ is fluorinated tetracosyl. In certain embodiments, at least one instance of $R^B$ is perfluorinated tetracosyl.

In certain embodiments, at least two instances of $R^B$ are H. In certain embodiments, at least two instances of $R^B$ are unsubstituted alkyl. In certain embodiments, at least two instances of $R^B$ are substituted alkyl. In certain embodiments, at least two instances of $R^B$ are unbranched alkyl. In certain embodiments, at least two instance of $R^B$ are unbranched and unsubstituted alkyl. In certain embodiments, at least two instances of $R^B$ are branched alkyl. In certain embodiments, at least two instances of $R^B$ are unsubstituted $C_{1-24}$ alkyl. In certain embodiments, at least two instances of $R^B$ are substituted $C_{1-24}$ alkyl. In certain embodiments, at least two instances of $R^B$ are unsubstituted $C_{6-24}$ alkyl. In certain embodiments, at least two instances of $R^B$ are substituted $C_{6-24}$ alkyl. In certain embodiments, at least two instances of $R^B$ are unsubstituted $C_{12-24}$ alkyl. In certain embodiments, at least two instances of $R^B$ are substituted $C_{12-24}$ alkyl. In certain embodiments, at least two instances of $R^B$ are unsubstituted $C_{18-24}$ alkyl. In certain embodiments, at least two instances of $R^B$ are substituted $C_{18-24}$ alkyl. In certain embodiments, at least two instances of $R^B$ are unsubstituted $C_{1-18}$ alkyl. In certain embodiments, at least two instances of $R^B$ are substituted $C_{1-18}$ alkyl. In certain embodiments, at least two instances of $R^B$ are unsubstituted $C_{6-18}$ alkyl. In certain embodiments, at least two instances of $R^B$ are substituted $C_{6-18}$ alkyl. In certain embodiments, at least two instances of $R^B$ are unsubstituted $C_{12-18}$ alkyl. In certain embodiments, at least two instances of $R^B$ are substituted $C_{12-18}$ alkyl. In certain embodiments, at least two instances of $R^B$ are unsubstituted $C_{1-12}$ alkyl. In certain embodiments, at least two instances of $R^B$ are substituted $C_{1-12}$ alkyl. In certain embodiments, at least two instances of $R^B$ are unsubstituted $C_{6-12}$ alkyl. In certain embodiments, at least two instances of $R^B$ are substituted $C_{6-12}$ alkyl. In certain embodiments, at least two instances of $R^B$ are unsubstituted $C_{1-6}$ alkyl. In certain embodiments, at least two instances of $R^B$ are substituted $C_{1-6}$ alkyl. In certain embodiments, at least two instances of $R^B$ are unsubstituted $C_{4-6}$ alkyl. In certain embodiments, at least two instances of $R^B$ are substituted $C_{4-6}$ alkyl. In certain embodiments, at least two instances of $R^B$ are unsubstituted $C_{1-4}$ alkyl. In certain embodiments, at least two instances of $R^B$ are substituted $C_{1-4}$ alkyl. In certain embodiments, at least two instances of $R^B$ are unsubstituted methyl. In certain embodiments, at least two instances of $R^B$ are substituted methyl. In certain embodiments, at least two instances of $R^B$ are —$CH_2F$. In certain embodiments, at least two instances of $R^B$ are —$CHF_2$. In certain embodiments, at least two instances of $R^B$ are —$CF_3$. In certain embodiments, at least two instances of $R^B$ are unsubstituted ethyl. In certain embodiments, at least two instances of $R^B$ are substituted ethyl. In certain embodiments, at least two instances of $R^B$ are fluorinated ethyl. In certain embodiments, at least two instances of $R^B$ are perfluorinated ethyl. In certain embodiments, at least two instances of $R^B$ are unsubstituted propyl. In certain embodiments, at least two instances of $R^B$ are substituted propyl. In certain embodiments, at least two instances of $R^B$ are fluorinated propyl. In certain embodiments, at least two instances of $R^B$ are perfluorinated propyl. In certain embodiments, at least two instances of $R^B$ are unsubstituted butyl. In certain embodiments, at least two instances of $R^B$ are substituted butyl. In certain embodiments, at least two instances of $R^B$ are fluorinated butyl. In certain embodiments, at least two instances of $R^B$ are perfluorinated butyl. In certain embodiments, at least two instances of $R^B$ are unsubstituted pentyl. In certain embodiments, at least two instances of $R^B$ are substituted pentyl. In certain embodiments, at least two instances of $R^B$ are fluorinated pentyl. In certain embodiments, at least two instances of $R^B$ are perfluorinated pentyl. In certain embodiments, at least two instances of $R^B$ are unsubstituted hexyl. In certain embodiments, at least two instances of $R^B$ are substituted hexyl. In certain embodiments, at least two instances of $R^B$ are fluorinated hexyl. In certain embodiments, at least two instances of $R^B$ are perfluorinated hexyl. In certain embodiments, at least two instances of $R^B$ are unsubstituted heptyl. In certain embodiments, at least two instances of $R^B$ are substituted heptyl. In certain embodiments, at least two instances of $R^B$ are fluorinated heptyl. In certain embodiments, at least two instances of $R^B$ are perfluorinated heptyl. In certain embodiments, at least two instances of $R^B$ are unsubstituted octyl. In certain embodiments, at least two instances of $R^B$ are substituted octyl. In certain embodiments, at least two instances of $R^B$ are fluorinated octyl. In certain embodiments, at least two instances of $R^B$ are perfluorinated octyl. In certain embodiments, at least two instances of $R^B$ are unsubstituted nonyl. In certain embodiments, at least two instances of $R^B$ are substituted nonyl. In certain embodiments, at least two instances of $R^B$ are fluorinated nonyl. In certain embodiments, at least two instances of $R^B$ are perfluorinated nonyl. In certain embodiments, at least two instances of $R^B$ are unsubstituted decyl. In certain embodiments, at least two instances of $R^B$ are substituted decyl. In certain embodiments, at least two instances of $R^B$ are fluorinated decyl. In certain embodiments, at least two instances of $R^B$ are perfluorinated decyl. In certain embodiments, at least two instances of $R^B$ are unsubstituted undecyl. In certain embodiments, at least two instances of $R^B$ are substituted undecyl. In certain embodiments, at least two instances of $R^B$ are fluorinated undecyl. In certain embodiments, at least two instances of $R^B$ are perfluorinated undecyl. In certain embodiments, at least two instances of $R^B$ are unsubstituted dodecyl. In certain embodiments, at least two instances of $R^B$ are substituted dodecyl. In certain embodiments, at least two instances of $R^B$ are fluorinated dodecyl. In certain embodiments, at least two instances of $R^B$ are perfluorinated dodecyl. In certain embodiments, at least two instances of $R^B$ are unsubstituted tridecyl. In certain embodiments, at least two instances of $R^B$ are substituted tridecyl. In certain embodiments, at least two instances of $R^B$ are fluorinated tridecyl. In certain embodiments, at least two instances of $R^B$ are perfluorinated tridecyl. In certain embodiments, at least two instances of $R^B$ are unsubstituted tetradecyl. In certain embodiments, at least two instances of $R^B$ are substituted tetradecyl. In certain embodiments, at least two instances of $R^B$ are fluorinated tetradecyl. In certain embodiments, at least two instances of $R^B$ are perfluorinated tetradecyl. In certain embodiments, at least two instances of $R^B$ are unsubstituted pentadecyl. In certain embodiments, at least two instances of $R^B$ are substituted pentadecyl. In certain embodiments, at least two instances of $R^B$ are fluorinated pentadecyl. In certain embodiments, at least two instances of $R^B$ are perfluorinated pentadecyl. In certain embodiments, at least two instances of $R^B$ are unsubstituted hexadecyl. In certain embodiments, at least two instances of $R^B$ are substituted hexadecyl. In certain embodiments, at least two instances of $R^B$ are fluorinated hexadecyl. In certain embodiments, at least two instances of $R^B$ are perfluorinated hexadecyl. In certain embodiments, at least two instances of $R^B$ are unsubstituted heptadecyl. In certain embodiments, at least two instances of $R^B$ are substituted heptadecyl. In certain embodiments, at least two instances of $R^B$ are fluorinated heptadecyl. In certain embodiments, at least two instances of $R^B$ are perfluorinated heptadecyl. In certain embodiments, at least two instances of $R^B$ are unsubstituted octadecyl. In certain embodiments, at least two instances of $R^B$ are substituted octadecyl. In certain embodiments, at least two instances of $R^B$ are fluorinated octadecyl. In certain embodiments, at least two instances of $R^B$ are perfluorinated octadecyl. In certain embodiments, at least two instances of $R^B$ are unsubstituted nonadecyl. In certain embodiments, at least two instances of $R^B$ are substituted nonadecyl. In certain embodiments, at least two instances of $R^B$ are fluorinated nonadecyl. In certain embodiments, at least two instances of $R^B$ are perfluorinated nonadecyl. In certain embodiments, at least two instances of $R^B$ are unsubstituted eicosyl. In certain embodiments, at least two instances of $R^B$ are substituted eicosyl. In certain embodiments, at least two instances of $R^B$ are fluorinated eicosyl. In certain embodiments, at least two instances of $R^B$ are perfluorinated eicosyl. In certain embodiments, at least two instances of $R^B$ are unsubstituted heneicosyl. In certain embodiments, at least two instances of $R^B$ are substituted heneicosyl. In certain embodiments, at least two instances of $R^B$ are fluorinated heneicosyl. In certain embodiments, at least two instances of $R^B$ are perfluorinated heneicosyl. In certain embodiments, at least two instances of $R^B$ are unsubstituted docosyl. In certain embodiments, at least two instances of $R^B$ are substituted docosyl. In certain embodiments, at least two instances of $R^B$ are fluorinated docosyl. In certain embodiments, at least two instances of $R^B$ are perfluorinated docosyl. In certain embodiments, at least two instances of $R^B$ are unsubstituted tricosyl. In certain embodiments, at least two instances of $R^B$ are substituted tricosyl. In certain embodiments, at least two instances of $R^B$ are fluorinated tricosyl. In certain embodiments, at least two instances of $R^B$ are perfluorinated tricosyl. In certain embodiments, at least two instances of $R^B$ are unsubstituted tetracosyl. In certain embodiments, at least two instances of $R^B$ are substituted tetracosyl. In certain embodiments, at least two instances of $R^B$ are fluorinated tetracosyl. In certain embodiments, at least two instances of $R^B$ are perfluorinated tetracosyl.

In certain embodiments, all instances of $R^B$ are unsubstituted alkyl. In certain embodiments, all instances of $R^B$ are substituted alkyl. In certain embodiments, all instances of $R^B$ are unbranched alkyl. In certain embodiments, all instances of $R^B$ are unbranched and unsubstituted alkyl. In certain embodiments, all instances of $R^B$ are branched alkyl. In certain embodiments, all instances of $R^B$ are unsubstituted $C_{1-24}$ alkyl. In certain embodiments, all instances of $R^B$ are substituted $C_{1-24}$ alkyl. In certain embodiments, all instances of $R^B$ are unsubstituted $C_{6-24}$ alkyl. In certain embodiments, all instances of $R^B$ are substituted $C_{6-24}$ alkyl. In certain embodiments, all instances of $R^B$ are unsubstituted $C_{12-24}$ alkyl. In certain embodiments, all instances of $R^B$ are substituted $C_{12-24}$ alkyl. In certain embodiments, all instances of $R^B$ are unsubstituted $C_{18-24}$ alkyl. In certain embodiments, all instances of $R^B$ are substituted $C_{18-24}$ alkyl. In certain embodiments, all instances of $R^B$ are unsubstituted $C_{1-18}$ alkyl. In certain embodiments, all instances of $R^B$ are substituted $C_{1-18}$ alkyl. In certain embodiments, all instances of $R^B$ are unsubstituted $C_{6-18}$ alkyl. In certain embodiments, all instances of $R^B$ are substituted $C_{6-18}$ alkyl. In certain embodiments, all instances of $R^B$ are unsubstituted $C_{12-18}$ alkyl. In certain embodiments, all instances of $R^B$ are substituted $C_{12-18}$ alkyl. In certain embodiments, all instances of $R^B$ are unsubstituted $C_{1-12}$ alkyl. In certain embodiments, all instances of $R^B$ are substituted $C_{1-12}$ alkyl. In certain embodiments, all instances of $R^B$ are unsubstituted $C_{6-12}$ alkyl. In certain embodiments, all instances of $R^B$ are substituted $C_{6-12}$ alkyl. In certain embodiments, all instances of $R^B$ are unsubstituted $C_{1-6}$ alkyl. In certain embodiments, all instances of $R^B$ are substituted $C_{1-6}$ alkyl. In certain embodiments, all instances of $R^B$ are unsubstituted $C_{4-6}$ alkyl. In certain embodiments, all instances of $R^B$ are substituted $C_{4-6}$ alkyl. In certain embodiments, all instances of $R^B$ are unsubstituted $C_{1-4}$ alkyl. In certain embodiments, all instances of $R^B$ are substituted $C_{1-4}$ alkyl. In certain embodiments, all instances of $R^B$ are unsubstituted methyl. In certain embodiments, all instances of $R^B$ are substituted methyl. In certain embodiments, all instances of $R^B$ are —CH$_2$F. In certain embodiments, all instances of $R^B$ are —CHF$_2$. In certain embodiments, all instances of $R^B$ are —CF$_3$. In certain embodiments, all instances of $R^B$ are unsubstituted ethyl. In certain embodiments, all instances of $R^B$ are substituted ethyl. In certain embodiments, all instances of $R^B$ are fluorinated ethyl. In certain embodiments, all instances of $R^B$ are perfluorinated ethyl. In certain embodiments, all instances of $R^B$ are unsubstituted propyl. In certain embodiments, all instances of $R^B$ are substituted propyl. In certain embodiments, all instances of $R^B$ are fluorinated propyl. In certain embodiments, all instances of $R^B$ are perfluorinated propyl. In certain embodiments, all instances of $R^B$ are unsubstituted butyl. In certain embodiments, all instances of $R^B$ are substituted butyl. In certain embodiments, all instances of $R^B$ are fluorinated butyl. In certain embodiments, all instances of $R^B$ are perfluorinated butyl. In certain embodiments, all instances of $R^B$ are unsubstituted pentyl. In certain embodiments, all instances of $R^B$ are substituted pentyl. In certain embodiments, all instances of $R^B$ are fluorinated pentyl. In certain embodiments, all instances of $R^B$ are perfluorinated pentyl. In certain embodiments, all instances of $R^B$ are unsubstituted hexyl. In certain embodiments, all instances of $R^B$ are substituted hexyl. In certain embodiments, all instances of $R^B$ are fluorinated hexyl. In certain embodiments, all instances of $R^B$ are perfluorinated hexyl. In certain embodiments, all instances of $R^B$ are unsubstituted heptyl. In certain embodiments, all instances of $R^B$ are substituted heptyl. In certain embodiments, all instances of $R^B$ are fluorinated heptyl. In certain embodiments, all instances of $R^B$ are perfluorinated heptyl. In certain embodiments, all instances of $R^B$ are unsubstituted octyl. In certain embodiments, all instances of $R^B$ are substituted octyl. In certain embodiments, all instances of $R^B$ are fluorinated octyl. In certain embodiments, all instances of $R^B$ are perfluorinated octyl. In certain embodiments, all instances of $R^B$ are unsubstituted nonyl. In certain embodiments, all instances of $R^B$ are substituted nonyl. In certain embodiments, all instances of $R^B$ are fluorinated nonyl. In certain embodiments, all instances of $R^B$ are perfluorinated nonyl. In certain embodiments, all instances of $R^B$ are unsubstituted decyl. In certain embodiments, all instances of $R^B$ are substituted decyl. In certain embodiments, all instances of $R^B$ are fluorinated decyl. In certain embodiments, all instances of $R^B$ are perfluorinated decyl. In certain embodiments, all instances of $R^B$ are unsubstituted undecyl. In certain embodiments, all instances of $R^B$ are substituted undecyl. In certain embodiments, all instances of $R^B$ are fluorinated undecyl. In certain embodiments, all instances of $R^B$ are perfluorinated undecyl. In certain embodiments, all instances of $R^B$ are unsubstituted dodecyl. In certain embodiments, all instances of $R^B$ are substituted dodecyl. In certain embodiments, all instances of $R^B$ are fluorinated dodecyl. In certain embodiments, all instances of $R^B$ are perfluorinated dodecyl. In certain embodiments, all instances of $R^B$ are unsubstituted tridecyl. In certain embodiments, all instances of $R^B$ are substituted tridecyl. In certain embodiments, all instances of $R^B$ are fluorinated tridecyl. In certain embodiments, all instances of $R^B$ are perfluorinated tridecyl. In certain embodiments, all instances of $R^B$ are unsubstituted tetradecyl. In certain embodiments, all instances of $R^B$ are substituted tetradecyl. In certain embodiments, all instances of $R^B$ are fluorinated tetradecyl. In certain embodiments, all instances of $R^B$ are perfluorinated tetradecyl. In certain embodiments, all instances of $R^B$ are unsubstituted pentadecyl. In certain embodiments, all instances of $R^B$ are substituted pentadecyl. In certain embodiments, all instances of $R^B$ are fluorinated pentadecyl. In certain embodiments, all instances of $R^B$ are perfluorinated pentadecyl. In certain embodiments, all instances of $R^B$ are unsubstituted hexadecyl. In certain embodiments, all instances of $R^B$ are substituted hexadecyl. In certain embodiments, all instances of $R^B$ are fluorinated hexadecyl. In certain embodiments, all instances of $R^B$ are perfluorinated hexadecyl. In certain embodiments, all instances of $R^B$ are unsubstituted heptadecyl. In certain embodiments, all instances of $R^B$ are substituted heptadecyl. In certain embodiments, all instances of $R^B$ are fluorinated heptadecyl. In certain embodiments, all instances of $R^B$ are perfluorinated heptadecyl. In certain embodiments, all instances of $R^B$ are unsubstituted octadecyl. In certain embodiments, all instances of $R^B$ are substituted octadecyl. In certain embodiments, all instances of $R^B$ are fluorinated octadecyl. In certain embodiments, all instances of $R^B$ are perfluorinated octadecyl. In certain embodiments, all instances of $R^B$ are unsubstituted nonadecyl. In certain embodiments, all instances of $R^B$ are substituted nonadecyl. In certain embodiments, all instances of $R^B$ are fluorinated nonadecyl. In certain embodiments, all instances of $R^B$ are perfluorinated nonadecyl. In certain embodiments, all instances of $R^B$ are unsubstituted eicosyl. In certain embodiments, all instances of $R^B$ are substituted eicosyl. In certain embodiments, all instances of $R^B$ are fluorinated eicosyl. In certain embodiments, all instances of $R^B$ are perfluorinated eicosyl. In certain embodiments, all instances of $R^B$ are unsubstituted heneicosyl. In certain embodiments, all instances of $R^B$ are substituted heneicosyl. In certain embodiments, all instances of $R^B$ are fluorinated heneicosyl. In certain embodiments, all instances of $R^B$ are perfluorinated heneicosyl. In certain embodiments, all instances of $R^B$ are unsubstituted docosyl. In certain embodiments, all instances of $R^B$ are substituted docosyl. In certain embodiments, all instances of $R^B$ are fluorinated docosyl. In certain embodiments, all instances of $R^B$ are perfluorinated docosyl. In certain embodiments, all instances of $R^B$ are unsubstituted tricosyl. In certain embodiments, all instances of $R^B$ are substituted tricosyl. In certain embodiments, all instances of $R^B$ are fluorinated tricosyl. In certain embodiments, all instances of $R^B$ are perfluorinated tricosyl. In certain embodiments, all instances of $R^B$ are unsubstituted tetracosyl. In certain embodiments, all instances of $R^B$ are substituted tetracosyl. In certain embodiments, all instances of $R^B$ are fluorinated tetracosyl. In certain embodiments, all instances of $R^B$ are perfluorinated tetracosyl.

In certain embodiments, all instances of $R^A$ are H; and all instances of $R^B$ are substituted or unsubstituted alkyl. In certain embodiments, all instances of $R^A$ are substituted or unsubstituted alkyl; and all instances of $R^B$ are substituted or unsubstituted alkyl. In certain embodiments, all instances of $R^A$ are unsubstituted alkyl; and all instances of $R^B$ are unsubstituted alkyl. In certain embodiments, all instances of $R^A$ are unsubstituted $C_{1-6}$ alkyl; and all instances of $R^B$ are unsubstituted $C_{1-24}$ alkyl. In certain embodiments, all instances of $R^A$ are unsubstituted $C_{1-6}$ alkyl; and all instances of $R^B$ are unsubstituted $C_{6-24}$ alkyl. In certain embodiments, all instances of $R^A$ are unsubstituted $C_{1-6}$ alkyl; and all instances of $R^B$ are unsubstituted $C_{12-24}$ alkyl. In certain embodiments, all instances of $R^A$ are unsubstituted $C_{1-6}$ alkyl; and all instances of $R^B$ are unsubstituted $C_{1-18}$ alkyl. In certain embodiments, all instances of $R^A$ are unsubstituted $C_{1-6}$ alkyl; and all instances of $R^B$ are unsubstituted $C_{6-18}$ alkyl. In certain embodiments, all instances of $R^A$ are unsubstituted $C_{1-6}$ alkyl; and all instances of $R^B$ are unsubstituted $C_{12-18}$ alkyl. In certain embodiments, all instances of $R^A$ are unsubstituted $C_{1-6}$ alkyl; and all instances of $R^B$ are unsubstituted $C_{1-12}$ alkyl. In certain embodiments, all instances of $R^A$ are unsubstituted $C_{1-6}$ alkyl; and all instances of $R^B$ are unsubstituted $C_{6-12}$ alkyl. In certain embodiments, all instances of $R^A$ are unsubstituted $C_{1-6}$ alkyl; and all instances of $R^B$ are unsubstituted $C_{1-6}$ alkyl. In certain embodiments, all instances of $R^A$ are unsubstituted methyl; and all instances of $R^B$ are unsubstituted $C_{1-24}$ alkyl. In certain embodiments, all instances of $R^A$ are unsubstituted methyl; and all instances of $R^B$ are unsubstituted $C_{6-24}$ alkyl. In certain embodiments, all instances of $R^A$ are unsubstituted methyl; and all instances of $R^B$ are unsubstituted $C_{12-24}$ alkyl. In certain embodiments, all instances of $R^A$ are unsubstituted methyl; and all instances of $R^B$ are unsubstituted $C_{1-18}$ alkyl. In certain embodiments, all instances of $R^A$ are unsubstituted methyl; and all instances of $R^B$ are unsubstituted $C_{6-18}$ alkyl. In certain embodiments, all instances of $R^A$ are unsubstituted methyl; and all instances of $R^B$ are unsubstituted $C_{12-18}$ alkyl. In certain embodiments, all instances of $R^A$ are unsubstituted methyl; and all instances of $R^B$ are unsubstituted $C_{1-12}$ alkyl. In certain embodiments, all instances of $R^A$ are unsubstituted methyl; and all instances of $R^B$ are unsubstituted $C_{6-12}$ alkyl. In certain embodiments, all instances of $R^A$ are unsubstituted methyl; and all instances of $R^B$ are unsubstituted $C_{1-6}$ alkyl. In certain embodiments, all instances of $R^A$ are unsubstituted $C_{4-6}$ alkyl; and all instances of $R^B$ are unsubstituted $C_{1-24}$ alkyl. In certain embodiments, all instances of $R^A$ are unsubstituted $C_{4-6}$ alkyl; and all instances of $R^B$ are unsubstituted $C_{6-24}$ alkyl. In certain embodiments, all instances of $R^A$ are unsubstituted $C_{4-6}$ alkyl; and all instances of $R^B$ are unsubstituted $C_{12-24}$ alkyl. In certain embodiments, all instances of $R^A$ are unsubstituted $C_{4-6}$ alkyl; and all instances of $R^B$ are unsubstituted $C_{1-18}$ alkyl. In certain embodiments, all instances of $R^A$ are unsubstituted $C_{4-6}$ alkyl; and all instances of $R^B$ are unsubstituted $C_{6-18}$ alkyl. In certain embodiments, all instances of $R^A$ are unsubstituted $C_{4-6}$ alkyl; and all instances of $R^B$ are unsubstituted $C_{12-18}$ alkyl. In certain embodiments, all instances of $R^A$ are unsubstituted $C_{4-6}$ alkyl; and all instances of $R^B$ are unsubstituted $C_{1-12}$ alkyl. In certain embodiments, all instances of $R^A$ are unsubstituted $C_{4-6}$ alkyl; and all instances of $R^B$ are unsubstituted $C_{6-12}$ alkyl. In certain embodiments, all instances of $R^A$ are unsubstituted $C_{4-6}$ alkyl; and all instances of $R^B$ are unsubstituted $C_{1-6}$ alkyl. In certain embodiments, all instances of $R^A$ are unsubstituted $C_{6-12}$ alkyl; and all instances of $R^B$ are unsubstituted $C_{1-24}$ alkyl. In certain embodiments, all instances of $R^A$ are unsubstituted $C_{6-12}$ alkyl; and all instances of $R^B$ are unsubstituted $C_{6-24}$ alkyl. In certain embodiments, all instances of $R^A$ are unsubstituted $C_{6-12}$ alkyl; and all instances of $R^B$ are unsubstituted $C_{12-24}$ alkyl. In certain embodiments, all instances of $R^A$ are unsubstituted $C_{6-12}$ alkyl; and all instances of $R^B$ are unsubstituted $C_{1-18}$ alkyl. In certain embodiments, all instances of $R^A$ are unsubstituted $C_{6-12}$ alkyl; and all instances of $R^B$ are unsubstituted $C_{6-18}$ alkyl. In certain embodiments, all instances of $R^A$ are unsubstituted $C_{6-12}$ alkyl; and all instances of $R^B$ are unsubstituted $C_{12-18}$ alkyl. In certain embodiments, all instances of $R^A$ are unsubstituted $C_{6-12}$ alkyl; and all instances of $R^B$ are unsubstituted $C_{1-12}$ alkyl. In certain embodiments, all instances of $R^A$ are unsubstituted $C_{6-12}$ alkyl; and all instances of $R^B$ are unsubstituted $C_{6-12}$ alkyl. In certain embodiments, all instances of $R^A$ are unsubstituted $C_{6-12}$ alkyl; and all instances of $R^B$ are unsubstituted $C_{1-6}$ alkyl. In certain embodiments, all instances of $R^A$ are unsubstituted $C_{12-24}$ alkyl; and all instances of $R^B$ are unsubstituted $C_{1-24}$ alkyl. In certain embodiments, all instances of $R^A$ are unsubstituted $C_{12-24}$ alkyl; and all instances of $R^B$ are unsubstituted $C_{6-24}$ alkyl. In certain embodiments, all instances of $R^A$ are unsubstituted $C_{12-24}$ alkyl; and all instances of $R^B$ are unsubstituted $C_{12-24}$ alkyl. In certain embodiments, all instances of $R^A$ are unsubstituted $C_{12-24}$ alkyl; and all instances of $R^B$ are unsubstituted $C_{1-18}$ alkyl. In certain embodiments, all instances of $R^A$ are unsubstituted $C_{12-24}$ alkyl; and all instances of $R^B$ are unsubstituted $C_{6-18}$ alkyl. In certain embodiments, all instances of $R^A$ are unsubstituted $C_{12-24}$ alkyl; and all instances of $R^B$ are unsubstituted $C_{12-18}$ alkyl. In certain embodiments, all instances of $R^A$ are unsubstituted $C_{12-24}$ alkyl; and all instances of $R^B$ are unsubstituted $C_{1-12}$ alkyl. In certain embodiments, all instances of $R^A$ are unsubstituted $C_{12-24}$ alkyl; and all instances of $R^B$ are unsubstituted $C_{6-12}$ alkyl. In certain embodiments, all instances of $R^A$ are unsubstituted $C_{12-24}$ alkyl; and all instances of $R^B$ are unsubstituted $C_{1-6}$ alkyl. In certain embodiments, all instances of $R^A$ are unsubstituted methyl; and all instances of $R^B$ are unsubstituted hexyl. In certain embodiments, all instances of $R^A$ are unsubstituted methyl; and all instances of $R^B$ are unsubstituted octyl. In certain embodiments, all instances of $R^A$ are unsubstituted methyl; and all instances of $R^B$ are unsubstituted dodecyl. In certain embodiments, all instances of $R^A$ are unsubstituted methyl; and all instances of $R^B$ are unsubstituted octadecyl. In certain embodiments, all instances of $R^A$ and $R^B$ are unsubstituted butyl. In certain embodiments, all instances of $R^A$ and $R^B$ are unsubstituted hexyl. In certain embodiments, all instances of $R^A$ and $R^B$ are unsubstituted octyl. In certain embodiments, all instances of $R^A$ and $R^B$ are unsubstituted decyl. In certain embodiments, all instances of $R^A$ and $R^B$ are unsubstituted tridecyl.

In certain embodiments, at least one instance of m is 1. In certain embodiments, at least one instance of m is 2. In certain embodiments, at least one instance of m is 3. In certain embodiments, at least one instance of m is 4. In certain embodiments, at least one instance of m is 5. In certain embodiments, at least one instance of m is 6.

In certain embodiments, at least two instances of m are 1. In certain embodiments, at least two instances of m are 2. In certain embodiments, at least two instances of m are 3. In certain embodiments, at least two instances of m are 4. In certain embodiments, at least two instances of m are 5. In certain embodiments, at least two instances of m are 6.

In certain embodiments, all instances of m are 1. In certain embodiments, all instances of m are 2. In certain embodiments, all instances of m are 3. In certain embodiments, all instances of m are 4. In certain embodiments, all instances of m are 5. In certain embodiments, all instances of m are 6.

In certain embodiments, all instances of $R^A$ are substituted or unsubstituted alkyl; all instances of $R^B$ are substituted or unsubstituted alkyl; and all instances of m are 1. In certain embodiments, all instances of $R^A$ are unsubstituted alkyl; all instances of $R^B$ are unsubstituted alkyl; and all instances of m are 1. In certain embodiments, all instances of $R^A$ are unsubstituted $C_{1-24}$ alkyl; all instances of $R^B$ are unsubstituted $C_{1-24}$ alkyl; and all instances of m are 1. In certain embodiments, all instances of $R^A$ are unsubstituted $C_{1-24}$ alkyl; all instances of $R^B$ are unsubstituted $C_{6-24}$ alkyl; and all instances of m are 1. In certain embodiments, all instances of $R^A$ are unsubstituted $C_{1-24}$ alkyl; all instances of $R^B$ are unsubstituted $C_{12-24}$ alkyl; and all instances of m are 1.

In certain embodiments, the compound of Formula (I) is of the formula:
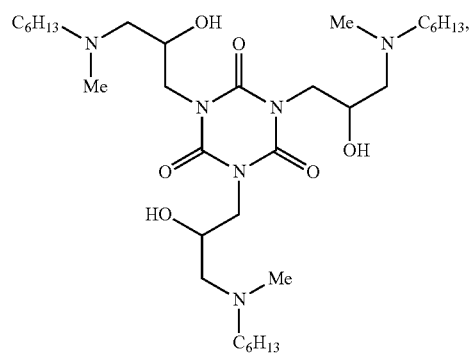
(I-1)
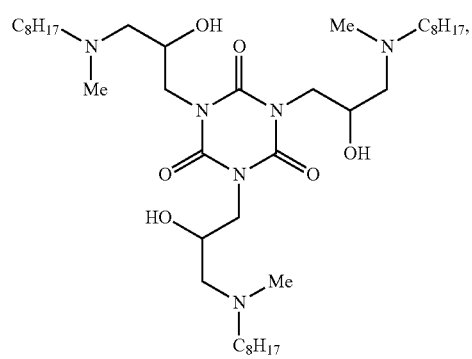
(I-2)
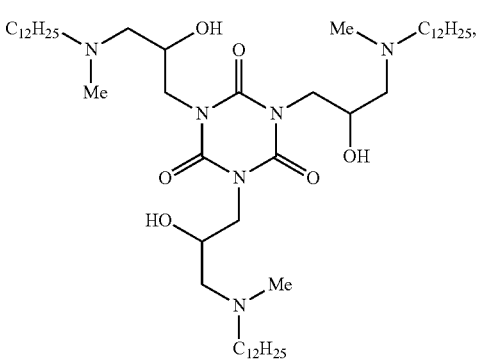
(I-3)
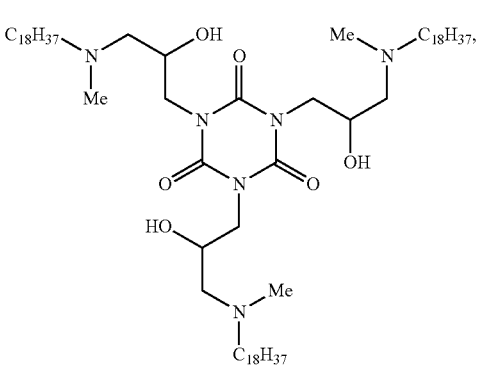
(I-4)
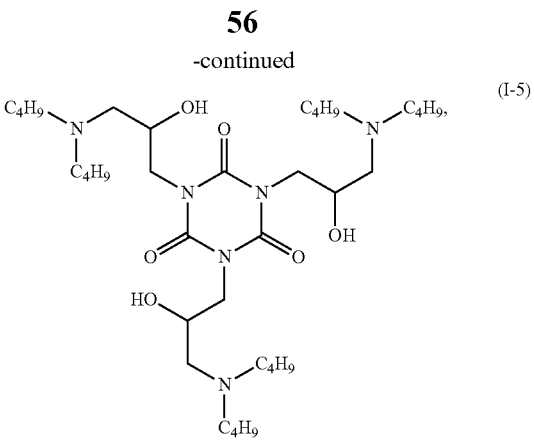
(I-5)
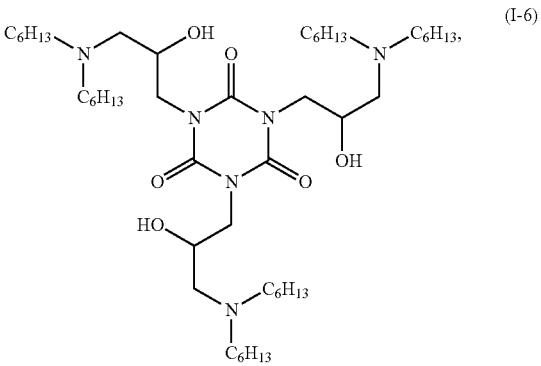
(I-6)
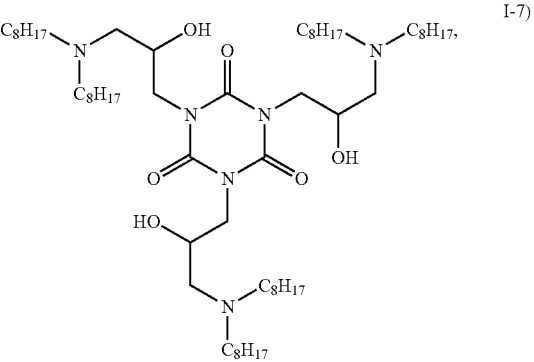
(I-7)
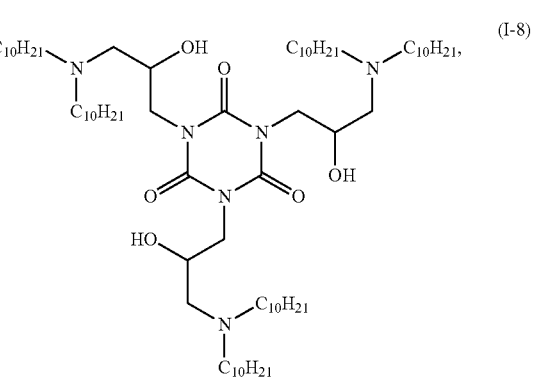
(I-8)

-continued

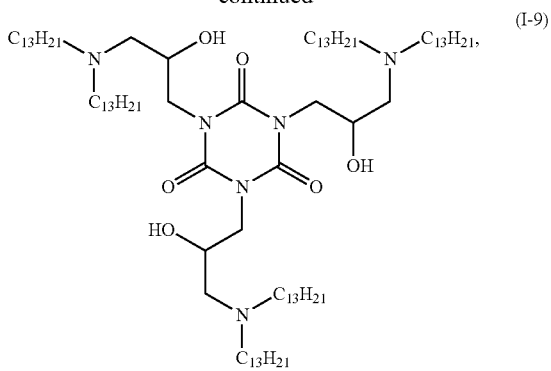

(I-9)

or a salt thereof.

In another aspect, the present invention provides compounds of Formula (II):

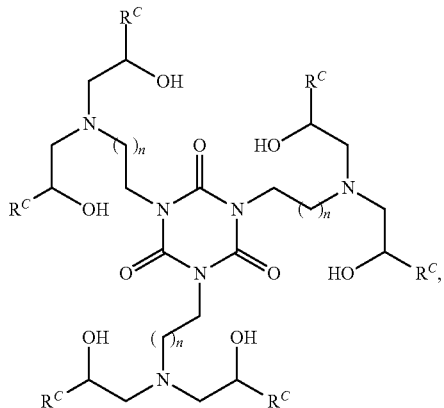

(II)

and salts thereof; wherein:
each instance of $R^C$ is independently substituted or unsubstituted alkyl; and
each instance of n is independently 1, 2, 3, 4, or 5.

In certain embodiments, provided are compounds of Formula (II), and pharmaceutically acceptable salts thereof.

In certain embodiments, all instances of $R^C$ are substituted or unsubstituted alkyl; and all instances of n are 1, 2, 3, 4, or 5.

In certain embodiments, the compound of Formula (II) is of the formula:

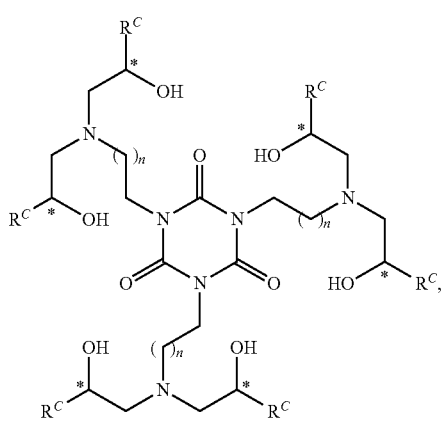

wherein the stereochemistry of each one of the six carbon atoms labeled with "*" is independently S or R. In certain embodiments, the compounds of Formula (II) are a mixture of stereoisomers. In certain embodiments, the mixture of stereoisomers is racemic.

Compounds of Formula (II) include $R^C$ groups. In certain embodiments, at least one instance of $R^C$ is H. In certain embodiments, at least one instance of $R^C$ is unsubstituted alkyl. In certain embodiments, at least one instance of $R^C$ is substituted alkyl. In certain embodiments, at least one instance of $R^C$ is unbranched alkyl. In certain embodiments, at least one instance of $R^C$ is unbranched and unsubstituted alkyl. In certain embodiments, at least one instance of $R^C$ is branched alkyl. In certain embodiments, at least one instance of $R^C$ is unsubstituted $C_{1-24}$ alkyl. In certain embodiments, at least one instance of $R^C$ is substituted $C_{1-24}$ alkyl. In certain embodiments, at least one instance of $R^C$ is unsubstituted $C_{6-24}$ alkyl. In certain embodiments, at least one instance of $R^C$ is substituted $C_{6-24}$ alkyl. In certain embodiments, at least one instance of $R^C$ is unsubstituted $C_{12-24}$ alkyl. In certain embodiments, at least one instance of $R^C$ is substituted $C_{12-24}$ alkyl. In certain embodiments, at least one instance of $R^C$ is unsubstituted $C_{18-24}$ alkyl. In certain embodiments, at least one instance of $R^C$ is substituted $C_{18-24}$ alkyl. In certain embodiments, at least one instance of $R^C$ is unsubstituted $C_{1-18}$ alkyl. In certain embodiments, at least one instance of $R^C$ is substituted $C_{1-18}$ alkyl. In certain embodiments, at least one instance of $R^C$ is unsubstituted $C_{6-18}$ alkyl. In certain embodiments, at least one instance of $R^C$ is substituted $C_{6-18}$ alkyl. In certain embodiments, at least one instance of $R^C$ is unsubstituted $C_{12-18}$ alkyl. In certain embodiments, at least one instance of $R^C$ is substituted $C_{12-18}$ alkyl. In certain embodiments, at least one instance of $R^C$ is unsubstituted $C_{1-12}$ alkyl. In certain embodiments, at least one instance of $R^C$ is substituted $C_{1-12}$ alkyl. In certain embodiments, at least one instance of $R^C$ is unsubstituted $C_{6-12}$ alkyl. In certain embodiments, at least one instance of $R^C$ is substituted $C_{6-12}$ alkyl. In certain embodiments, at least one instance of $R^C$ is unsubstituted $C_{1-6}$ alkyl. In certain embodiments, at least one instance of $R^C$ is substituted $C_{1-6}$ alkyl. In certain embodiments, at least one instance of $R^C$ is unsubstituted $C_{4-6}$ alkyl. In certain embodiments, at least one instance of $R^C$ is substituted $C_{4-6}$ alkyl. In certain embodiments, at least one instance of $R^C$ is unsubstituted $C_{1-4}$ alkyl. In certain embodiments, at least one instance of $R^C$ is substituted $C_{1-4}$ alkyl. In certain embodiments, at least one instance of $R^C$ is unsubstituted methyl. In certain embodiments, at least one instance of $R^C$ is substituted methyl. In certain embodiments, at least one instance of $R^C$ is $-CH_2F$. In certain embodiments, at least one instance of $R^C$ is $-CHF_2$. In certain embodiments, at least one instance of $R^C$ is $-CF_3$. In certain embodiments, at least one instance of $R^C$ is unsubstituted ethyl. In certain embodiments, at least one instance of $R^C$ is substituted ethyl. In certain embodiments, at least one instance of $R^C$ is fluorinated ethyl. In certain embodiments, at least one instance of $R^C$ is perfluorinated ethyl. In certain embodiments, at least one instance of $R^C$ is unsubstituted propyl. In certain embodiments, at least one instance of $R^C$ is substituted propyl. In certain embodiments, at least one instance of $R^C$ is fluorinated propyl. In certain embodiments, at least one instance of $R^C$ is perfluorinated propyl. In certain embodiments, at least one instance of $R^C$ is unsubstituted butyl. In certain embodiments, at least one instance of $R^C$ is substituted butyl. In certain embodiments, at least one instance of $R^C$ is fluorinated butyl. In certain embodiments, at least one instance of $R^C$ is perfluorinated butyl. In certain embodiments, at least one instance of $R^C$ is unsubstituted pentyl. In certain embodiments, at least one instance of $R^C$ is substituted pentyl. In certain embodiments, at least one instance of $R^C$ is fluorinated pentyl. In certain embodiments, at least one instance of $R^C$ is perfluorinated pentyl. In certain embodiments, at least one instance of $R^C$ is unsubstituted hexyl. In certain embodiments, at least one instance of $R^C$ is substituted hexyl. In certain embodiments, at least one instance of $R^C$ is fluorinated hexyl. In certain embodiments, at least one instance of $R^C$ is perfluorinated hexyl. In certain embodiments, at least one instance of $R^C$ is unsubstituted heptyl. In certain embodiments, at least one instance of $R^C$ is substituted heptyl. In certain embodiments, at least one instance of $R^C$ is fluorinated heptyl. In certain embodiments, at least one instance of $R^C$ is perfluorinated heptyl. In certain embodiments, at least one instance of $R^C$ is unsubstituted octyl. In certain embodiments, at least one instance of $R^C$ is substituted octyl. In certain embodiments, at least one instance of $R^C$ is fluorinated octyl. In certain embodiments, at least one instance of $R^C$ is perfluorinated octyl. In certain embodiments, at least one instance of $R^C$ is unsubstituted nonyl. In certain embodiments, at least one instance of $R^C$ is substituted nonyl. In certain embodiments, at least one instance of $R^C$ is fluorinated nonyl. In certain embodiments, at least one instance of $R^C$ is perfluorinated nonyl. In certain embodiments, at least one instance of $R^C$ is unsubstituted decyl. In certain embodiments, at least one instance of $R^C$ is substituted decyl. In certain embodiments, at least one instance of $R^C$ is fluorinated decyl. In certain embodiments, at least one instance of $R^C$ is perfluorinated decyl. In certain embodiments, at least one instance of $R^C$ is unsubstituted undecyl. In certain embodiments, at least one instance of $R^C$ is substituted undecyl. In certain embodiments, at least one instance of $R^C$ is fluorinated undecyl. In certain embodiments, at least one instance of $R^C$ is perfluorinated undecyl. In certain embodiments, at least one instance of $R^C$ is unsubstituted dodecyl. In certain embodiments, at least one instance of $R^C$ is substituted dodecyl. In certain embodiments, at least one instance of $R^C$ is fluorinated dodecyl. In certain embodiments, at least one instance of $R^C$ is perfluorinated dodecyl. In certain embodiments, at least one instance of $R^C$ is unsubstituted tridecyl. In certain embodiments, at least one instance of $R^C$ is substituted tridecyl. In certain embodiments, at least one instance of $R^C$ is fluorinated tridecyl. In certain embodiments, at least one instance of $R^C$ is perfluorinated tridecyl. In certain embodiments, at least one instance of $R^C$ is unsubstituted tetradecyl. In certain embodiments, at least one instance of $R^C$ is substituted tetradecyl. In certain embodiments, at least one instance of $R^C$ is fluorinated tetradecyl. In certain embodiments, at least one instance of $R^C$ is perfluorinated tetradecyl. In certain embodiments, at least one instance of $R^C$ is unsubstituted pentadecyl. In certain embodiments, at least one instance of $R^C$ is substituted pentadecyl. In certain embodiments, at least one instance of $R^C$ is fluorinated pentadecyl. In certain embodiments, at least one instance of $R^C$ is perfluorinated pentadecyl. In certain embodiments, at least one instance of $R^C$ is unsubstituted hexadecyl. In certain embodiments, at least one instance of $R^C$ is substituted hexadecyl. In certain embodiments, at least one instance of $R^C$ is fluorinated hexadecyl. In certain embodiments, at least one instance of $R^C$ is perfluorinated hexadecyl. In certain embodiments, at least one instance of $R^C$ is unsubstituted heptadecyl. In certain embodiments, at least one instance of $R^C$ is substituted heptadecyl. In certain embodiments, at least one instance of $R^C$ is fluorinated heptadecyl. In certain embodiments, at least one instance of $R^C$ is perfluorinated heptadecyl. In certain embodiments, at least one instance of $R^C$ is unsubstituted octadecyl. In certain embodiments, at least one instance of $R^C$ is substituted octadecyl. In certain embodiments, at least one instance of $R^C$ is fluorinated octadecyl. In certain embodiments, at least one instance of $R^C$ is perfluorinated octadecyl. In certain embodiments, at least one instance of $R^C$ is unsubstituted nonadecyl. In certain embodiments, at least one instance of $R^C$ is substituted nonadecyl. In certain embodiments, at least one instance of $R^C$ is fluorinated nonadecyl. In certain embodiments, at least one instance of $R^C$ is perfluorinated nonadecyl. In certain embodiments, at least one instance of $R^C$ is unsubstituted eicosyl. In certain embodiments, at least one instance of $R^C$ is substituted eicosyl. In certain embodiments, at least one instance of $R^C$ is fluorinated eicosyl. In certain embodiments, at least one instance of $R^C$ is perfluorinated eicosyl. In certain embodiments, at least one instance of $R^C$ is unsubstituted heneicosyl. In certain embodiments, at least one instance of $R^C$ is substituted heneicosyl. In certain embodiments, at least one instance of $R^C$ is fluorinated heneicosyl. In certain embodiments, at least one instance of $R^C$ is perfluorinated heneicosyl. In certain embodiments, at least one instance of $R^C$ is unsubstituted docosyl. In certain embodiments, at least one instance of $R^C$ is substituted docosyl. In certain embodiments, at least one instance of $R^C$ is fluorinated docosyl. In certain embodiments, at least one instance of $R^C$ is perfluorinated docosyl. In certain embodiments, at least one instance of $R^C$ is unsubstituted tricosyl. In certain embodiments, at least one instance of $R^C$ is substituted tricosyl. In certain embodiments, at least one instance of $R^C$ is fluorinated tricosyl. In certain embodiments, at least one instance of $R^C$ is perfluorinated tricosyl. In certain embodiments, at least one instance of $R^C$ is unsubstituted tetracosyl. In certain embodiments, at least one instance of $R^C$ is substituted tetracosyl. In certain embodiments, at least one instance of $R^C$ is fluorinated tetracosyl. In certain embodiments, at least one instance of $R^C$ is perfluorinated tetracosyl.

In certain embodiments, at least two instances of $R^C$ are H. In certain embodiments, at least two instances of $R^C$ are unsubstituted alkyl. In certain embodiments, at least two instances of $R^C$ are substituted alkyl. In certain embodiments, at least two instances of $R^C$ are unbranched alkyl. In certain embodiments, at least two instance of $R^C$ are unbranched and unsubstituted alkyl. In certain embodiments, at least two instances of $R^C$ are branched alkyl. In certain embodiments, at least two instances of $R^C$ are unsubstituted $C_{1-24}$ alkyl. In certain embodiments, at least two instances of $R^C$ are substituted $C_{1-24}$ alkyl. In certain embodiments, at least two instances of $R^C$ are unsubstituted $C_{6-24}$ alkyl. In certain embodiments, at least two instances of $R^C$ are substituted $C_{6-24}$ alkyl. In certain embodiments, at least two instances of $R^C$ are unsubstituted $C_{12-24}$ alkyl. In certain embodiments, at least two instances of $R^C$ are substituted $C_{12-24}$ alkyl. In certain embodiments, at least two instances of $R^C$ are unsubstituted $C_{18-24}$ alkyl. In certain embodiments, at least two instances of $R^C$ are substituted $C_{18-24}$ alkyl. In certain embodiments, at least two instances of $R^C$ are unsubstituted $C_{1-18}$ alkyl. In certain embodiments, at least two instances of $R^C$ are substituted $C_{1-18}$ alkyl. In certain embodiments, at least two instances of $R^C$ are unsubstituted $C_{6-18}$ alkyl. In certain embodiments, at least two instances of $R^C$ are substituted $C_{6-18}$ alkyl. In certain embodiments, at least two instances of $R^C$ are unsubstituted $C_{12-18}$ alkyl. In certain embodiments, at least two instances of $R^C$ are substituted $C_{12-18}$ alkyl. In certain embodiments, at least two instances of $R^C$ are unsubstituted $C_{1-12}$ alkyl. In certain embodiments, at least two instances of $R^C$ are substituted $C_{1-12}$ alkyl. In certain embodiments, at least two instances of $R^C$ are unsubstituted $C_{6-12}$ alkyl. In certain embodiments, at least two instances of $R^C$ are substituted $C_{6-12}$ alkyl. In certain embodiments, at least two instances of $R^C$ are unsubstituted $C_{1-6}$ alkyl. In certain embodiments, at least two instances of $R^C$ are substituted $C_{1-6}$ alkyl. In certain embodiments, at least two instances of $R^C$ are unsubstituted $C_{4-6}$ alkyl. In certain embodiments, at least two instances of $R^C$ are substituted $C_{4-6}$ alkyl. In certain embodiments, at least two instances of $R^C$ are unsubstituted $C_{1-4}$ alkyl. In certain embodiments, at least two instances of $R^C$ are substituted $C_{1-4}$ alkyl. In certain embodiments, at least two instances of $R^C$ are unsubstituted methyl. In certain embodiments, at least two instances of $R^C$ are substituted methyl. In certain embodiments, at least two instances of $R^C$ are —$CH_2F$. In certain embodiments, at least two instances of $R^C$ are —$CHF_2$. In certain embodiments, at least two instances of $R^C$ are —$CF_3$. In certain embodiments, at least two instances of $R^C$ are unsubstituted ethyl. In certain embodiments, at least two instances of $R^C$ are substituted ethyl. In certain embodiments, at least two instances of $R^C$ are fluorinated ethyl. In certain embodiments, at least two instances of $R^C$ are perfluorinated ethyl. In certain embodiments, at least two instances of $R^C$ are unsubstituted propyl. In certain embodiments, at least two instances of $R^C$ are substituted propyl. In certain embodiments, at least two instances of $R^C$ are fluorinated propyl. In certain embodiments, at least two instances of $R^C$ are perfluorinated propyl. In certain embodiments, at least two instances of $R^C$ are unsubstituted butyl. In certain embodiments, at least two instances of $R^C$ are substituted butyl. In certain embodiments, at least two instances of $R^C$ are fluorinated butyl. In certain embodiments, at least two instances of $R^C$ are perfluorinated butyl. In certain embodiments, at least two instances of $R^C$ are unsubstituted pentyl. In certain embodiments, at least two instances of $R^C$ are substituted pentyl. In certain embodiments, at least two instances of $R^C$ are fluorinated pentyl. In certain embodiments, at least two instances of $R^C$ are perfluorinated pentyl. In certain embodiments, at least two instances of $R^C$ are unsubstituted hexyl. In certain embodiments, at least two instances of $R^C$ are substituted hexyl. In certain embodiments, at least two instances of $R^C$ are fluorinated hexyl. In certain embodiments, at least two instances of $R^C$ are perfluorinated hexyl. In certain embodiments, at least two instances of $R^C$ are unsubstituted heptyl. In certain embodiments, at least two instances of $R^C$ are substituted heptyl. In certain embodiments, at least two instances of $R^C$ are fluorinated heptyl. In certain embodiments, at least two instances of $R^C$ are perfluorinated heptyl. In certain embodiments, at least two instances of $R^C$ are unsubstituted octyl. In certain embodiments, at least two instances of $R^C$ are substituted octyl. In certain embodiments, at least two instances of $R^C$ are fluorinated octyl. In certain embodiments, at least two instances of $R^C$ are perfluorinated octyl. In certain embodiments, at least two instances of $R^C$ are unsubstituted nonyl. In certain embodiments, at least two instances of $R^C$ are substituted nonyl. In certain embodiments, at least two instances of $R^C$ are fluorinated nonyl. In certain embodiments, at least two instances of $R^C$ are perfluorinated nonyl. In certain embodiments, at least two instances of $R^C$ are unsubstituted decyl. In certain embodiments, at least two instances of $R^C$ are substituted decyl. In certain embodiments, at least two instances of $R^C$ are fluorinated decyl. In certain embodiments, at least two instances of $R^C$ are perfluorinated decyl. In certain embodiments, at least two instances of $R^C$ are unsubstituted undecyl. In certain embodiments, at least two instances of $R^C$ are substituted undecyl. In certain embodiments, at least two instances of $R^C$ are fluorinated undecyl. In certain embodiments, at least two instances of $R^C$ are perfluorinated undecyl. In certain embodiments, at least two instances of $R^C$ are unsubstituted dodecyl. In certain embodiments, at least two instances of $R^C$ are substituted dodecyl. In certain embodiments, at least two instances of $R^C$ are fluorinated dodecyl. In certain embodiments, at least two instances of $R^C$ are perfluorinated dodecyl. In certain embodiments, at least two instances of $R^C$ are unsubstituted tridecyl. In certain embodiments, at least two instances of $R^C$ are substituted tridecyl. In certain embodiments, at least two instances of $R^C$ are fluorinated tridecyl. In certain embodiments, at least two instances of $R^C$ are perfluorinated tridecyl. In certain embodiments, at least two instances of $R^C$ are unsubstituted tetradecyl. In certain embodiments, at least two instances of $R^C$ are substituted tetradecyl. In certain embodiments, at least two instances of $R^C$ are fluorinated tetradecyl. In certain embodiments, at least two instances of $R^C$ are perfluorinated tetradecyl. In certain embodiments, at least two instances of $R^C$ are unsubstituted pentadecyl. In certain embodiments, at least two instances of $R^C$ are substituted pentadecyl. In certain embodiments, at least two instances of $R^C$ are fluorinated pentadecyl. In certain embodiments, at least two instances of $R^C$ are perfluorinated pentadecyl. In certain embodiments, at least two instances of $R^C$ are unsubstituted hexadecyl. In certain embodiments, at least two instances of $R^C$ are substituted hexadecyl. In certain embodiments, at least two instances of $R^C$ are fluorinated hexadecyl. In certain embodiments, at least two instances of $R^C$ are perfluorinated hexadecyl. In certain embodiments, at least two instances of $R^C$ are unsubstituted heptadecyl. In certain embodiments, at least two instances of $R^C$ are substituted heptadecyl. In certain embodiments, at least two instances of $R^C$ are fluorinated heptadecyl. In certain embodiments, at least two instances of $R^C$ are perfluorinated heptadecyl. In certain embodiments, at least two instances of $R^C$ are unsubstituted octadecyl. In certain embodiments, at least two instances of $R^C$ are substituted octadecyl. In certain embodiments, at least two instances of $R^C$ are fluorinated octadecyl. In certain embodiments, at least two instances of $R^C$ are perfluorinated octadecyl. In certain embodiments, at least two instances of $R^C$ are unsubstituted nonadecyl. In certain embodiments, at least two instances of $R^C$ are substituted nonadecyl. In certain embodiments, at least two instances of $R^C$ are fluorinated nonadecyl. In certain embodiments, at least two instances of $R^C$ are perfluorinated nonadecyl. In certain embodiments, at least two instances of $R^C$ are unsubstituted eicosyl. In certain embodiments, at least two instances of $R^C$ are substituted eicosyl. In certain embodiments, at least two instances of $R^C$ are fluorinated eicosyl. In certain embodiments, at least two instances of $R^C$ are perfluorinated eicosyl. In certain embodiments, at least two instances of $R^C$ are unsubstituted heneicosyl. In certain embodiments, at least two instances of $R^C$ are substituted heneicosyl. In certain embodiments, at least two instances of $R^C$ are fluorinated heneicosyl. In certain embodiments, at least two instances of $R^C$ are perfluorinated heneicosyl. In certain embodiments, at least two instances of $R^C$ are unsubstituted docosyl. In certain embodiments, at least two instances of $R^C$ are substituted docosyl. In certain embodiments, at least two instances of $R^C$ are fluorinated docosyl. In certain embodiments, at least two instances of $R^C$ are perfluorinated docosyl. In certain embodiments, at least two instances of $R^C$ are unsubstituted tricosyl. In certain embodiments, at least two instances of $R^C$ are substituted tricosyl. In certain embodiments, at least two instances of $R^C$ are fluorinated tricosyl. In certain embodiments, at least two instances of $R^C$ are perfluorinated tricosyl. In certain embodiments, at least two instances of $R^C$ are unsubstituted tetracosyl. In certain embodiments, at least two instances of $R^C$ are substituted tetracosyl. In certain embodiments, at least two instances of $R^C$ are fluorinated tetracosyl. In certain embodiments, at least two instances of $R^C$ are perfluorinated tetracosyl.

In certain embodiments, at least three instances of $R^C$ are H. In certain embodiments, at least three instances of $R^C$ are unsubstituted alkyl. In certain embodiments, at least three instances of $R^C$ are substituted alkyl. In certain embodiments, at least three instances of $R^C$ are unbranched alkyl. In certain embodiments, at least three instance of $R^C$ are unbranched and unsubstituted alkyl. In certain embodiments, at least three instances of $R^C$ are branched alkyl. In certain embodiments, at least three instances of $R^C$ are unsubstituted $C_{1-24}$ alkyl. In certain embodiments, at least three instances of $R^C$ are substituted $C_{1-24}$ alkyl. In certain embodiments, at least three instances of $R^C$ are unsubstituted $C_{6-24}$ alkyl. In certain embodiments, at least three instances of $R^C$ are substituted $C_{6-24}$ alkyl. In certain embodiments, at least three instances of $R^C$ are unsubstituted $C_{12-24}$ alkyl. In certain embodiments, at least three instances of $R^C$ are substituted $C_{12-24}$ alkyl. In certain embodiments, at least three instances of $R^C$ are unsubstituted $C_{18-24}$ alkyl. In certain embodiments, at least three instances of $R^C$ are substituted $C_{18-24}$ alkyl. In certain embodiments, at least three instances of $R^C$ are unsubstituted $C_{1-18}$ alkyl. In certain embodiments, at least three instances of $R^C$ are substituted $C_{1-18}$ alkyl. In certain embodiments, at least three instances of $R^C$ are unsubstituted $C_{6-18}$ alkyl. In certain embodiments, at least three instances of $R^C$ are substituted $C_{6-18}$ alkyl. In certain embodiments, at least three instances of $R^C$ are unsubstituted $C_{12-18}$ alkyl. In certain embodiments, at least three instances of $R^C$ are substituted $C_{12-18}$ alkyl. In certain embodiments, at least three instances of $R^C$ are unsubstituted $C_{1-12}$ alkyl. In certain embodiments, at least three instances of $R^C$ are substituted $C_{1-12}$ alkyl. In certain embodiments, at least three instances of $R^C$ are unsubstituted $C_{6-12}$ alkyl. In certain embodiments, at least three instances of $R^C$ are substituted $C_{6-12}$ alkyl. In certain embodiments, at least three instances of $R^C$ are unsubstituted $C_{1-6}$ alkyl. In certain embodiments, at least three instances of $R^C$ are substituted $C_{1-6}$ alkyl. In certain embodiments, at least three instances of $R^C$ are unsubstituted $C_{4-6}$ alkyl. In certain embodiments, at least three instances of $R^C$ are substituted $C_{4-6}$ alkyl. In certain embodiments, at least three instances of $R^C$ are unsubstituted $C_{1-4}$ alkyl. In certain embodiments, at least three instances of $R^C$ are substituted $C_{1-4}$ alkyl. In certain embodiments, at least three instances of $R^C$ are unsubstituted methyl. In certain embodiments, at least three instances of $R^C$ are substituted methyl. In certain embodiments, at least three instances of $R^C$ are —$CH_2F$. In certain embodiments, at least three instances of $R^C$ are —$CHF_2$. In certain embodiments, at least three instances of $R^C$ are —$CF_3$. In certain embodiments, at least three instances of $R^C$ are unsubstituted ethyl. In certain embodiments, at least three instances of $R^C$ are substituted ethyl. In certain embodiments, at least three instances of $R^C$ are fluorinated ethyl. In certain embodiments, at least three instances of $R^C$ are perfluorinated ethyl. In certain embodiments, at least three instances of $R^C$ are unsubstituted propyl. In certain embodiments, at least three instances of $R^C$ are substituted propyl. In certain embodiments, at least three instances of $R^C$ are fluorinated propyl. In certain embodiments, at least three instances of $R^C$ are perfluorinated propyl. In certain embodiments, at least three instances of $R^C$ are unsubstituted butyl. In certain embodiments, at least three instances of $R^C$ are substituted butyl. In certain embodiments, at least three instances of $R^C$ are fluorinated butyl. In certain embodiments, at least three instances of $R^C$ are perfluorinated butyl. In certain embodiments, at least three instances of $R^C$ are unsubstituted pentyl. In certain embodiments, at least three instances of $R^C$ are substituted pentyl. In certain embodiments, at least three instances of $R^C$ are fluorinated pentyl. In certain embodiments, at least three instances of $R^C$ are perfluorinated pentyl. In certain embodiments, at least three instances of $R^C$ are unsubstituted hexyl. In certain embodiments, at least three instances of $R^C$ are substituted hexyl. In certain embodiments, at least three instances of $R^C$ are fluorinated hexyl. In certain embodiments, at least three instances of $R^C$ are perfluorinated hexyl. In certain embodiments, at least three instances of $R^C$ are unsubstituted heptyl. In certain embodiments, at least three instances of $R^C$ are substituted heptyl. In certain embodiments, at least three instances of $R^C$ are fluorinated heptyl. In certain embodiments, at least three instances of $R^C$ are perfluorinated heptyl. In certain embodiments, at least three instances of $R^C$ are unsubstituted octyl. In certain embodiments, at least three instances of $R^C$ are substituted octyl. In certain embodiments, at least three instances of $R^C$ are fluorinated octyl. In certain embodiments, at least three instances of $R^C$ are perfluorinated octyl. In certain embodiments, at least three instances of $R^C$ are unsubstituted nonyl. In certain embodiments, at least three instances of $R^C$ are substituted nonyl. In certain embodiments, at least three instances of $R^C$ are fluorinated nonyl. In certain embodiments, at least three instances of $R^C$ are perfluorinated nonyl. In certain embodiments, at least three instances of $R^C$ are unsubstituted decyl. In certain embodiments, at least three instances of $R^C$ are substituted decyl. In certain embodiments, at least three instances of $R^C$ are fluorinated decyl. In certain embodiments, at least three instances of $R^C$ are perfluorinated decyl. In certain embodiments, at least three instances of $R^C$ are unsubstituted undecyl. In certain embodiments, at least three instances of $R^C$ are substituted undecyl. In certain embodiments, at least three instances of $R^C$ are fluorinated undecyl. In certain embodiments, at least three instances of $R^C$ are perfluorinated undecyl. In certain embodiments, at least three instances of $R^C$ are unsubstituted dodecyl. In certain embodiments, at least three instances of $R^C$ are substituted dodecyl. In certain embodiments, at least three instances of $R^C$ are fluorinated dodecyl. In certain embodiments, at least three instances of $R^C$ are perfluorinated dodecyl. In certain embodiments, at least three instances of $R^C$ are unsubstituted tridecyl. In certain embodiments, at least three instances of $R^C$ are substituted tridecyl. In certain embodiments, at least three instances of $R^C$ are fluorinated tridecyl. In certain embodiments, at least three instances of $R^C$ are perfluorinated tridecyl. In certain embodiments, at least three instances of $R^C$ are unsubstituted tetradecyl. In certain embodiments, at least three instances of $R^C$ are substituted tetradecyl. In certain embodiments, at least three instances of $R^C$ are fluorinated tetradecyl. In certain embodiments, at least three instances of $R^C$ are perfluorinated tetradecyl. In certain embodiments, at least three instances of $R^C$ are unsubstituted pentadecyl. In certain embodiments, at least three instances of $R^C$ are substituted pentadecyl. In certain embodiments, at least three instances of $R^C$ are fluorinated pentadecyl. In certain embodiments, at least three instances of $R^C$ are perfluorinated pentadecyl. In certain embodiments, at least three instances of $R^C$ are unsubstituted hexadecyl. In certain embodiments, at least three instances of $R^C$ are substituted hexadecyl. In certain embodiments, at least three instances of $R^C$ are fluorinated hexadecyl. In certain embodiments, at least three instances of $R^C$ are perfluorinated hexadecyl. In certain embodiments, at least three instances of $R^C$ are unsubstituted heptadecyl. In certain embodiments, at least three instances of $R^C$ are substituted heptadecyl. In certain embodiments, at least three instances of $R^C$ are fluorinated heptadecyl. In certain embodiments, at least three instances of $R^C$ are perfluorinated heptadecyl. In certain embodiments, at least three instances of $R^C$ are unsubstituted octadecyl. In certain embodiments, at least three instances of $R^C$ are substituted octadecyl. In certain embodiments, at least three instances of $R^C$ are fluorinated octadecyl. In certain embodiments, at least three instances of $R^C$ are perfluorinated octadecyl. In certain embodiments, at least three instances of $R^C$ are unsubstituted nonadecyl. In certain embodiments, at least three instances of $R^C$ are substituted nonadecyl. In certain embodiments, at least three instances of $R^C$ are fluorinated nonadecyl. In certain embodiments, at least three instances of $R^C$ are perfluorinated nonadecyl. In certain embodiments, at least three instances of $R^C$ are unsubstituted eicosyl. In certain embodiments, at least three instances of $R^C$ are substituted eicosyl. In certain embodiments, at least three instances of $R^C$ are fluorinated eicosyl. In certain embodiments, at least three instances of $R^C$ are perfluorinated eicosyl. In certain embodiments, at least three instances of $R^C$ are unsubstituted heneicosyl. In certain embodiments, at least three instances of $R^C$ are substituted heneicosyl. In certain embodiments, at least three instances of $R^C$ are fluorinated heneicosyl. In certain embodiments, at least three instances of $R^C$ are perfluorinated heneicosyl. In certain embodiments, at least three instances of $R^C$ are unsubstituted docosyl. In certain embodiments, at least three instances of $R^C$ are substituted docosyl. In certain embodiments, at least three instances of $R^C$ are fluorinated docosyl. In certain embodiments, at least three instances of $R^C$ are perfluorinated docosyl. In certain embodiments, at least three instances of $R^C$ are unsubstituted tricosyl. In certain embodiments, at least three instances of $R^C$ are substituted tricosyl. In certain embodiments, at least three instances of $R^C$ are fluorinated tricosyl. In certain embodiments, at least three instances of $R^C$ are perfluorinated tricosyl. In certain embodiments, at least three instances of $R^C$ are unsubstituted tetracosyl. In certain embodiments, at least three instances of $R^C$ are substituted tetracosyl. In certain embodiments, at least three instances of $R^C$ are fluorinated tetracosyl. In certain embodiments, at least three instances of $R^C$ are perfluorinated tetracosyl.

In certain embodiments, all instances of $R^C$ are H. In certain embodiments, all instances of $R^C$ are unsubstituted alkyl. In certain embodiments, all instances of $R^C$ are substituted alkyl. In certain embodiments, all instances of $R^C$ are unbranched alkyl. In certain embodiments, all instances of $R^C$ are unbranched and unsubstituted alkyl. In certain embodiments, all instances of $R^C$ are branched alkyl. In certain embodiments, all instances of $R^C$ are unsubstituted $C_{1-24}$ alkyl. In certain embodiments, all instances of $R^C$ are substituted $C_{1-24}$ alkyl. In certain embodiments, all instances of $R^C$ are unsubstituted $C_{6-24}$ alkyl. In certain embodiments, all instances of $R^C$ are substituted $C_{6-24}$ alkyl. In certain embodiments, all instances of $R^C$ are unsubstituted $C_{12-24}$ alkyl. In certain embodiments, all instances of $R^C$ are substituted $C_{12-24}$ alkyl. In certain embodiments, all instances of $R^C$ are unsubstituted $C_{18-24}$ alkyl. In certain embodiments, all instances of $R^C$ are substituted $C_{18-24}$ alkyl. In certain embodiments, all instances of $R^C$ are unsubstituted $C_{1-18}$ alkyl. In certain embodiments, all instances of $R^C$ are substituted $C_{1-18}$ alkyl. In certain embodiments, all instances of $R^C$ are unsubstituted $C_{6-18}$ alkyl. In certain embodiments, all instances of $R^C$ are substituted $C_{6-18}$ alkyl. In certain embodiments, all instances of $R^C$ are unsubstituted $C_{12-18}$ alkyl. In certain embodiments, all instances of $R^C$ are substituted $C_{12-18}$ alkyl. In certain embodiments, all instances of $R^C$ are unsubstituted $C_{1-12}$ alkyl. In certain embodiments, all instances of $R^C$ are substituted $C_{1-12}$ alkyl. In certain embodiments, all instances of $R^C$ are unsubstituted $C_{6-12}$ alkyl. In certain embodiments, all instances of $R^C$ are substituted $C_{6-12}$ alkyl. In certain embodiments, all instances of $R^C$ are unsubstituted $C_{1-6}$ alkyl. In certain embodiments, all instances of $R^C$ are substituted $C_{1-6}$ alkyl. In certain embodiments, all instances of $R^C$ are unsubstituted $C_{4-6}$ alkyl. In certain embodiments, all instances of $R^C$ are substituted $C_{4-6}$ alkyl. In certain embodiments, all instances of $R^C$ are unsubstituted $C_{1-4}$ alkyl. In certain embodiments, all instances of $R^C$ are substituted $C_{1-4}$ alkyl. In certain embodiments, all instances of $R^C$ are unsubstituted methyl. In certain embodiments, all instances of $R^C$ are substituted methyl. In certain embodiments, all instances of $R^C$ are —$CH_2F$. In certain embodiments, all instances of $R^C$ are —$CHF_2$. In certain embodiments, all instances of $R^C$ are —$CF_3$. In certain embodiments, all instances of $R^C$ are unsubstituted ethyl. In certain embodiments, all instances of $R^C$ are substituted ethyl. In certain embodiments, all instances of $R^C$ are fluorinated ethyl. In certain embodiments, all instances of $R^C$ are perfluorinated ethyl. In certain embodiments, all instances of $R^C$ are unsubstituted propyl. In certain embodiments, all instances of $R^C$ are substituted propyl. In certain embodiments, all instances of $R^C$ are fluorinated propyl. In certain embodiments, all instances of $R^C$ are perfluorinated propyl. In certain embodiments, all instances of $R^C$ are unsubstituted butyl. In certain embodiments, all instances of $R^C$ are substituted butyl. In certain embodiments, all instances of $R^C$ are fluorinated butyl. In certain embodiments, all instances of $R^C$ are perfluorinated butyl. In certain embodiments, all instances of $R^C$ are unsubstituted pentyl. In certain embodiments, all instances of $R^C$ are substituted pentyl. In certain embodiments, all instances of $R^C$ are fluorinated pentyl. In certain embodiments, all instances of $R^C$ are perfluorinated pentyl. In certain embodiments, all instances of $R^C$ are unsubstituted hexyl. In certain embodiments, all instances of $R^C$ are substituted hexyl. In certain embodiments, all instances of $R^C$ are fluorinated hexyl. In certain embodiments, all instances of $R^C$ are perfluorinated hexyl. In certain embodiments, all instances of $R^C$ are unsubstituted heptyl. In certain embodiments, all instances of $R^C$ are substituted heptyl. In certain embodiments, all instances of $R^C$ are fluorinated heptyl. In certain embodiments, all instances of $R^C$ are perfluorinated heptyl. In certain embodiments, all instances of $R^C$ are unsubstituted octyl. In certain embodiments, all instances of $R^C$ are substituted octyl. In certain embodiments, all instances of $R^C$ are fluorinated octyl. In certain embodiments, all instances of $R^C$ are perfluorinated octyl. In certain embodiments, all instances of $R^C$ are unsubstituted nonyl. In certain embodiments, all instances of $R^C$ are substituted nonyl. In certain embodiments, all instances of $R^C$ are fluorinated nonyl. In certain embodiments, all instances of $R^C$ are perfluorinated nonyl. In certain embodiments, all instances of $R^C$ are unsubstituted decyl. In certain embodiments, all instances of $R^C$ are substituted decyl. In certain embodiments, all instances of $R^C$ are fluorinated decyl. In certain embodiments, all instances of $R^C$ are perfluorinated decyl. In certain embodiments, all instances of $R^C$ are unsubstituted undecyl. In certain embodiments, all instances of $R^C$ are substituted undecyl. In certain embodiments, all instances of $R^C$ are fluorinated undecyl. In certain embodiments, all instances of $R^C$ are perfluorinated undecyl. In certain embodiments, all instances of $R^C$ are unsubstituted dodecyl. In certain embodiments, all instances of $R^C$ are substituted dodecyl. In certain embodiments, all instances of $R^C$ are fluorinated dodecyl. In certain embodiments, all instances of $R^C$ are perfluorinated dodecyl. In certain embodiments, all instances of $R^C$ are unsubstituted tridecyl. In certain embodiments, all instances of $R^C$ are substituted tridecyl. In certain embodiments, all instances of $R^C$ are fluorinated tridecyl. In certain embodiments, all instances of $R^C$ are perfluorinated tridecyl. In certain embodiments, all instances of $R^C$ are unsubstituted tetradecyl. In certain embodiments, all instances of $R^C$ are substituted tetradecyl. In certain embodiments, all instances of $R^C$ are fluorinated tetradecyl. In certain embodiments, all instances of $R^C$ are perfluorinated tetradecyl. In certain embodiments, all instances of $R^C$ are unsubstituted pentadecyl. In certain embodiments, all instances of $R^C$ are substituted pentadecyl. In certain embodiments, all instances of $R^C$ are fluorinated pentadecyl. In certain embodiments, all instances of $R^C$ are perfluorinated pentadecyl. In certain embodiments, all instances of $R^C$ are unsubstituted hexadecyl. In certain embodiments, all instances of $R^C$ are substituted hexadecyl. In certain embodiments, all instances of $R^C$ are fluorinated hexadecyl. In certain embodiments, all instances of $R^C$ are perfluorinated hexadecyl. In certain embodiments, all instances of $R^C$ are unsubstituted heptadecyl. In certain embodiments, all instances of $R^C$ are substituted heptadecyl. In certain embodiments, all instances of $R^C$ are fluorinated heptadecyl. In certain embodiments, all instances of $R^C$ are perfluorinated heptadecyl. In certain embodiments, all instances of $R^C$ are unsubstituted octadecyl. In certain embodiments, all instances of $R^C$ are substituted octadecyl. In certain embodiments, all instances of $R^C$ are fluorinated octadecyl. In certain embodiments, all instances of $R^C$ are perfluorinated octadecyl. In certain embodiments, all instances of $R^C$ are unsubstituted nonadecyl. In certain embodiments, all instances of $R^C$ are substituted nonadecyl. In certain embodiments, all instances of $R^C$ are fluorinated nonadecyl. In certain embodiments, all instances of $R^C$ are perfluorinated nonadecyl. In certain embodiments, all instances of $R^C$ are unsubstituted eicosyl. In certain embodiments, all instances of $R^C$ are substituted eicosyl. In certain embodiments, all instances of $R^C$ are fluorinated eicosyl. In certain embodiments, all instances of $R^C$ are perfluorinated eicosyl. In certain embodiments, all instances of $R^C$ are unsubstituted heneicosyl. In certain embodiments, all instances of $R^C$ are substituted heneicosyl. In certain embodiments, all instances of $R^C$ are fluorinated heneicosyl. In certain embodiments, all instances of $R^C$ are perfluorinated heneicosyl. In certain embodiments, all instances of $R^C$ are unsubstituted docosyl. In certain embodiments, all instances of $R^C$ are substituted docosyl. In certain embodiments, all instances of $R^C$ are fluorinated docosyl. In certain embodiments, all instances of $R^C$ are perfluorinated docosyl. In certain embodiments, all instances of $R^C$ are unsubstituted tricosyl. In certain embodiments, all instances of $R^C$ are substituted tricosyl. In certain embodiments, all instances of $R^C$ are fluorinated tricosyl. In certain embodiments, all instances of $R^C$ are perfluorinated tricosyl. In certain embodiments, all instances of $R^C$ are unsubstituted tetracosyl. In certain embodiments, all instances of $R^C$ are substituted tetracosyl. In certain embodiments, all instances of $R^C$ are fluorinated tetracosyl. In certain embodiments, all instances of $R^C$ are perfluorinated tetracosyl.

In certain embodiments, at least one instance of n is 1. In certain embodiments, at least one instance of n is 2. In certain embodiments, at least one instance of n is 3. In certain embodiments, at least one instance of n is 4. In certain embodiments, at least one instance of n is 5.

In certain embodiments, at least two instances of n are 1. In certain embodiments, at least two instances of n are 2. In certain embodiments, at least two instances of n are 3. In certain embodiments, at least two instances of n are 4. In certain embodiments, at least two instances of n are 5.

In certain embodiments, at least three instances of n are 1. In certain embodiments, at least three instances of n are 2. In certain embodiments, at least three instances of n are 3. In certain embodiments, at least three instances of n are 4. In certain embodiments, at least three instances of n are 5.

In certain embodiments, at least four instances of n are 1. In certain embodiments, at least four instances of n are 2. In certain embodiments, at least four instances of n are 3. In certain embodiments, at least four instances of n are 4. In certain embodiments, at least four instances of n are 5.

In certain embodiments, at least five instances of n are 1. In certain embodiments, at least five instances of n are 2. In certain embodiments, at least five instances of n are 3. In certain embodiments, at least five instances of n are 4. In certain embodiments, at least five instances of n are 5.

In certain embodiments, all instances of n are 1. In certain embodiments, all instances of n are 2. In certain embodiments, all instances of n are 3. In certain embodiments, all instances of n are 4. In certain embodiments, all instances of n are 5.

In certain embodiments, all instances of $R^C$ are unsubstituted alkyl; and all instances of n are 1. In certain embodiments, all instances of $R^C$ are unsubstituted $C_{1-24}$ alkyl; and all instances of n are 1. In certain embodiments, all instances of $R^C$ are unsubstituted $C_{6-24}$ alkyl; and all instances of n are 1. In certain embodiments, all instances of $R^C$ are unsubstituted $C_{12-24}$ alkyl; and all instances of n are 1.

In another aspect, the present invention provides compounds of any one of Formulae (III-1)-(III-3):

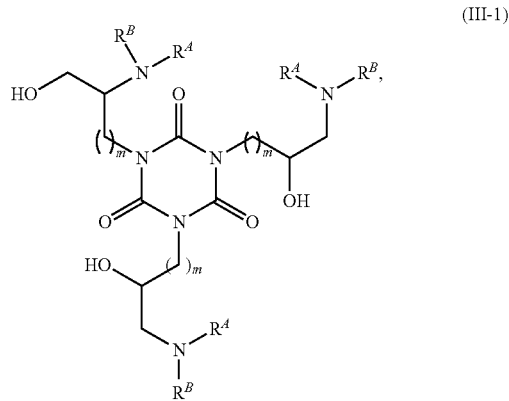

(III-1)

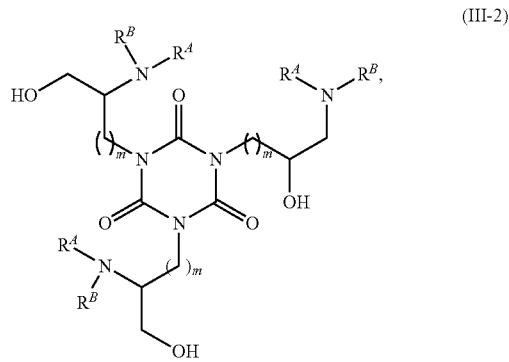

(III-2)

-continued

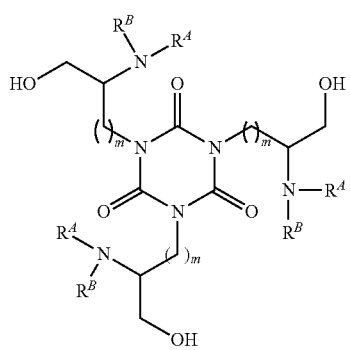

(III-3)

and salts thereof, wherein $R^A$, $R^B$, and m are as described herein.

In certain embodiments, provided are compounds of any one of Formulae (III-1)-(III-3), and pharmaceutically acceptable salts thereof.

In certain embodiments, provided are compounds of the formula:

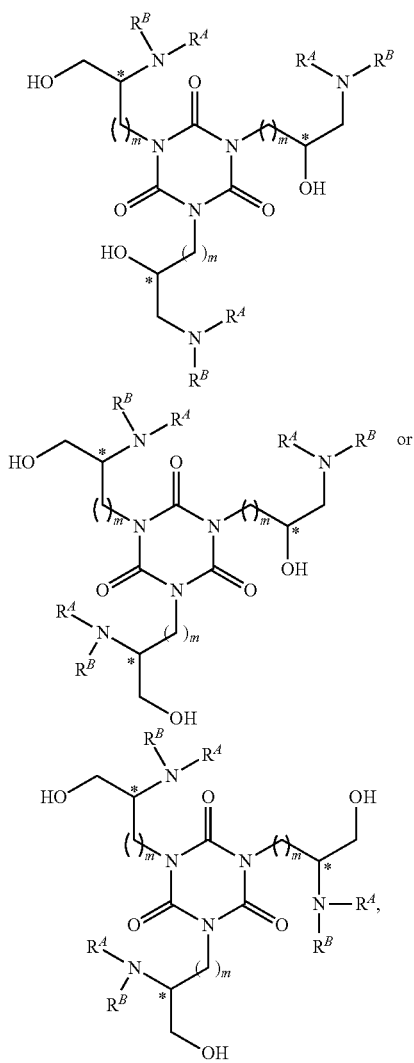

wherein the stereochemistry of each one of the carbon atoms labeled with "*" is independently S or R. In certain embodiments, the compounds of any one of Formulae (III-1)-(III-3) are a mixture of stereoisomers. In certain embodiments, the mixture of stereoisomers is racemic.

In another aspect, the present invention provides compounds of Formula (IV):

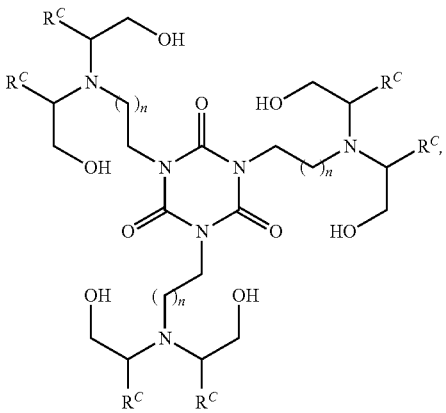

(IV)

and salts thereof, wherein $R^C$ and n are as described herein.

In certain embodiments, provided are compounds of Formula (IV), and pharmaceutically acceptable salts thereof.

In certain embodiments, the compound of Formula (IV) is of the formula:

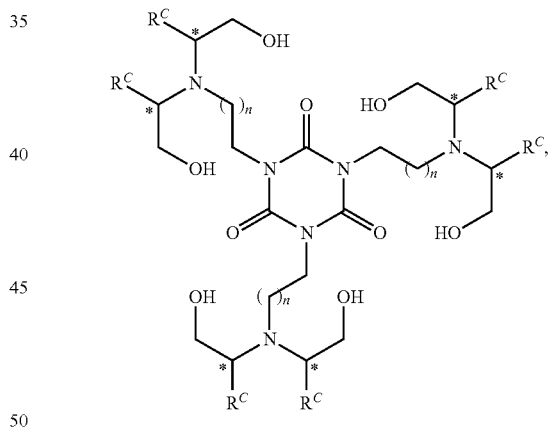

wherein the stereochemistry of each one of the six carbon atoms labeled with "*" is independently S or R. In certain embodiments, the compounds of Formula (IV) are a mixture of stereoisomers. In certain embodiments, the mixture of stereoisomers is racemic.

In certain embodiments, the compounds of the invention are not a dendrimer. In certain embodiments, the compounds of the invention do not include a substituted or unsubstituted, branched or unbranched, alkenyl moiety. In certain embodiments, the compounds of the invention do not include a sulfur moiety. In certain embodiments, the compounds of the invention do not include an aryl moiety (e.g., phenyl). In certain embodiments, no instance of $R^A$ and $R^B$ of compounds of any one of Formulae (I) and (III-1)-(III-3) includes an oxo group. In certain embodiments, no instance of $R^C$ of compounds of Formula (II) or (IV) includes an oxo group.

The compounds of the invention or, in other words, the inventive compounds, include the compounds described herein (e.g., compounds of any one of Formulae (I)-(IV)), and salts thereof. In certain embodiments, the compounds of the invention are compounds of Formula (I), and salts thereof. In certain embodiments, the compounds of the invention are compounds of Formula (II), and salts thereof. The compounds of the invention may be useful in treating and/or preventing a disease (e.g., a genetic disease, proliferative disease, hematological disease, neurological disease, liver disease, spleen diseases, and lung disease) in a subject in need thereof. In certain embodiments, the inventive compounds are useful in gene therapy. For example, the compounds of the invention may be useful in delivering an agent, such as a polynucleotide (e.g., an siRNA, mRNA, plasmid DNA, or a combination thereof), to a subject in need thereof.

Compositions

The present invention provides compositions comprising a compound of the invention (e.g., a compound of any one of Formulae (I)-(II), or a salt thereof), an agent (e.g., an agent or diagnostic agent), and optionally an excipient. In certain embodiments, the compositions of the invention are compositions. In certain embodiments, the compositions are compositions for non-medical applications. In certain embodiments, the compositions are cosmetic compositions. In certain embodiments, the compositions are dietary compositions. In certain embodiments, the compositions are nutraceutical compositions. In certain embodiments, a composition of the invention comprises a compound of Formula (I), or a salt thereof, and optionally an excipient. In certain embodiments, a composition of the invention comprises a compound of Formula (I), or a pharmaceutically acceptable salt thereof, and optionally a pharmaceutically acceptable excipient. In certain embodiments, a composition of the invention comprises a compound of Formula (II), or a salt thereof, and optionally an excipient. In certain embodiments, a composition of the invention comprises a compound of Formula (II), or a pharmaceutically acceptable salt thereof, and optionally a pharmaceutically acceptable excipient.

The compositions of the invention comprise one or more agents. The agents are described in more detail herein. In an inventive composition, an agent may form a complex with a compound of the invention. The complexes are described in more detail herein. In certain embodiments, the composition is useful in the delivery of the agent to a subject in need thereof. In certain embodiments, the composition is useful in the delivery of an effective amount of the agent to the subject. In certain embodiments, the agent is covalently attached to the compound of the invention in the inventive composition. In certain embodiments, the agent is not covalently attached to the compound of the invention in the inventive composition.

The inventive compositions comprising an agent may improve or increase the delivery of the agent to a subject or cell. In certain embodiments, the compositions of the invention increase the delivery of the agent to a target tissue of the subject. In certain embodiments, the compositions selectively deliver the agent to the target tissue (e.g., the compositions deliver more agent to the target tissue than to a non-target tissue. In certain embodiments, the compositions increase the delivery of the agent to the liver of the subject. In certain embodiments, the compositions increase the delivery of the agent to the spleen of the subject. In certain embodiments, the compositions increase the delivery of the agent to the lung of the subject. In certain embodiments, the compositions selectively deliver the agent to the liver, spleen, and/or lung of the subject.

The delivery of the agent may be characterized in various ways, such as the exposure, concentration, and bioavailability of the agent. The exposure of an agent in a subject may be defined as the area under the curve (AUC) of the concentration of the agent in the subject or cell after administration or dosing. In certain embodiments, the exposure described herein is the exposure of the agent in a target tissue (e.g., liver, spleen, or lung) of the subject. In general, an increase in exposure may be calculated by taking the difference in the AUC measured in a subject or cell between those of an inventive composition and a control composition, and dividing the difference by the exposure of the control composition. Exposure of an agent may be measured in an appropriate animal model. The concentration of an agent and, when appropriate, its metabolite(s), in a subject or cell is measured as a function of time after administration.

In certain embodiments, the concentration described herein is the concentration of the agent in a target tissue (e.g., liver, spleen, or lung) of the subject. Concentration of an agent, and, when appropriate, of its metabolite(s), in a subject or cell, may be measured as a function of time in vivo using an appropriate animal model. One method of determining the concentration of an agent involves dissecting of a tissue or organ of the subject. The concentration of the agent in the subject or cell may be determined by HPLC or LC/MS analysis.

In some embodiments, the delivery of the agent increases due to the presence of an inventive compound in the composition. In some embodiments, the delivery of the agent increases due to the presence of a complex formed between an inventive compound and the agent in the composition. In some embodiments, the compositions of the invention increase the delivery of the agent by at least about 10%, at least about 20%, at least about 30%, at least about 40%, at least about 50%, at least about 100%, at least about 2-fold, at least about 3-fold, at least about 10-fold, at least about 30-fold, at least about 100-fold, at least about 300-fold, or at least about 1000-fold. In certain embodiments, the compositions of the invention increase the delivery of the agent by less than about 1000-fold, less than about 300-fold, less than about 100-fold, less than about 30-fold, less than about 10-fold, less than about 3-fold, less than about 2-fold, less than about 100%, less than about 50%, less than about 30%, less than about 20%, or less than about 10%. Combinations of the above-referenced ranges are also possible (e.g., an increase of at least about 100% and less than about 10 fold). Other ranges are also within the scope of the invention. In certain embodiments, a compound of the invention is present in the composition in a sufficient amount to increase the delivery of the agent by an amount described herein when administered in the composition compared to the delivery of the agent when administered in the absence of a compound of the invention.

The compositions of the invention may deliver an agent selectively to a tissue or organ of a subject. In certain embodiments, the tissue or organ to which the agent is selectively delivered to is a target tissue. In certain embodiments, the compositions deliver at least about 10%, at least about 20%, at least about 30%, at least about 40%, at least about 50%, at least about 70%, at least about 100%, at least about 3-fold, at least about 10-fold, at least about 30-fold, at least about 100-fold, at least about 300-fold, or at least about 1000-fold more amount of the agent to a target tissue than to a non-target tissue. The amount of agent may be measured by the exposure, concentration, and/or bioavailability of the agent in a tissue or organ as described herein. In certain embodiments, the compositions deliver at most about 1000-fold, at most about 300-fold, at most about 100-fold, at most about 30-fold, at most about 10-fold, at most about 3-fold, at most about 100%, at most about 70%, at most about 50%, at most about 40%, at most about 30%, at most about 20%, or at most about 10% more amount of the agent to a target tissue than to a non-target tissue. Combinations of the above ranges (e.g., at least about 100% and at most about 10 fold) are also with the scope of the invention. In certain embodiments, the target tissue is the liver. In certain embodiments, the target tissue is the spleen. In certain embodiments, In certain embodiments, the target tissue is the lung.

The inventive compositions (e.g., pharmaceutical compositions) including one or more agents (e.g., pharmaceutical agents) may be useful in treating and/or preventing a disease. In certain embodiments, the compositions are useful in gene therapy. In certain embodiments, the compositions are useful for treating and/or preventing a genetic disease. In certain embodiments, the compositions are useful for treating and/or preventing a proliferative disease. In certain embodiments, the compositions are useful for treating and/or preventing cancer. In certain embodiments, the compositions are useful for treating and/or preventing a benign neoplasm. In certain embodiments, the compositions are useful for treating and/or preventing pathological angiogenesis. In certain embodiments, the compositions are useful for treating and/or preventing an inflammatory disease. In certain embodiments, the compositions are useful for treating and/or preventing an autoimmune disease. In certain embodiments, the compositions are useful for treating and/or preventing a hematological disease. In certain embodiments, the compositions are useful for treating and/or preventing a neurological disease. In certain embodiments, the compositions are useful for treating and/or preventing a liver disease. In certain embodiments, the compositions are useful for treating and/or preventing a spleen disease. In certain embodiments, the compositions are useful for treating and/or preventing a lung disease. In certain embodiments, the compositions are useful for treating and/or preventing hepatic carcinoma, hypercholesterolemia, refractory anemia, or familial amyloid neuropathy.

The agents may be provided in an effective amount in a composition of the invention. In certain embodiments, the effective amount is a therapeutically effective amount. In certain embodiments, the effective amount is a prophylactically effective amount. In certain embodiments, the effective amount is an amount effective for treating and/or preventing a disease. In certain embodiments, the effective amount is an amount effective for treating a disease. In certain embodiments, the effective amount is an amount effective for treating and/or preventing a genetic disease. In certain embodiments, the effective amount is an amount effective for treating and/or preventing a proliferative disease. In certain embodiments, the effective amount is an amount effective for treating and/or preventing cancer. In certain embodiments, the effective amount is an amount effective for treating and/or preventing a benign neoplasm. In certain embodiments, the effective amount is an amount effective for treating and/or preventing pathological angiogenesis. In certain embodiments, the effective amount is an amount effective for treating and/or preventing an inflammatory disease. In certain embodiments, the effective amount is an amount effective for treating and/or preventing an autoimmune disease. In certain embodiments, the effective amount is an amount effective for treating and/or preventing a hematological disease. In certain embodiments, the effective amount is an amount effective for treating and/or preventing a neurological disease. In certain embodiments, the effective amount is an amount effective for treating and/or preventing a liver disease/ In certain embodiments, the effective amount is an amount effective for treating and/or preventing a spleen disease. In certain embodiments, the effective amount is an amount effective for treating and/or preventing a lung disease. In certain embodiments, the effective amount is an amount effective for treating and/or preventing hepatic carcinoma, hypercholesterolemia, refractory anemia, or familial amyloid neuropathy.

An effective amount of an agent may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In certain embodiments, the compositions of the invention are in the form of a particle. In certain embodiments, the particle is a nanoparticle or microparticle. In certain embodiments, the compositions are in the form of liposomes or micelles. It is understood that, in certain embodiments, the particles, micelles, or liposomes described herein result from self-assembly of the components of the composition. In certain embodiments, the particle, micelle, or liposome encapsulates an agent. The agent to be delivered by the particle, micelle, or liposome may be in the form of a gas, liquid, or solid. The compounds of the invention may be combined with polymers (synthetic or natural), surfactants, cholesterol, carbohydrates, proteins, lipids, lipidoids, etc. to form the particles. These particles may be further combined with an excipient to form the compositions of the invention. The particles, micelles, and liposomes are described in more detail herein.

The compositions described herein (e.g., pharmaceutical compositions) can be prepared by any method known in the art (e.g., pharmacology). In general, such preparatory methods include the steps of bringing a compound of the invention into association with an agent described herein (i.e., the "active ingredient"), optionally with a carrier or excipient, and/or one or more other accessory ingredients, and then, if necessary and/or desirable, shaping, and/or packaging the product into a desired single- or multi-dose unit.

Compositions can be prepared, packaged, and/or sold in bulk, as a single unit dose, and/or as a plurality of single unit doses. As used herein, a "unit dose" is a discrete amount of the composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the excipient (e.g., the pharmaceutically or cosmetically acceptable excipient), and/or any additional ingredients in a composition of the invention will vary, depending upon the identity, size, and/or condition of the subject treated and further depending upon the route by which the composition is to be administered. The composition may comprise between 0.1% and 100% (w/w) active ingredient.

Excipients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, German® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Additionally, the composition may further comprise an apolipoprotein. Previous studies have reported that Apolipoprotein E (ApoE) was able to enhance cell uptake and gene silencing for a certain type of materials. See, e.g., Akinc, A., et al., *Targeted delivery of RNAi therapeutics with endogenous and exogenous ligand-based mechanisms*. Mol Ther. 18(7): p. 1357-64. In certain embodiments, the apolipoprotein is ApoA, ApoB, ApoC, ApoE, or ApoH, or an isoform thereof.

Liquid dosage forms for oral and parenteral administration include emulsions, microemulsions, solutions, suspensions, syrups and elixirs. In certain embodiments, the emulsions, microemulsions, solutions, suspensions, syrups and elixirs are or cosmetically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, excipient or carrier (e.g., pharmaceutically or cosmetically acceptable excipient or carrier) such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the formulation art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a composition of this invention may include ointments, pastes, creams, lotions, gels, powders, solutions, sprays, inhalants, and/or patches. Generally, the active ingredient is admixed under sterile conditions with a carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the agent in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this invention.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, a composition of the invention is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an agent for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an agent per unit dosage form.

In certain embodiments, the agents described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided compositions to an adult. The amount to be administered to, for example, a child or an adolescent can be determined by a medical practitioner or person skilled in the art and can be lower or the same as that administered to an adult.

The compositions of the invention may include a hydrophilic polymer (e.g., polyethylene glycol (PEG)) and/or a lipid (e.g., a triglyceride, a driglyceride, a PEGylated lipid, a phospholipid (e.g., 1,2-distearoyl-sn-glycero-3-phosphocholine (DSPC)), a cholesterol, a apolipoprotein, or a combination thereof) in addition to a compound of the invention and an agent described herein. In certain embodiments, the compositions include two components selected from the group consisting of the following components: a hydrophilic polymer, a triglyceride, a driglyceride, a PEGylated lipid, a phospholipid, a cholesterol, and a apolipoprotein. In certain embodiments, the compositions include three components selected from the group consisting of the following components: a hydrophilic polymer, a triglyceride, a driglyceride, a PEGylated lipid, a phospholipid, a cholesterol, and a apolipoprotein. In certain embodiments, the compositions include at least four components selected from the group consisting of the following components: a hydrophilic polymer, a triglyceride, a driglyceride, a PEGylated lipid, a phospholipid, a cholesterol, and a apolipoprotein. In certain embodiments, the compositions include a hydrophilic polymer, a phospholipid, and a cholesterol. In certain embodiments, the compositions include PEG, DSPC, and cholesterol.

The compositions of the invention may be useful in other applications, e.g., non-medical applications. Nutraceutical compositions of the invention may be useful in the delivery of an effective amount of a nutraceutical, e.g., a dietary supplement, to a subject in need thereof. Cosmetic compositions of the invention may be formulated as a cream, ointment, balm, paste, film, or liquid, etc., and may be useful in the application of make-up, hair products, and materials useful for personal hygiene, etc. Compositions of the invention may be useful for other non-medical applications, e.g., such as an emulsion, emulsifier, or coating, useful, for example, as a food component, for extinguishing fires, for disinfecting surfaces, for oil cleanup, etc.

Agents

Agents that are delivered by the systems (e.g., pharmaceutical compositions) described herein may be (e.g., therapeutic or prophylactic), diagnostic, cosmetic, or nutraceutical agents. Any chemical compound to be administered to a subject may be delivered using the complexes, picoparticles, nanoparticles, microparticles, micelles, or liposomes, described herein. The agent may be an organic molecule, inorganic molecule, nucleic acid, protein, peptide, polynucleotide, targeting agent, an isotopically labeled chemical compound, vaccine, an immunological agent, or an agent useful in bioprocessing. Any chemical compound to be administered to a subject or contacted with a cell may be delivered to the subject or cell using the compositions of the invention.

The agents included in the compositions of the invention may be independently selected from the group consisting of small molecules, organometallic compounds, polynucleotides, proteins, peptides, carbohydrates, monosaccharides, oligosaccharides, polysaccharides, nucleoproteins, mucoproteins, lipoproteins, small molecules linked to proteins, glycoproteins, steroids, nucleotides, oligonucleotides, polynucleotides, nucleosides, antisense oligonucleotides, lipids, hormones, vitamins, cells, metals, targeting agents, isotopically labeled chemical compounds, drugs (e.g., compounds approved for human or veterinary use by the U.S. Food and Drug Administration as provided in the Code of Federal Regulations), vaccines, immunological agents, and agents useful in bioprocessing. The targeting agents are described in more detail herein. In certain embodiments, the agents are nutraceutical agents. In certain embodiments, the agents are agents. In certain embodiments, the agent is a therapeutic or prophylactic agent. In certain embodiments, the agent is an antibiotic agent (e.g., anti-bacterial agent, anti-viral agent, anti-fungal agent), anesthetic, steroidal agent, anti-proliferative agent, anti-inflammatory agent, anti-angiogenesis agent, anti-neoplastic agent, anti-cancer agent, anti-diabetic agent, antigen, vaccine, antibody, decongestant, antihypertensive, sedative, birth control agent, progestational agent, anti-cholinergic, analgesic, immunosuppressant, anti-depressant, anti-psychotic, β-adrenergic blocking agent, diuretic, cardiovascular active agent, vasoactive agent, non-steroidal, nutritional agent, anti-allergic agent, or pain-relieving agent. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, and Freund's adjuvant, etc.

In certain embodiments, the agents include a polynucleotide. In certain embodiments, the agents include a DNA or RNA. In certain embodiments, the agents include a plasmid DNA (pDNA), small interfering RNA (siRNA), double-stranded RNA (dsRNA), small hairpin RNA (shRNA), microRNA (miRNA), messenger RNA (mRNA), transfer RNA (tRNA), or antisense RNA (asRNA). In certain embodiments, the agents include a pDNA. In certain embodiments, the agent is an RNA that carries out RNA interference (RNAi). The phenomenon of RNAi is discussed in greater detail, for example, in the following references: Elbashir et al., 2001, *Genes Dev.*, 15:188; Fire et al., 1998, *Nature*, 391: 806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, the agents include an siRNA. In certain embodiments, the agents include a dsRNA. In certain embodiments, the agents include an shRNA. In certain embodiments, the agents include an miRNA. miRNAs are genomically encoded noncoding RNAs of about 21-23 nucleotides in length that help regulate gene expression, particularly during development. See, e.g., Bartel, 2004, *Cell*, 116:281; Novina and Sharp, 2004, *Nature*, 430:161; and U.S. Patent Application Publication, US 2005/0059005; Wang et al., 2007, *Front. Biosci.*, 12:3975; and Zhao, 2007, *Trends Biochem. Sci.*, 32:189. In certain embodiments, the agents include an mRNA. In certain embodiments, the agents include a tRNA. In certain embodiments, the agents include an asRNA. In certain embodiments, the agents include a combination of pDNA and siRNA. In certain embodiments, upon delivery of an RNA into a subject or cell, the RNA is able to interfere with the expression of a specific gene in the subject or cell.

In certain embodiments, the polynucleotide may be provided as an antisense agent or RNAi. See, e.g., Fire et al., *Nature* 391:806-811, 1998. Antisense therapy is meant to include, e.g., administration or in situ provision of single- or double-stranded polynucleotides, or derivatives thereof, which specifically hybridize, e.g., bind, under cellular conditions, with cellular mRNA and/or genomic DNA, or mutants thereof, so as to inhibit the expression of the encoded protein, e.g., by inhibiting transcription and/or translation. See, e.g., Crooke, "Molecular mechanisms of action of antisense drugs," *Biochim. Biophys. Acta* 1489(1):31-44, 1999; Crooke, "Evaluating the mechanism of action of anti-proliferative antisense drugs," *Antisense Nucleic Acid Drug Dev.* 10(2):123-126, discussion 127, 2000; *Methods in Enzymology volumes* 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

In some embodiments, pDNA, siRNA, dsRNA, shRNA, miRNA, mRNA, tRNA, asRNA, and/or RNAi can be designed and/or predicted using one or more of a large number of available algorithms. To give but a few examples, the following resources can be utilized to design and/or predict polynucleotides: algorithms found at Alnylum Online; Dharmacon Online; OligoEngine Online; Molecula Online; Ambion Online; BioPredsi Online; RNAi Web Online; Chang Bioscience Online; Invitrogen Online; LentiWeb Online GenScript Online; Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271.

The polynucleotide included in a composition of the invention may be of any size or sequence, and they may be single- or double-stranded. In certain embodiments, the polynucleotide includes at least about 30, at least about 100, at least about 300, at least about 1,000, at least about 3,000, or at least about 10,000 base pairs. In certain embodiments, the polynucleotide includes less than about 10,000, less than about 3,000, less than about 1,000, less than about 300, less than about 100, or less than about 30 base pairs. Combinations of the above ranges (e.g., at least about 100 and less than about 1,000) are also within the scope of the invention. The polynucleotide may be provided by any means known in the art. In certain embodiments, the polynucleotide is engineered using recombinant techniques. See, e.g., Ausubel et al., *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry. The polynucleotide may be isolated and/or purified. In certain embodiments, the polynucleotide is substantially free of impurities. In certain embodiments, the polynucleotide is at least about 50%, at least about 60%, at least about 70%, at least about 80%, at least about 90%, at least about 95%, or at least about 99% free of impurities.

The polynucleotide may be modified by physical, chemical, and/or biological means. The modifications include methylation, phosphorylation, and end-capping, etc. In certain embodiments, the modifications lead to increased stability of the polynucleotide.

Wherever a polynucleotide is employed in the present invention, a derivative of the polynucleotide may also be used. These derivatives include products resulted from modifications of the polynucleotide in the base moieties, sugar moieties, and/or phosphate moieties of the polynucleotide. Modified base moieties include, but are not limited to, 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugar moieties include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in the art, the modified polynucleotides may be prepared using synthetic chemistry in vitro.

The polynucleotide described herein may be in any form, such as a circular plasmid, a linearized plasmid, a cosmid, a viral genome, a modified viral genome, and an artificial chromosome.

The polynucleotide described herein may be of any sequence. In certain embodiments, the polynucleotide encodes a protein or peptide. The encoded protein may be an enzyme, structural protein, receptor, soluble receptor, ion channel, active (e.g., pharmaceutically active) protein, cytokine, interleukin, antibody, antibody fragment, antigen, coagulation factor, albumin, growth factor, hormone, and insulin, etc. The polynucleotide may also comprise regulatory regions to control the expression of a gene. These regulatory regions may include, but are not limited to, promoters, enhancer elements, repressor elements, TATA boxes, ribosomal binding sites, and stop sites for transcription, etc. In certain embodiments, the polynucleotide is not intended to encode a protein. For example, the polynucleotide may be used to fix an error in the genome of the cell being transfected.

In certain embodiments, the polynucleotide described herein comprises a sequence encoding an antigenic peptide or protein. A composition containing the polynucleotide can be delivered to a subject to induce an immunologic response sufficient to decrease the chance of a subsequent infection and/or lessen the symptoms associated with such an infection. The polynucleotide of these vaccines may be combined with interleukins, interferon, cytokines, and/or adjuvants described herein.

The antigenic protein or peptides encoded by the polynucleotide may be derived from such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; from such viruses as smallpox virus, influenza A virus, influenza B virus, respiratory syncytial virus, parainfluenza virus, measles virus, HIV virus, varicella-zoster virus, herpes simplex 1 virus, herpes simplex 2 virus, cytomegalovirus, Epstein-Ban virus, rotavirus, rhinovirus, adenovirus, papillomavirus, poliovirus, mumps virus, rabies virus, rubella virus, coxsackieviruses, equine encephalitis virus, Japanese encephalitis virus, yellow fever virus, Rift Valley fever virus, hepatitis A virus, hepatitis B virus, hepatitis C virus, hepatitis D virus, hepatitis E virus, and the like; and from such fungal, protozoan, and parasitic organisms such as *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

In certain embodiments, the agent in a composition of the invention that is delivered to a subject in need thereof may be a mixture of two or more agents that may be useful as, e.g., combination therapies. The compositions including the two or more agents can be administered to achieve a synergistic effect. In certain embodiments, the compositions including the two or more agents can be administered to improve the activity and/or bioavailability, reduce and/or modify the metabolism, inhibit the excretion, and/or modify the distribution within the body of a subject, of each one of the two or more agents. It will also be appreciated that the therapy employed may achieve a desired effect for the same disorder, and/or it may achieve different effects.

The compositions (e.g., pharmaceutical compositions) of the invention can be administered concurrently with, prior to, or subsequent to the one or more agents (e.g., pharmaceutical agents). The two or more agents may be useful for treating and/or preventing a same disease or different diseases described herein. Each one of the agents may be administered at a dose and/or on a time schedule determined for that agent. The agents may also be administered together with each other and/or with the composition described herein in a single dose or administered separately in different doses. The particular combination to employ in a regimen will take into account compatibility of the agents and/or the desired therapeutic and/or prophylactic effect to be achieved. In general, it is expected that the agents utilized in combination be utilized at levels that do not exceed the levels at which they are utilized individually. In some embodiments, the levels utilized in combination will be lower than those utilized individually.

Targeting Agents

Since it is often desirable to target a particular cell, collection of cells, or tissue, compounds of the invention, and the complexes, liposomes, micelles, ad particles (e.g., microparticles and nanoparticles) thereof, may be modified to include targeting moieties. For example, the compounds of the invention may include a targeting moiety. A variety of agents or regions that target particular cells are known in the art. See, e.g., Cotten et al., *Methods Enzym*. 217:618, 1993. The targeting agent may be included throughout a particle of a compound of the invention or may be only on the surface of the particle. The targeting agent may be a protein, peptide, carbohydrate, glycoprotein, lipid, small molecule, or polynucleotide, etc. The targeting agent may be used to target specific cells or tissues or may be used to promote endocytosis or phagocytosis of the particle. Examples of targeting agents include, but are not limited to, antibodies, fragments of antibodies, proteins, peptides, carbohydrates, receptor ligands, sialic acid, and aptamers, etc. If the targeting agent is included throughout a particle, the targeting agent may be included in the mixture that is used to form the particle. If the targeting agent is only on the surface of a particle, the targeting agent may be associated with (e.g., by covalent or non-covalent (e.g., electrostatic, hydrophobic, hydrogen bonding, van der Waals, π-π stacking) interactions) the formed particle using standard chemical techniques.

Complexes of an Agent and a Compound of the Invention

The present invention contemplates that the compounds of the invention are useful in the delivery of one or more agents (such as a polynucleotide (e.g., DNA (e.g., pDNA) or RNA (e.g., siRNA, mRNA), synthetic analogs of DNA and/or RNA, and DNA/RNA hybrids, etc.)) to a subject in need thereof. Without wishing to be bound by any particular theory, the compounds of the invention have several desirable properties that make a composition including the inventive compound and an agent suitable for delivering the agent to a subject in need thereof. The desirable properties include: 1) the ability of the inventive compound to complex with and "protect" the agent that may otherwise be labile; 2) the ability of the inventive compound to buffer the pH in an endosome of a cell of the subject; 3) the ability of the inventive compound to act as a "proton sponge" and cause endosomolysis; and 4) the ability of the inventive compound to substantially neutralize the negative charges of the agent.

A compound of the invention and an agent may form a complex in a composition of the invention. For example, a compound of the invention comprises secondary or tertiary amino moieties, which may be useful in enhancing the ability of an inventive composition including an agent (such as a polynucleotide) to deliver the agent to a subject (e.g., into a cell of the subject) in need thereof. The amino moieties, sterically hindered or not, may non-covalently interact with a polynucleotide. A polynucleotide may be contacted with a compound of the invention under conditions suitable to form a complex. In certain embodiments, the polynucleotide binds to a compound of the invention to form a complex through one or more non-covalent interactions described herein. In certain embodiments, the polynucleotide binds to a compound of the invention to form a complex through electrostatic interactions. Without wishing to be bound by any particular theory, one or more amino moieties of an inventive compound may be positively charged, and the polynucleotide (e.g., the monophosphate, diphosphate, and/or triphosphate moieties of the polynucleotide) may be negatively charged, when a compound of the invention, or a composition thereof, is delivered to a subject in need thereof (e.g., when the compound, or a composition thereof, is delivered to the subject at the physiological pH). The polynucleotide may bind to a compound of the invention to form a complex through electrostatic interactions between the negative charges of the inventive compound and the positive charges of the polynucleotide. By substantially neutralizing the charges (e.g., negative charges) of the polynucleotide, the resulting complex may be able to more easily pass through the hydrophobic membranes (e.g., cytoplasmic, lysosomal, endosomal, nuclear) of a cell, compared to a polynucleotide whose charges are not neutralized. In certain embodiments, the complex is substantially neutral. In certain embodiments, the complex is slightly positively charged. In certain embodiments, the complex has a positive ζ-potential. In certain embodiments the ζ-potential is between 0 and +30.

The compounds of the invention include unsubstituted or substituted alkyl moieties on the amino moieties. The alkyl moieties are hydrophobic and may be useful in enhancing the ability of an inventive composition including an agent (such as a polynucleotide) to deliver the agent to a subject (e.g., into a cell of the subject) in need thereof. For example, the hydrophobic alkyl moieties may assist a complex of an inventive compound and a polynucleotide to more easily pass through cell membranes, which are also hydrophobic, compared to a polynucleotide, which is typically hydrophilic.

Polynucleotides may be degraded chemically and/or enzymatically (e.g., by nucleases and nucleotidases). The interaction of a compound of the invention with the polynucleotide is thought to at least partially prevent the degradation of the polynucleotide.

A compound of the invention may be at least partially provided as a salt (e.g., being protonated) so as to form a complex with a negatively charged agent (e.g., a polynucleotide). In certain embodiments, the complex form particles that are useful in the delivery of the agent to a subject. In certain embodiments, more than one inventive compound may be associated with an agent. For example, the complex may include 1-10, 1-100, 1-1,000, 10-1,000, 100-1,000, or 100-10,000 inventive compounds associated with an agent.

The ratio of the amount of a compound of the invention to the amount of an agent (e.g., a polynucleotide) in an inventive composition including the compound and agent (e.g., as a complex) may be adjusted so that the agent may be more efficiently delivered to a subject in need thereof and/or the toxicity of the composition is decreased. In certain embodiments, the ratio of the inventive compound to the agent is at least about 1:1, at least about 2:1, at least about 5:1, at least about 10:1, at least about 20:1, at least about 50:1, at least about 100:1, at least about 200:1, or at least about 500:1 mol/mol. In certain embodiments, the ratio of the inventive compound to the agent is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the invention.

The ratio of the amount of the amino moieties of a compound of the invention to the amount of the phosphate moieties of a polynucleotide (i.e., nitrogen:phosphate ratio) in an inventive composition including the compound and polynucleotide (e.g., as a complex) may also be adjusted so that the polynucleotide may be more efficiently delivered to a subject in need thereof and/or the toxicity of the composition is decreased. See, e.g., Incani et al., *Soft Matter* (2010) 6:2124-2138. In certain embodiments, the nitrogen:phosphate ratio is at least about 1:1, at least about 2:1, at least about 5:1, at least about 10:1, at least about 20:1, at least about 50:1, at least about 100:1, at least about 200:1, or at least about 500:1 mol/mol. In certain embodiments, the nitrogen:phosphate ratio is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the invention.

An agent described herein may be covalently or non-covalently (e.g., complexed or encapsulated) attached to a compound of the invention, or included in a composition comprising a compound of the invention. In certain embodiments, upon delivery of the agent into a cell of a subject in need thereof, the agent is able to interfere with the expression of a specific gene in the cell.

Particles

A composition including an inventive compound and an agent may be in the form of a particle. In certain embodiments, the inventive compound is in the form of a particle. In certain embodiments, the agent is in the form of a particle. In certain embodiments, the inventive compound and agent form a complex, and the complex is in the form of a particle. In certain embodiments, the inventive compound encapsulates the agent and is in the form of a particle. In certain embodiments, the inventive compound is mixed with the agent, and the mixture is in the form of a particle.

In certain embodiments, a complex of an inventive compound and an agent in a composition of the invention is in the form of a particle. In certain embodiments, the particle is a microparticle (i.e., a particle whose average diameter is at least 1 µm. In certain embodiments, the particle is a nanoparticle (i.e., a particle whose average diameter is less than 1 µm). In certain embodiments, the average diameter of the particle is at least about 10 nm, at least about 30 nm, at least about 100 nm, at least about 300 nm, at least about 1 µm, at least about 3 µm, at least about 10 µm, at least about 30 µm, at least about 100 µm, at least about 300 µm, or at least about 1 mm.

In certain embodiments, the average diameter of the particle is less than about 1 mm, less than about 300 µm, less than about 100 µm, less than about 30 µm less than about 10 µm, less than about 3 µm, less than about 1 µm, less than about 300 nm, less than about 100 nm, less than about 30 nm, or less than about 10 nm. Combinations of the above ranges (e.g., at least about 100 nm and less than about 1 µm) are also within the scope of the present invention.

The particles described herein may include additional materials such as polymers (e.g., synthetic polymers (e.g., PEG, PLGA) and natural polymers (e.g., phospholipids)). In certain embodiments, the additional materials are approved by a regulatory agency, such as the U.S. FDA, for human and veterinary use.

The particles may be prepared using any method known in the art, such as precipitation, milling, spray drying, single and double emulsion solvent evaporation, solvent extraction, phase separation, and simple and complex coacervation. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, polydispersity, etc.). The method of preparing the particle and the conditions (e.g., solvent, temperature, concentration, and air flow rate, etc.) used may also depend on the agent being complexed, encapsulated, or mixed, and/or the composition of the matrix.

Methods developed for making particles for delivery of agents that are included in the particles are described in the literature. See, e.g., Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988.

If the particles prepared by any of the above methods have a size range outside of the desired range, the particles can be sized, for example, using a sieve. The particles may also be coated. In certain embodiments, the particles are coated with a targeting agent. In certain embodiments, the particles are coated with a surface-altering agent. In some embodiments, the particles are coated to achieve desirable surface properties (e.g., a particular charge).

Micelles and Liposomes

A composition including an inventive compound and an agent may be in the form of a micelle or liposome. In certain embodiments, the inventive compound is in the form of a micelle or liposome. In certain embodiments, the agent is in the form of a micelle or liposome. In certain embodiments, the inventive compound and agent form a complex, and the complex is in the form of a micelle or liposome. In certain embodiments, the inventive compound encapsulates the agent and is in the form of a micelle or liposome. In certain embodiments, the inventive compound is mixed with the agent, and the mixture is in the form of a micelle or liposome. Micelles and liposomes are particularly useful in delivering an agent, such as a hydrophobic agent. When the micelle or liposome is complexed with (e.g., encapsulates or covers) a polynucleotide, the resulting complex may be referred to as a "lipoplex." Many techniques for preparing micelles and liposomes are known in the art, and any such method may be used herein to make micelles and liposomes.

In certain embodiments, liposomes are formed through spontaneous assembly. In some embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these liposomes have formed, reducing the size of the liposomes can be modified through input of sonic energy (sonication) or mechanical energy (extrusion). See, e.g., Walde, P. "Preparation of Vesicles (Liposomes)" In *Encylopedia of Nanoscience and Nanotechnology*; Nalwa, H. S. Ed. American Scientific Publishers Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein by reference. The preparation of liposomes may involve preparing a compound of the invention for hydration, hydrating the compound with agitation, and sizing the vesicles to achieve a homogenous distribution of liposomes. A compound of the invention may be first dissolved in an organic solvent in a container to result in a homogeneous mixture. The organic solvent is then removed to form a polymer-derived film. This polymer-derived film is thoroughly dried to remove residual organic solvent by placing the container on a vacuum pump for a period of time. Hydration of the polymer-derived film is accomplished by adding an aqueous medium and agitating the mixture. Disruption of LMV suspensions using sonic energy typically produces small unilamellar vesicles (SUV) with diameters in the range of 15-50 nm. Lipid extrusion is a technique in which a lipid/polymer suspension is forced through a polycarbonate filter with a defined pore size to yield particles having a diameter near the pore size of the filter used. Extrusion through filters with 100 nm pores typically yields large, unilamellar polymer-derived vesicles (LUV) with a mean diameter of 120-140 nm. In certain embodiments, the amount of a compound of the invention in the liposome ranges from about 30 mol % to about 80 mol %, from about 40 mol % to about 70 mol %, or from about 60 mol % to about 70 mol %. In certain embodiments, the inventive compound employed further complexes an agent, such as a polynucleotide. In such embodiments, the application of the liposome is the delivery of the polynucleotide.

The following scientific papers described other methods for preparing liposomes and micelles: Narang et al., "Cationic Lipids with Increased DNA Binding Affinity for Non-viral Gene Transfer in Dividing and Nondividing Cells," *Bioconjugate Chem.* 16:156-68, 2005; Hofland et al., "Formation of stable cationic lipid/DNA complexes for gene transfer," *Proc. Natl. Acad. Sci. USA* 93:7305-7309, July 1996; Byk et al., "Synthesis, Activity, and Structure—Activity Relationship Studies of Novel Cationic Lipids for DNA Transfer," *J. Med. Chem.* 41(2):224-235, 1998; Wu et al., "Cationic Lipid Polymerization as a Novel Approach for Constructing New DNA Delivery Agents," *Bioconjugate Chem.* 12:251-57, 2001; Lukyanov et al., "Micelles from lipid derivatives of water-soluble polymers as delivery systems for poorly soluble drugs," *Advanced Drug Delivery Reviews* 56:1273-1289, 2004; Tranchant et al., "Physicochemical optimisation of plasmid delivery by cationic lipids," *J. Gene Med.* 6:S24-S35, 2004; van Balen et al., "Liposome/Water Lipophilicity: Methods, Information Content, and Pharmaceutical Applications," *Medicinal Research Rev.* 24(3):299-324, 2004.

Kits

Also encompassed by the invention are kits (e.g., packs). The kits provided may comprise an inventive composition and a container (e.g., a vial, ampule, bottle, syringe, and/or dispenser package, or other suitable container). In some embodiments, provided kits may optionally further include a second container comprising an excipient for dilution or suspension of an inventive composition. In some embodiments, the inventive composition provided in the first container and the inventive composition provided in the second container are combined to form one unit dosage form.

Thus, in one aspect, provided are kits including a first container comprising a composition of the invention. In certain embodiments, the kits described herein are useful for delivering an agent to a subject or cell. In certain embodiments, the kits are useful for delivering an agent to a target tissue of a subject. In certain embodiments, the kits are useful for delivering an agent to the liver of a subject. In certain embodiments, the kits are useful for delivering an agent to the spleen of a subject. In certain embodiments, the kits are useful for delivering an agent to the lung of a subject. In certain embodiments, the kits are useful for selectively delivering an agent to the liver, spleen, and/or lung of a subject. In certain embodiments, the kits described herein are useful for preventing and/or treating a disease described herein. In certain embodiments, the kits are useful for preventing and/or treating a genetic disease. In certain embodiments, the kits are useful for preventing and/or treating a proliferative disease. In certain embodiments, the kits are useful for treating and/or preventing cancer. In certain embodiments, the kits are useful for treating and/or preventing a benign neoplasm. In certain embodiments, the kits are useful for treating and/or preventing pathological angiogenesis. In certain embodiments, the kits are useful for treating and/or preventing an inflammatory disease. In certain embodiments, the kits are useful for treating and/or preventing an autoimmune disease. In certain embodiments, the kits are useful for treating and/or preventing a hematological disease. In certain embodiments, the kits are useful for treating and/or preventing a neurological disease. In certain embodiments, the kits are useful for treating and/or preventing a liver disease. In certain embodiments, the kits are useful for treating and/or preventing a spleen disease. In certain embodiments, the kits are useful for treating and/or preventing a lung disease. In certain embodiments, the kits are useful for treating and/or preventing hepatic carcinoma, hypercholesterolemia, refractory anemia, or familial amyloid neuropathy.

In certain embodiments, the kits further include instructions for administering the composition. The kits may also include information as required by a regulatory agency such as the U.S. Food and Drug Administration (FDA). In certain embodiments, the information included in the kits is prescribing information. In certain embodiments, the kits, including the instructions, provide for treating and/or preventing a disease described herein. In certain embodiments, the kits, including the instructions, provide for preventing and/or treating a genetic disease. In certain embodiments, the kits, including the instructions, provide for preventing and/or treating a proliferative disease. In certain embodiments, the kits, including the instructions, provide for treating and/or preventing cancer. In certain embodiments, the kits, including the instructions, provide for treating and/or preventing a benign neoplasm. In certain embodiments, the kits, including the instructions, provide for treating and/or preventing pathological angiogenesis. In certain embodiments, the kits, including the instructions, provide for treating and/or preventing an inflammatory disease. In certain embodiments, the kits, including the instructions, provide for treating and/or preventing an autoimmune disease. In certain embodiments, the kits, including the instructions, provide for treating and/or preventing a hematological disease. In certain embodiments, the kits, including the instructions, provide for treating and/or preventing a neurological disease. In certain embodiments, the kits, including the instructions, provide for treating and/or preventing a liver disease. In certain embodiments, the kits, including the instructions, provide for treating and/or preventing a spleen disease. In certain embodiments, the kits, including the instructions, provide for treating and/or preventing a lung disease. In certain embodiments, the kits, including the instructions, provide for treating and/or preventing hepatic carcinoma, hypercholesterolemia, refractory anemia, or familial amyloid neuropathy. The kit of the invention may include one or more agents described herein as a separate composition.

Methods of Treatment and Uses

It is estimated that over 10,000 human diseases are caused by genetic disorders, which are abnormalities in genes or chromosomes. See, e.g., McClellan, J. and M. C. King, *Genetic heterogeneity in human disease*. Cell. 141(2): p. 210-7; Leachman, S. A., et al., *J. Dermatol. Sci.*, 2008. 51(3): p. 151-7. Many of these diseases are fatal, such as cancer, severe hypercholesterolemia, and familial amyloidotic polyneuropathy. See, e.g., Frank-Kamenetsky, M., et al., *Proc. Natl. Acad. Sci. U.S.A.* 2008. 105(33): p. 11915-20; Coelho, T., *Curr. Opin. Neurol.*, 1996. 9(5): p. 355-9. Since the discovery of gene expression silencing via RNA interference (RNAi) by Fire and Mello (Fire, A., et al., *Nature*, 1998. 391(6669): p. 806-11), there has been extensive effort toward developing therapeutic applications for RNAi in humans. See, e.g., Davis, M. E., *Mol. Pharm.* 2009. 6(3): p. 659-68; Whitehead, K. A., R. Langer, and D. G. Anderson, *Nat. Rev. Drug Discovery,* 2009. 8(2): p. 129-138; Tan, S. J., et al., *Small.* 7(7): p. 841-56; Castanotto, D. and J. J. Rossi, *Nature,* 2009. 457 (7228): p. 426-33; Chen, Y. and L. Huang, *Expert Opin. Drug Deliv.* 2008. 5(12): p. 1301-11; Weinstein, S, and D. Peer, *Nanotechnology.* 21(23): p. 232001; Fenske, D. B. and P. R. Cullis, *Expert Opin. Drug Deliv.* 2008. 5(1): p. 25-44; and Thiel, K. W. and P. H. Giangrande, *Oligonucleotides,* 2009. 19(3): p. 209-22. Currently, there are more than 20 clinical trials ongoing or completed involving siRNA therapeutics, which have shown promising results for the treatment of various diseases. See, e.g., Burnett, J. C., J. J. Rossi, and K. Tiemann, *Biotechnol. J.* 6(9): p. 1130-46. However, the efficient and safe delivery of siRNA is still a key challenge in the development of siRNA therapeutics. See, e.g., Juliano, R., et al., *Mol. Pharm.* 2009. 6(3): p. 686-95.

In one aspect, the present invention provides methods of delivering an agent described herein to a subject in need thereof or a cell. In certain embodiments, provided are methods of delivering the agent to a target tissue to the subject. In certain embodiments, provided are methods of delivering the agent to the liver of the subject. In certain embodiments, provided are methods of delivering the agent to the spleen of the subject. In certain embodiments, provided are methods of delivering the agent to the lung of the subject. In certain embodiments, provided are methods of selectively delivering the agent to the liver, spleen, and/or lung of the subject. In certain embodiments, provided are methods of delivering a polynucleotide to the subject or cell. In certain embodiments, provided are methods of delivering a DNA to the subject or cell. In certain embodiments, provided are methods of delivering a pDNA to the subject or cell. In certain embodiments, provided are methods of delivering an RNA to the subject or cell. In certain embodiments, provided are methods of delivering an siRNA to the subject or cell. In certain embodiments, provided are methods of delivering an mRNA to the subject or cell. In certain embodiments, the agent is delivered into a cell of the subject.

Another aspect of the invention relates to methods of increasing the delivery of an agent to a subject or cell.

In another aspect, the present invention provides methods of treating and/or preventing a disease. In certain embodiments, the disease that is treated and/or prevented by the inventive methods is a genetic disease. All types of genetic diseases described herein may be treated and/or prevented by the inventive methods. In certain embodiments, the disease that is treated and/or prevented by the inventive methods is cancer. All types of cancers described herein may be treated and/or prevented by the inventive methods. In certain embodiments, the disease that is treated and/or prevented by the inventive methods is a benign neoplasm. All types of benign neoplasms described herein may be treated and/or prevented by the inventive methods. In certain embodiments, the disease that is treated and/or prevented by the inventive methods is pathological angiogenesis. All types of pathological angiogenesis described herein may be treated and/or prevented by the inventive methods. In certain embodiments, the disease that is treated and/or prevented by the inventive methods is an inflammatory disease. All types of inflammatory diseases described herein may be treated and/or prevented by the inventive methods. In certain embodiments, the disease that is treated and/or prevented by the inventive methods is an autoimmune disease. All types of autoimmune diseases described herein may be treated and/or prevented by the inventive methods. In certain embodiments, the disease that is treated and/or prevented by the inventive methods is a hematological disease. All types of hematological diseases described herein may be treated and/or prevented by the inventive methods. In certain embodiments, the disease that is treated and/or prevented by the inventive methods is a neurological disease. All types of neurological diseases described herein may be treated and/or prevented by the inventive methods. In certain embodiments, the disease that is treated and/or prevented by the inventive methods is a liver disease. All types of liver diseases described herein may be treated and/or prevented by the inventive methods. In certain embodiments, the disease that is treated and/or prevented by the inventive methods is a spleen disease. All types of spleen diseases, described herein may be treated and/or prevented by the inventive methods. In certain embodiments, the disease that is treated and/or prevented by the inventive methods is a lung disease. All types of lung diseases described herein may be treated and/or prevented by the inventive methods. In certain embodiments, the disease that is treated and/or prevented by the inventive methods is a painful condition. All types of painful conditions described herein may be treated and/or prevented by the inventive methods. In certain embodiments, the disease that is treated and/or prevented by the inventive methods is hepatic carcinoma. In certain embodiments, the disease that is treated and/or prevented by the inventive methods is hypercholesterolemia. In certain embodiments, the disease that is treated and/or prevented by the inventive methods is refractory anemia. In certain embodiments, the disease that is treated and/or prevented by the inventive methods is familial amyloid neuropathy.

Another aspect of the invention relates to methods of genetically engineer a subject. In certain embodiments, the subject is genetically engineered to increase the growth of the subject. In certain embodiments, the subject is genetically engineered to increase the subject's resistance to pathogenic organisms and/or microorganisms (e.g., viruses, bacteria, fungi, protozoa, and parasites). In certain embodiments, the subject is genetically engineered to increase the subject's ability to grow under unfavorable conditions (such as unfavorable weather conditions, e.g., dryness, infertility, and/or extremely cold or extremely high temperature).

In certain embodiments, the methods of the invention comprise administering to the subject a composition of the invention. In certain embodiments, the methods of the invention comprise contacting the cell with a composition of the invention.

In certain embodiments, the subject described herein is a human. In certain embodiments, the subject is an animal. The animal may be of either sex and may be at any stage of development. In certain embodiments, the subject is a fish. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is a plant described herein.

In certain embodiments, the cell described herein is in vivo. In certain embodiments, the cell is in vitro. In certain embodiments, the cell is ex vitro.

In certain embodiments, the inventive methods are in vivo methods. In certain embodiments, the inventive methods are in vitro methods. In certain embodiments, the inventive methods are ex vitro methods.

In certain embodiments, the condition is a painful condition and, in certain embodiments, the composition further includes an analgesic agent. In certain embodiments, the painful condition is inflammatory pain. In certain embodiments, the painful condition (e.g., inflammatory pain) is associated with an inflammatory disorder and/or an autoimmune disorder.

Another aspect of the invention relates to methods of screening a library of compounds to identify one or more compounds that are useful in the methods of the invention. In certain embodiments, the methods of screening a library of compounds are useful in identifying one or more compounds with desired or undesired properties. In certain embodiments, the desired property is solubility in water, solubility at different pH, ability to bind polynucleotides, ability to bind heparin, ability to bind small molecules, ability to bind protein, ability to form microparticles, ability to increase transfection efficiency, ability to support cell growth, ability to support cell attachment, ability to support tissue growth, and/or intracellular delivery of an agent described herein and/or an agent complexed or attached thereto to aid in bioprocessing. In certain embodiments, the undesired prosperity is the lack of a desired prosperity. In certain embodiments, the one or more compounds identified are useful for treating and/or preventing a disease described herein. In certain embodiments, the library of compounds is a library of compounds of the invention. In certain embodiments, the methods of screening a library include providing at least two different compounds of the invention; and performing at least one assay using the different compounds of the invention, to identify one or more compounds that are useful in the inventive methods.

Typically, the methods of screening a library of compounds involve at least one assay. In certain embodiments, the assay is performed to detect one or more characteristics associated with the treatment and/or prevention of a disease described herein. The characteristics may be desired (e.g., a disease being treated and/or prevented) or undesired (e.g., a disease not being treated or prevented) characteristics. The assay may be an immunoassay, such as a sandwich-type assay, competitive binding assay, one-step direct test, two-step test, or blot assay. The step of performing at least one assay may be performed robotically or manually.

In another aspect, the present invention provides the compounds and compositions of the invention for use in the treatment and/or prevention of a disease described herein in a subject in need thereof.

Methods of Preparing the Compounds

The present invention also provides methods of preparing the compounds of the invention. In one aspect, provided are methods of preparing the compounds of Formula (I), and salts thereof, the methods comprising reacting a compound of Formula (A), or a solvate, hydrate, polymorph, co-crystal, tautomer, stereoisomer, or isotopically labeled derivative thereof, with a compound of Formula (B), or a salt thereof, to provide a compound of Formula (I), or a salt thereof:

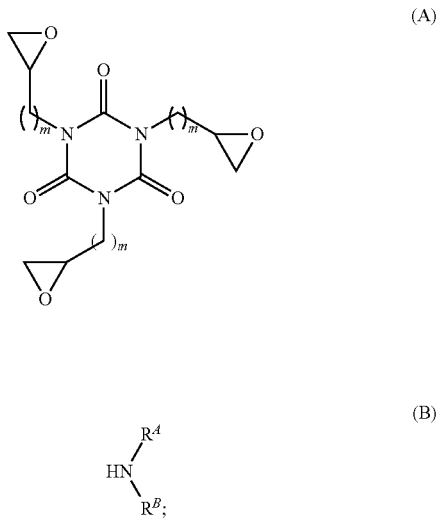

wherein $R^A$, $R^B$, and m are as described herein.

In another aspect, the present invention provides methods of preparing the compounds of Formula (II), and salts thereof, the methods comprising reacting a compound of Formula (C), or a salt, solvate, hydrate, polymorph, co-crystal, tautomer, isotopically labeled derivative, or prodrug thereof, with a compound of Formula (D), or a salt thereof, to provide a compound of Formula (II), or a salt thereof:

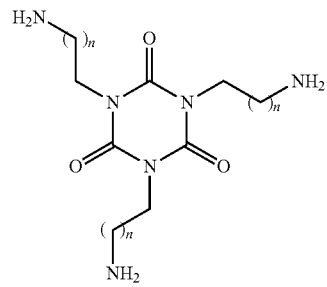

wherein $R^C$ and n are as described herein.

In another aspect, provided are methods of preparing the compounds of any one of Formulae (III-1)-(III-3), and salts thereof, the methods comprising reacting a compound of Formula (A), or a solvate, hydrate, polymorph, co-crystal, tautomer, stereoisomer, or isotopically labeled derivative thereof, with a compound of Formula (B), or a salt thereof, to provide a compound of Formula (I), or a salt thereof, wherein $R^A$, $R^B$, and m are as described herein.

In another aspect, the present invention provides methods of preparing the compounds of Formula (IV), and salts thereof, the methods comprising reacting a compound of Formula (C), or a salt, solvate, hydrate, polymorph, co-crystal, tautomer, isotopically labeled derivative, or prodrug thereof, with a compound of Formula (D), or a salt thereof, to provide a compound of Formula (IV), or a salt thereof, wherein $R^C$ and n are as described herein.

The step(s) of the methods of preparing the compounds of the invention may be performed under any suitable conditions. A suitable condition is a combination of physical and chemical parameters under which an intended product (e.g., a compound of any one of Formulae (I)-(IV), or a salt thereof) or intermediate may be formed using the inventive methods. A suitable condition may include a suitable solvent. In certain embodiments, the suitable solvent is an organic solvent. In certain embodiments, the suitable solvent is an alkyl alcohol (e.g., methanol, ethanol, propanol, and butanol). In certain embodiments, the suitable solvent is ethanol. In certain embodiments, the suitable solvent is acetone, acetonitrile (ACN), N,N-dimethylformamide (DMF), N,N-dimethylacetamide (DMA), dimethysulfoxide (DMSO), ethyl acetate (EtOAc), N-methyl-2-pyrrolidone (NMP), 2-pyrrolidone, tetrahydrofuran (THF), benzene, toluene, xylene, or a mixture thereof. In certain embodiments, the suitable solvent is an inorganic solvent. In certain embodiments, the suitable solvent is water.

Compounds of any one of Formulae (A)-(D), or salts, solvates, hydrates, polymorphs, co-crystals, tautomers, stereoisomers, isotopically labeled derivatives, or prodrugs thereof, may be substantially free of impurities and present in a suitable solvent described herein at a suitable concentration. In certain embodiments, the suitable concentration is at least about 10 μM, at least about 100 μM, at least about 1 mM, at least about 10 mM, at least about 100 mM, at least about 1 M, or at least about 10 M, as solubility permits. In certain embodiments, the suitable concentration is lower than about 10 M, lower than about 1 M, lower than about 100 mM, lower than about 10 mM, lower than about 1 mM, lower than about 100 μM, or lower than about 10 μM, as the solubility permits.

Combinations of the above-referenced ranges (e.g., at least about 1 mM and lower than about 1 M) are also within the scope of the invention.

A suitable condition may include a suitable ratio of the amount of a compound of a compound of Formula (A), or a solvate, hydrate, polymorph, co-crystal, tautomer, stereoisomer, or isotopically labeled derivative thereof, to the amount of a compound of Formula (B), or a salt thereof. A suitable condition may also include a suitable ratio of the amount of a compound of Formula (C), or a salt, solvate, hydrate, polymorph, co-crystal, tautomer, isotopically labeled derivative, or prodrug thereof, to the amount of a compound of Formula (D), or a salt thereof. In certain embodiments, the suitable ratio described herein is at least about at least about 1:300, at least about 1:100, at least about 1:30, at least about 1:10, or at least about 1:3 mol/mol. In certain embodiments, the suitable ratio is less than about 1:3, less than about 1:10, less than about 1:30, less than about 1:100, or less than about 1:300 mol/mol. Combinations of the above-referenced ranges (e.g., at least about 1:30 and less than about 1:3 mol/mol) are also within the scope of the invention. In certain embodiments, the ratio is about 1:3 mol/mol.

A suitable condition may also include a suitable temperature under which a step of a method of preparing the compounds of the invention is performed. In certain embodiments, the suitable temperature is at least about 20° C., at least about 23° C., at least about 25° C., at least about 40° C., at least about 60° C., at least about 80° C., at least about 100° C., or at least about 120° C. In certain embodiments, the suitable temperature is lower than about 120° C., lower than about 100° C., lower than about 80° C., lower than about 60° C., lower than about 40° C., lower than about 25° C., lower than about 23° C., or lower than about 20° C. Combinations of the above-referenced ranges (e.g., at least about 40° C. and lower than about 80° C.) are also within the scope of the invention. A suitable temperature may be a variable temperature during a step of a method of preparing the compounds of the invention.

A suitable condition may also include a suitable pressure under which a step of a method of preparing the compounds of the invention is performed. In certain embodiments, the suitable pressure is at least about 1 atmosphere, at least about 2 atmospheres, at least about 5 atmospheres, at least about 10 atmospheres, at least about 20 atmospheres, or at least about 50 atmospheres. In certain embodiments, the suitable pressure is lower than about 50 atmospheres, lower than about 20 atmospheres, lower than about 10 atmospheres, lower than about 5 atmospheres, lower than about 2 atmospheres, or lower than 1 about atmosphere. Combinations of the above-referenced ranges (e.g., at least about 1 atmosphere and lower than about 10 atmospheres) are also within the scope of the invention.

In certain embodiments, the suitable pressure is about 1 atmosphere.

A suitable condition may also include a suitable atmosphere under which a step of a method of preparing the compounds of the invention is performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that a step of a method of preparing the compounds of the invention lasts. In certain embodiments, the suitable time duration is in the order of minutes (e.g., about 10 minutes or about 30 minutes), hours (e.g., about 1 hour, about 2 hours, about 4 hours, about 6 hours, or about 12 hours), or days (e.g., about 1 day).

A suitable condition may also include irradiation with microwave, such as what is described in Majetich et al., *J. Microwave Rower and Electromagnetic Energy* 1995, 30, 27-45. A suitable condition may further include shielding from ambient light and/or agitating (e.g., stirring).

One or more intermediates resulting from a step of a method of preparing the compounds of the invention may be isolated and/or purified, and the isolated and/or purified intermediates may be reacted in a next step of the method. The isolated and/or purified intermediates may be substantially free of impurities or may contain one or more other components, such as reagents and solvents employed in the step yielding the intermediates, and byproducts. The one or more intermediates may also be reacted in a next step without being isolated and/or purified. The intermediates and/or intended products of the methods of preparing the compounds of the invention may be isolated and/or purified using methods known in the art, such as chromatography (e.g., normal phase chromatography (e.g., silica gel flash chromatography), reverse phase chromatography (e.g., high performance liquid chromatography (HPLC)), precipitation, decanting, filtration, centrifuge, trituration, crystallization, recrystallization, liquid-liquid phase separation, evaporation, and drying. In certain embodiments, the intended products described herein are substantially free of impurities.

EXAMPLES

In order that the invention described herein may be more fully understood, the following examples are set forth. It should be understood that these examples are for illustrative purposes only and are not to be construed as limiting this invention in any manner.

Combinatorial synthetic approaches have been used to develop cationic lipids (lipidoids) for siRNA delivery. See, e.g., Akinc, A., et al., *Nat. Biotechnol.* 2008. 26(5): p. 561-9; Love Kevin, T., et al., *Proc. Natl. Acad. Sci. U.S.A.* 107(5): p. 1864-9; Siegwart, D. J., et al., *Proc. Natl. Acad. Sci. U.S.A.* 108(32): p. 12996-3001. A number of these cationic lipids have shown significant silencing effects in vivo. See, e.g., Leuschner, F., et al., *Nat. Biotechnol.* 29(11): p. 1005-10. Prior studies have identified key chemical and structural features and formulation methods for the development of new cationic lipids. See, e.g., Akinc, A., et al., *Mol. Ther.* 2009. 17(5): p. 872-9; Akinc, A., et al., *Mol. Ther.* 18(7): p. 1357-64; Semple, S. C., et al., *Nat. Biotechnol.* 28(2): p. 172-6. For example, cationic lipids possessing 12 or more carbons in tail length and multiple tails have shown to be active in siRNA delivery. See, e.g., Love Kevin, T., et al., *Proc. Natl. Acad. Sci. U.S.A.* 107(5): p. 1864-9. In order to improve efficacy, tissue and cell-type selectivity, tolerability, and toxicity, new chemical scaffolds need to be designed and investigated.

Previous studies have shown that 1,3,5-triazinane-2,4,6-trione derivatives, such as compound 1, were tolerated in mice and rats through oral uptake an inhalation. Therefore, it was thought that the 1,3,5-triazinane-2,4,6-trione derivatives may be safe for the delivery of agents (e.g., siRNA, mRNAs, and pDNAs) in humans. Novel 1,3,5-triazinane-2,4,6-trione derivatives (i.e., compounds of any one of Formulae (I)-(IV), and salts thereof) have been developed. Current results demonstrate that delivery systems including the novel 1,3,5-triazinane-2,4,6-trione derivatives are a new platform for efficient, selective, and safe delivery of an agent, such as an siRNA, mRNA, or pDNA, to a subject, which shows great potential for the treatment and/or prevention of various diseases in the subject.

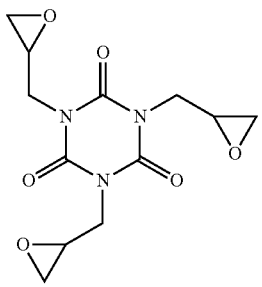

1

Example 1

Preparation of the Compounds of Formula (I)

Compounds of Formula (I), and salts thereof, may be prepared by the synthetic sequence outlined below in Scheme 1 or similar methods. Alternatively, compounds of Formula (I) may be synthesized by other methods described herein or known in the art.

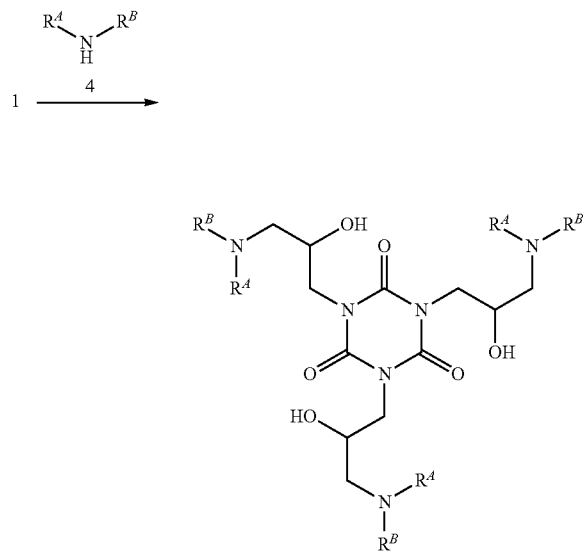

Scheme 1. Exemplary synthesis of certain compounds of Formula (I), wherein $R^A$ and $R^B$ are as descried herein.

In one set of experiments, a mixture of compounds 1 and 4 in EtOH was irradiated in the microwave oven at 150° C. for 5 h. The reaction mixture was purified by flash column chromatography to yield a compound of Formula (I). Compound Compound I-1: $^1$H NMR (500 MHz, CDCl$_3$) δ 4.08-4.13 (m, 3H), 3.99-4.01 (m, 3H), 3.84-3.88 (m, 3H), 2.30-2.48 (m, 12H), 2.24 (s, 9H), 1.27-1.44 (m, 24H), 0.88 (t, J=7.0 Hz, 9H). HRMS (ESI) calcd for $C_{33}H_{67}N_6O_6$[M+H]$^+$643.5122. found 643.5203.

Compound I-2: $^1$H NMR (500 MHz, CDCl$_3$) δ 4.08-4.13 (m, 3H), 3.98-4.00 (m, 3H), 3.83-3.86 (m, 3H), 2.33-2.47 (m, 12H), 2.24 (s, 9H), 1.26-1.46 (m, 36H), 0.88 (t, J=7.0 Hz, 9H). HRMS (ESI) calcd for $C_{39}H_{78}N_6O_6$ [M+H]$^+$727.6056. found 727.6116.

Compound I-3: $^1$H NMR (500 MHz, CDCl$_3$) δ 4.08-4.13 (m, 3H), 3.99-4.00 (m, 3H), 3.84-3.87 (m, 3H), 2.30-2.47 (m, 12H), 2.24 (s, 9H), 1.26-1.44 (m, 60H), 0.88 (t, J=7.0 Hz, 9H). HRMS (ESI) calcd for $C_{51}H_{102}N_6O_6$ [M+H]$^+$895.7934. found 895.7937.

Compound I-4: $^1$H NMR (500 MHz, CDCl$_3$) δ 4.08-4.11 (m, 3H), 3.98-3.99 (m, 3H), 3.84-3.87 (m, 3H), 2.33-2.45 (m, 12H), 2.24 (s, 9H), 1.25-1.44 (m, 96H), 0.88 (t, J=7.0 Hz, 9H). HRMS (ESI) calcd for $C_{69}H_{139}N_6O_6$ [M+H]$^+$ 1148.0751. found 1148.0615.

Compound I-5: $^1$H NMR (500 MHz, CDCl$_3$) δ 4.08-4.13 (m, 3H), 3.93-3.95 (m, 3H), 3.82-3.84 (m, 3H), 1.34-1.42 (m, 12H), 1.26-1.33 (m, 12H), 1.39-1.41 (m, 12H), 1.27-1.30 (m, 12H), 0.89 (t, J=7.0 Hz, 18H). HRMS (ESI) calcd for $C_{36}H_{73}N_6O_6$[M+H]$^+$685.5592. found 685.5597.

Compound I-6: $^1$H NMR (500 MHz, CDCl$_3$) δ 4.08-4.13 (m, 3H), 3.92-3.93 (m, 3H), 3.80-3.84 (m, 3H), 2.33-2.53 (m, 18H), 1.26-1.42 (m, 48H), 0.88 (t, J=7.0 Hz, 9H). HRMS (ESI) calcd for $C_{48}H_{96}N_6O_6$ [M+H]$^+$853.7464. found, 853.7468.

Compound I-7: $^1$H NMR (500 MHz, CDCl$_3$) δ 4.07-4.13 (m, 3H), 3.91-3.95 (m, 3H), 3.80-3.85 (m, 3H), 2.35-2.52 (m, 18H), 1.26-1.42 (m, 72H), 0.88 (t, J=7.5 Hz, 9H). HRMS (ESI) calcd for $C_{60}H_{120}N_6O_6$ [M+H]$^+$1021.9342. found 1021.9387.

Compound I-8: $^1$H NMR (500 MHz, CDCl$_3$) δ 4.08-4.12 (m, 3H), 3.92-3.94 (m, 3H), 3.80-3.83 (m, 3H), 2.35-2.52 (m, 18H), 1.26-1.42 (m, 96H), 0.88 (t, J=7.0 Hz, 9H). HRMS (ESI) calcd for $C_{72}H_{144}N_6O_6$ [M+H]$^+$1190.1220. found 1190.1140.

Compound I-9: $^1$H NMR (500 MHz, CDCl$_3$) δ 4.08-4.12 (m, 3H), 3.90-3.94 (m, 3H), 3.80-3.84 (m, 3H), 2.35-2.52 (m, 18H), 1.25-1.42 (m, 132H), 0.88 (t, J=7.0 Hz, 9H). HRMS (ESI) calcd for $C_{90}H_{180}N_6O_6$ [M+H]$^+$1442.4037. found 1442.4077.

Example 2

Preparation of the Compounds of Formula (II)

Compounds of Formula (II), and salts thereof, may be prepared by the synthetic sequence outlined below in Scheme 2. Alternatively, compounds of Formula (II) may be synthesized by other methods described herein or known in the art.

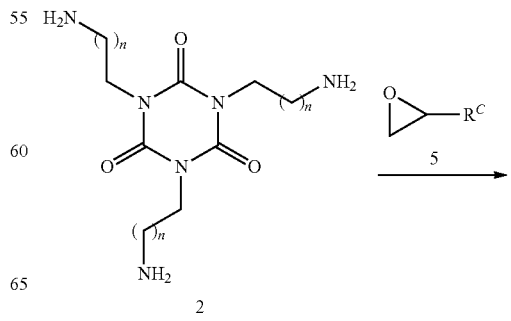

Scheme 2. Exemplary synthesis of compounds of Formula (II), wherein $R^C$ and n are as descried herein.

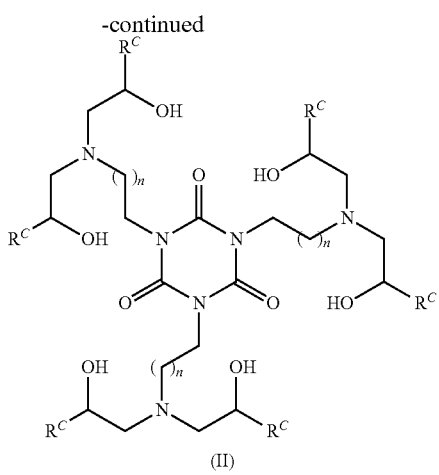

(II)

In one set of experiments, a mixture of compounds 2 and 5 in EtOH was irradiated in the microwave oven at 150° C. for 5 h. The reaction mixture was purified by flash column chromatography to yield a compound of Formula (II).

Example 3

In Vivo Liver Gene Silencing in Mice

C57BL/6 mice (Charles River Labs) were used for siRNA silencing experiments. Prior to injection, compositions were diluted in PBS at siRNA (e.g., SEQ ID NO:1 (siFVII sense): 5'-GGAucAucucAAGucuuAcT*T-3'; SEQ ID NO:2 (antisense): 5'-GuAAGAcuuGAGAuGAuccT*T-3') concentrations such that each mouse was administered a dose of 0.01 mL/g body-weight. Formulations were administered intravenously via tail vein injection. After 48 or 72 h, body-weight gain/loss was measured and mice were anaesthetized by isofluorane inhalation for blood sample collection by retroorbital eye bleed. Serum was isolated with serum separation tubes (Falcon tubes, Becton Dickinson) and Factor VII (FVII) protein levels were analyzed by chromogenic assay (Biophen FVII, Aniara Corporation). A standard curve was constructed using samples from PBS-injected mice and relative Factor VII expression was determined by comparing treated groups to untreated PBS control. Compound 3 (C12-200) was used as a positive control.

3

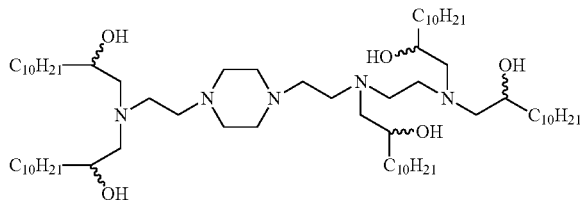

Figure 2:
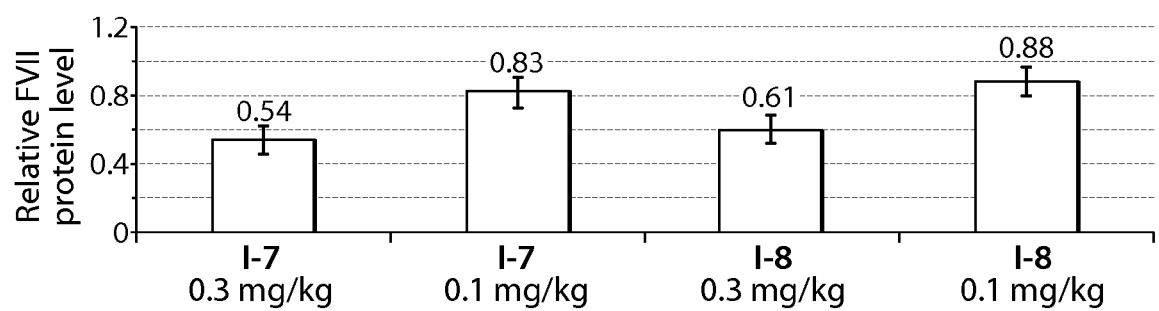
FIG. 2 shows the results of an in vivo liver gene silencing experiment. Compounds I-7 and I-8 were dosed in mice at about 0.1 mg/kg and about 0.3 mg/kg. Relative Factor VII (FVII) protein levels were measured 24 hours post dose.

The results are illustrated in FIGS. 1 and 2. Compounds I-1 to I-9 showed moderate to strong inhibition of an FVII expression in mice at the dose of 1 mg/kg (FIG. 1). In particular, compounds 7 and 8 showed more than 80% gene silencing at the dose of about 0.1 mg/kg, about 0.3 mg/kg, or about 1 mg/kg (FIGS. 1 and 2). This result suggests that the long alkyl moieties of compounds I-7 and I-8 may contribute to the improved delivery efficiency over compounds I-1 to I-6 and I-9.

Example 4

In Vitro Luciferase Gene Silencing

Figure 3:
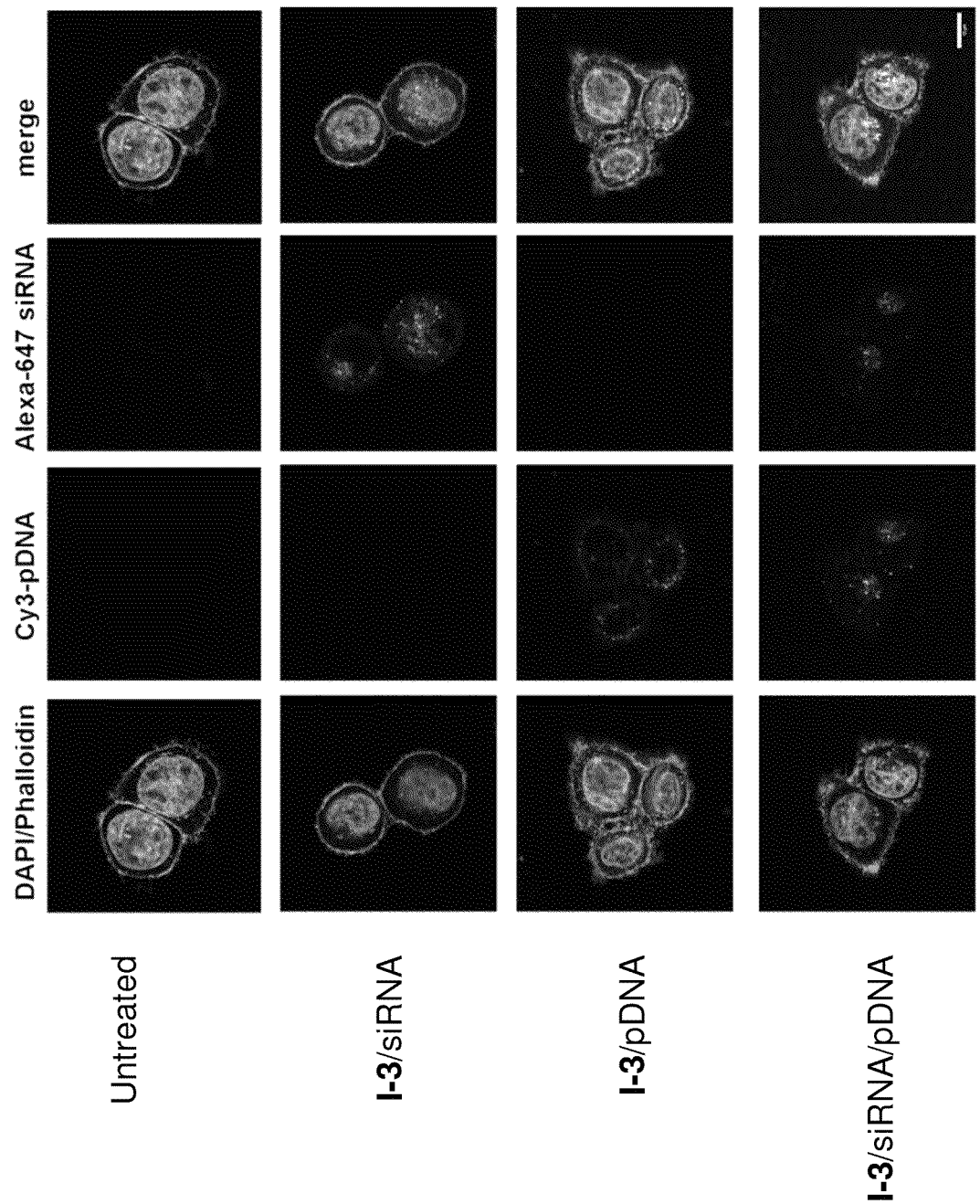
FIG. 3 shows the uptake of siRNA and/or plasmid DNA (pDNA) delivered by compositions including compound I-3.
Figures 4A, 4B:
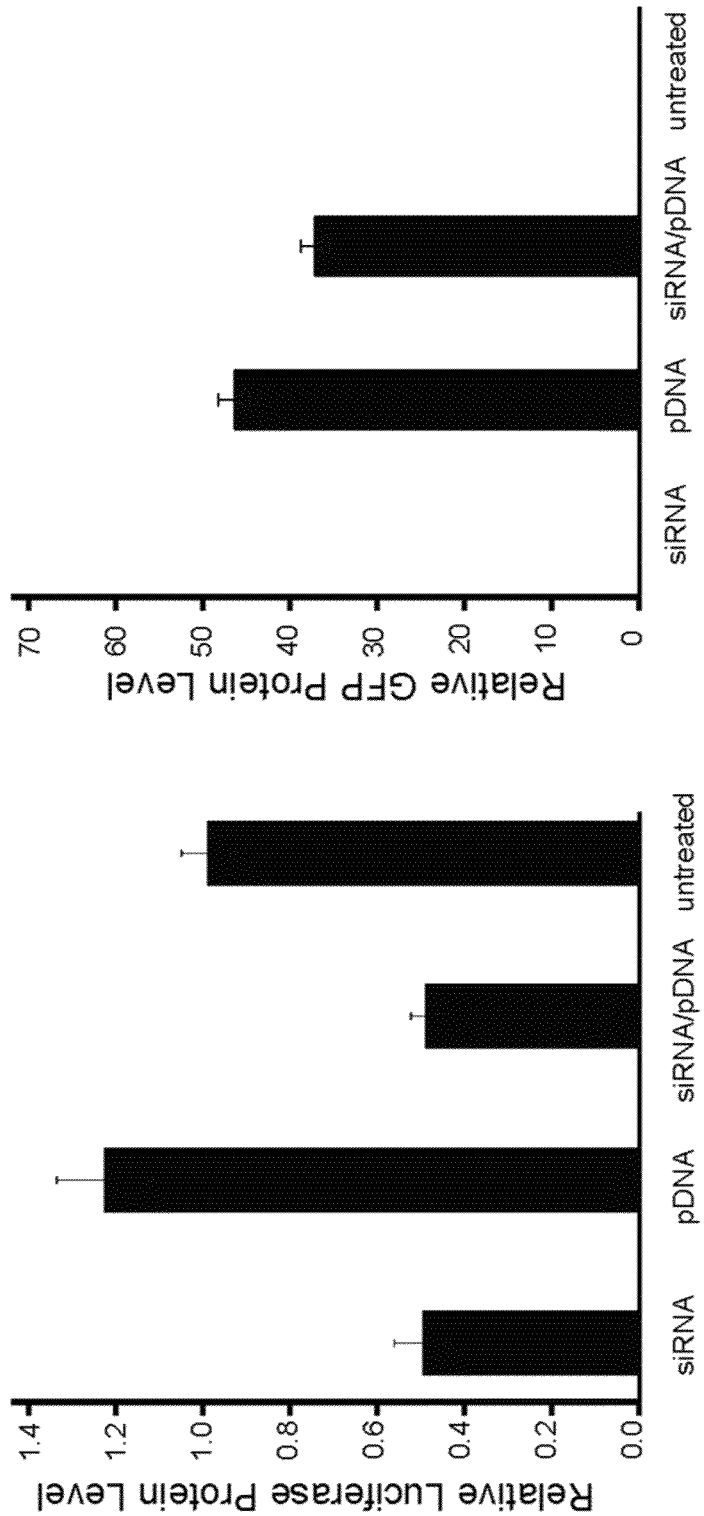
FIGS. 4A-4B show the gene silencing of firefly luciferase (FIG. 4A) and gene expression of GFP protein in HeLa cells (FIG. 4B).

HeLa cells, stably expressing firefly luciferase and *Renilla* luciferase, were seeded (14,000 cells/well) into each well of an opaque white 96-well plate (Corning-Costar) and allowed to attach overnight in growth medium. Growth medium was composed of 90% phenol red-free DMEM, 10% FBS, 100 units/ml penicillin, 100 mg/ml streptomycin (Invitrogen). Cells were transfected with LNPs formulated with Alexa-647-siRNA, and/or GFP pDNA cy3-pDNA; anti-luciferase siRNA, and/or GFP pDNA by addition of formulated particles to growth medium. Transfections were performed in quadruplicate. Cells were allowed to grow for 1 d at 37° C., 5% $CO_2$ and were then analyzed for luciferase expression. Images were taken using LSM 710-confocal microscopy. Firefly and *Renilla* luciferase expression was analyzed using Dual-Glo assay kits (Promega). Luminescence was measured using a Victor3 luminometer (Perkin Elmer). GFP signal was analyzed by FACS. FIG. 3 shows that both siRNA and pDNA delivered by compositions including compound I-3 were uptaken by HeLa cells. FIGS. 4A-4B show that siRNA and pDNA formulated I-3 simultaneously silenced luciferase expression and expressed GFP protein in HeLa cells.

Example 5

In Vivo Endothelial Silencing in Mice

Figure 5:
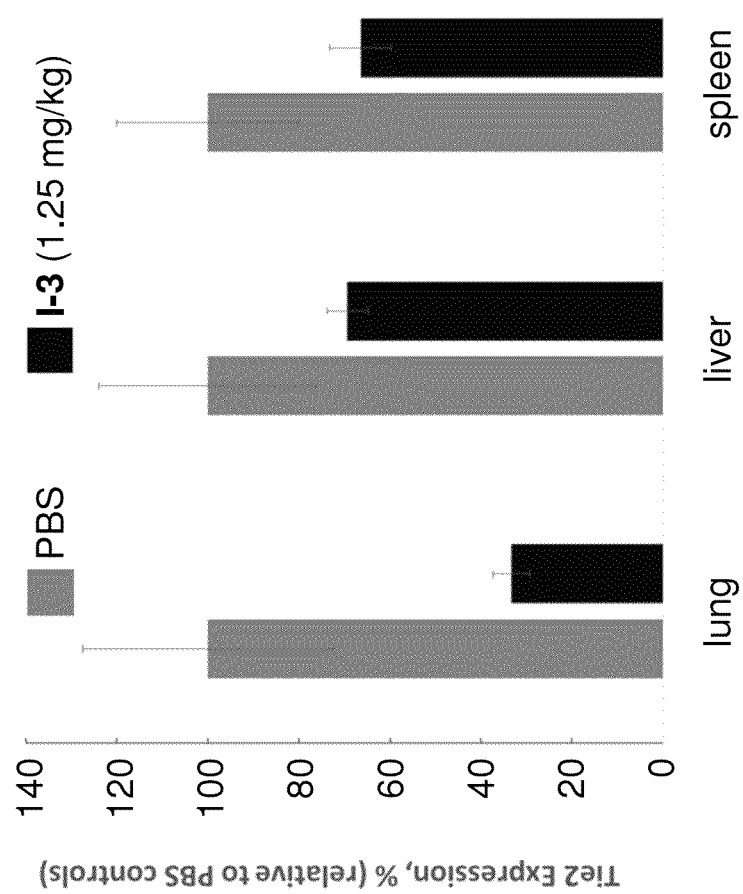
FIG. 5 shows the silencing of Tie2 by the compositions including compound I-3 in the lung, liver, and spleen in mice.

Endothelial silencing were examined 48 h after injection. Mice were sacrificed by $CO_2$ asphyxiation, and the lung, liver, and spleen tissues were harvested and immediately frozen in liquid nitrogen. Frozen tissues were pulverized, and tissue lysates were prepared in Tissue and Cell Lysis Buffer (Epicentre) supplemented with 0.5 mg/ml Proteinase K (Epicentre). Tie2 silencing was evaluated in lysates from all 3 tissues collected using a branched DNA assay (QuantiGene 2.0 Reagent System, Affymetrix). A standard curve for each tissue and target gene was constructed using samples from PBS-treated mice, and the relative silencing in treated groups was determined by measuring each individual target gene/GAPDH level and normalizing to the corresponding ratio for PBS-treated mice controls. FIG. 5 shows that compositions including compound I-3 significantly silenced the expression of Tie2 in the lung endothelia cells and silenced the expression of Tie2 in the liver and spleen endothelia cells.

Example 6

Luciferase pDNA Expression Experiments

C57BL/6 mice (Charles River Labs) were used for luciferase pDNA expression experiments. Prior to injection, compositions were diluted in PBS at siRNA (such as ones described herein) concentrations such that each mouse was administered a dose of 0.01 mL/g body-weight. The compositions were administered intravenously via tail vein injection. After 8 h, Mice were injected with D-luciferin and sacrificed 8 mins after injection by $CO_2$ asphyxiation, and the lung, liver, kidney, and spleen tissues were harvested and immediately imaged by IVIS Series Pre-clinical In Vivo Imaging Systems. FIGS. 6A-6B show that compositions including compound I-3 significantly induced luciferase expression in the lung and spleen. The results also demonstrate that compositions that included compound I-3 were able to deliver not only siRNA, but also pDNA, to the mice (e.g., to the lung and/or spleen of the mice).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I):

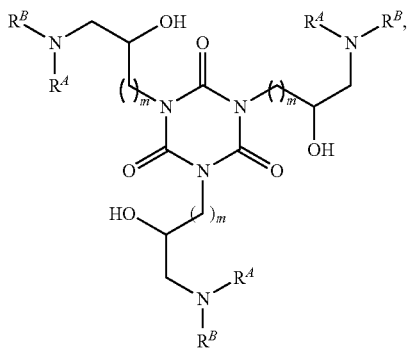

or a salt thereof;
wherein:
each instance of $R^A$ is independently substituted or unsubstituted $C_{6-13}$ alkyl;
each instance of $R^B$ is independently substituted or unsubstituted $C_{6-13}$ alkyl; and
each instance of m is independently 1, 2, 3, 4, 5, or 6.

2. The compound of claim 1, wherein:
all instances of $R^A$ are substituted or unsubstituted $C_{6-13}$ alkyl;
all instances of $R^B$ are substituted or unsubstituted $C_{6-13}$ alkyl; and
all instances of m are 1, 2, 3, 4, 5, or 6.

3. The compound of claim 1, wherein at least one instance of $R^A$ is unsubstituted $C_{6-13}$ alkyl.

4. The compound of claim 1, wherein at least two instances of $R^A$ are unsubstituted $C_{6-13}$ alkyl.

5. The compound of claim 1, wherein all instances of $R^A$ are unsubstituted $C_{6-13}$ alkyl.

6. The compound of claim 1, wherein:
all instances of $R^A$ are unsubstituted $C_{6-13}$ alkyl; and
all instances of $R^B$ are unsubstituted $C_{6-13}$ alkyl.

7. The compound of claim 1, wherein all instances of m are 1.

8. The compound of claim 1, wherein:
all instances of $R^A$ are unsubstituted $C_{6-13}$ alkyl;
all instances of $R^B$ are unsubstituted $C_{6-13}$ alkyl; and
all instances of m are 1.

9. The compound of claim 1, wherein the compound is of the formula:

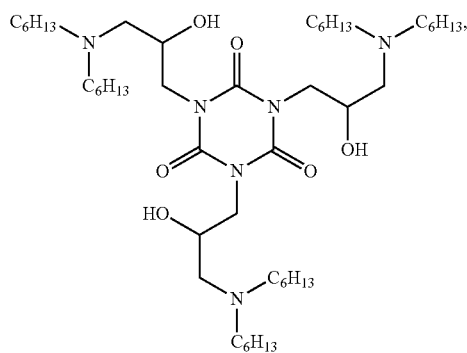

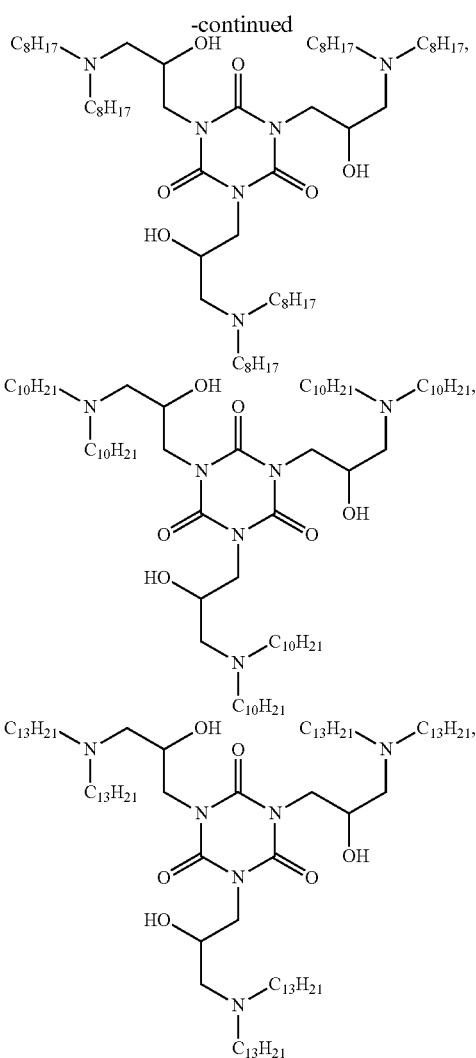

or a salt thereof.

10. A compound of Formula (II):

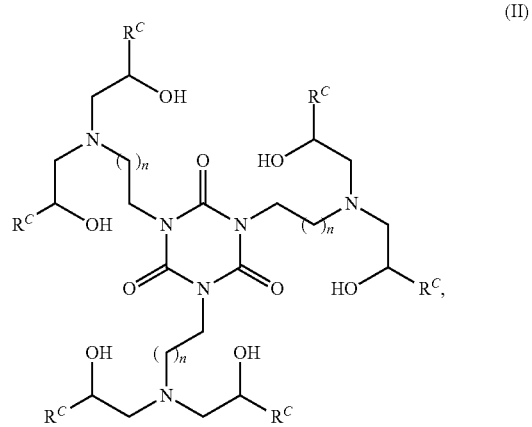

or a salt thereof;
wherein:
each instance of $R^C$ is independently substituted or unsubstituted alkyl; and
each instance of n is independently 1, 2, 3, 4, or 5.

11. A method of preparing a compound of claim 1, or a salt thereof, the method comprising:
reacting a compound of Formula (A) with a compound of Formula (B), or a salt thereof, to provide a compound of claim 1, or a salt thereof:

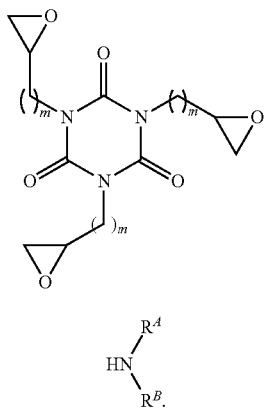
(A)

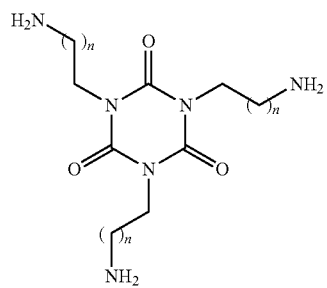
(B)

12. A method of preparing a compound of claim 10, or a salt thereof, the method comprising:
reacting a compound of Formula (C), or a salt thereof, with a compound of Formula (D), or a salt thereof, to provide a compound of claim 10, or a salt thereof:

(C)

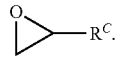
(D)

13. The compound of claim 1, wherein all instances of $R^A$ are unsubstituted $C_{8\text{-}10}$ alkyl.

14. The compound of claim 1, wherein:
all instances of $R^A$ are unsubstituted $C_{8\text{-}10}$ alkyl; and
all instances of $R^B$ are unsubstituted $C_{8\text{-}10}$ alkyl.

15. The compound of claim 1, wherein:
all instances of $R^A$ are unsubstituted $C_{8\text{-}10}$ alkyl; and
all instances of $R^B$ are unsubstituted $C_{8\text{-}10}$ alkyl
all instances of m are 1.

16. The compound of claim 1, wherein at least one instance of $R^A$ is substituted $C_{6\text{-}13}$ alkyl.

17. The compound of claim 1, wherein at least two instances of $R^A$ are substituted $C_{6\text{-}13}$ alkyl.

18. The compound of claim 1, wherein all instances of $R^A$ are substituted $C_{6\text{-}13}$ alkyl.

19. The compound of claim 10, wherein at least one instance of $R^C$ is unsubstituted $C_{6\text{-}18}$ alkyl.

20. The compound of claim 10, wherein at least one instance of $R^C$ is substituted $C_{6\text{-}18}$ alkyl.

21. The compound of claim 10, wherein all instances of $R^C$ are unsubstituted $C_{6\text{-}18}$ alkyl.

22. The compound of claim 10, wherein all instances of $R^C$ are substituted $C_{6\text{-}18}$ alkyl.

23. The compound of claim 10, wherein all instances of n are 1.

24. The compound of claim 10, wherein:
all instances of $R^C$ are unsubstituted alkyl; and
all instances of n are 1.

25. The compound of claim 10, wherein:
all instances of $R^C$ are unsubstituted $C_{6\text{-}18}$ alkyl; and
all instances of n are 1.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: siFVII sense siRNA
<220> FEATURE:
<221> NAME/KEY: misc_feature
<222> LOCATION: (20)..(20)
<223> OTHER INFORMATION: t is modified with *

<400> SEQUENCE: 1
ggaucaucuc aagucuuact t                                      21

<210> SEQ ID NO 2
<211> LENGTH: 21
<212> TYPE: DNA
<213> ORGANISM: Artificial Sequence
<220> FEATURE:
<223> OTHER INFORMATION: siFVII antisense siRNA
<220> FEATURE:
<221> NAME/KEY: misc_feature
<222> LOCATION: (20)..(20)
<223> OTHER INFORMATION: t is modified with *

<400> SEQUENCE: 2
guaagacuug agaugaucct t                                      21
```